(12) United States Patent
Choi et al.

(10) Patent No.: US 10,973,927 B2
(45) Date of Patent: Apr. 13, 2021

(54) MATERIALS AND METHODS FOR EFFECTIVE IN VIVO DELIVERY OF DNA NANOSTRUCTURES TO ATHEROSCLEROTIC PLAQUES

(71) Applicant: THE CHINESE UNIVERSITY OF HONG KONG, Hong Kong (CN)

(72) Inventors: Chung Hang Jonathan Choi, Hong Kong (CN); Lei Zhang, Yangzhou (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 0 days.

(21) Appl. No.: 16/113,454

(22) Filed: Aug. 27, 2018

(65) Prior Publication Data
US 2019/0060485 A1   Feb. 28, 2019

Related U.S. Application Data

(60) Provisional application No. 62/550,995, filed on Aug. 28, 2017.

(51) Int. Cl.
| *A61K 47/69* | (2017.01) |
| *A61K 9/00* | (2006.01) |
| *A61K 49/18* | (2006.01) |
| *A61K 49/00* | (2006.01) |
| *A61P 9/10* | (2006.01) |
| *A61K 47/54* | (2017.01) |
| *A61K 47/60* | (2017.01) |
| *A61K 9/51* | (2006.01) |

(52) U.S. Cl.
CPC ........ *A61K 47/6935* (2017.08); *A61K 9/0019* (2013.01); *A61K 9/513* (2013.01); *A61K 47/549* (2017.08); *A61K 47/60* (2017.08); *A61K 47/6923* (2017.08); *A61K 49/0093* (2013.01); *A61K 49/186* (2013.01); *A61K 49/1845* (2013.01); *A61P 9/10* (2018.01)

(58) Field of Classification Search
None
See application file for complete search history.

(56) References Cited

U.S. PATENT DOCUMENTS

| 8,252,756 | B2 | 8/2012 | Mirkin et al. |
| 9,139,827 | B2 | 9/2015 | Mirkin et al. |
| 9,376,690 | B2 | 6/2016 | Mirkin et al. |
| 9,844,562 | B2 | 12/2017 | Mirkin et al. |
| 2003/0113740 | A1 | 6/2003 | Mirkin et al. |
| 2005/0271745 | A1* | 12/2005 | Gruettner ............... A61K 47/61 424/646 |
| 2006/0051798 | A1 | 3/2006 | Mirkin et al. |
| 2008/0206150 | A1* | 8/2008 | Louie .................. A61K 49/183 424/9.32 |
| 2008/0311669 | A1 | 12/2008 | Mirkin et al. |
| 2009/0221095 | A1 | 9/2009 | Mirkin et al. |
| 2010/0099858 | A1 | 4/2010 | Mirkin et al. |
| 2011/0059431 | A1 | 3/2011 | Mirkin et al. |
| 2012/0244230 | A1 | 9/2012 | Mirkin et al. |
| 2013/0101512 | A1 | 4/2013 | Mirkin et al. |
| 2013/0172404 | A1 | 7/2013 | Mirkin et al. |
| 2014/0017165 | A1* | 1/2014 | Wang ................... A61K 9/5146 424/1.37 |
| 2015/0031745 | A1 | 1/2015 | Mirkin et al. |
| 2015/0259680 | A1 | 9/2015 | Mirkin et al. |
| 2016/0159834 | A1 | 6/2016 | Lee et al. |
| 2016/0281086 | A1 | 9/2016 | Mirkin et al. |
| 2017/0044544 | A1 | 2/2017 | Mirkin et al. |
| 2017/0082614 | A1 | 3/2017 | Mirkin et al. |
| 2017/0137809 | A1 | 5/2017 | Mirkin et al. |

FOREIGN PATENT DOCUMENTS

| AU | 2014262264 A1 | 12/2014 |
| AU | 2016219644 A1 | 9/2016 |
| AU | 2016238902 A1 | 10/2016 |
| AU | 2016269532 A1 | 1/2017 |
| AU | 2015349680 A1 | 6/2017 |
| CA | 2 958 431 A1 | 2/2016 |
| CA | 2 958 577 A1 | 2/2016 |
| CN | 104107432 A | 10/2014 |
| JP | 2015-017124 A | 1/2015 |
| KR | 10-2016-0056492 A | 5/2016 |
| MX | 2011007350 A | 9/2011 |

(Continued)

OTHER PUBLICATIONS

Zheng, D. et al., "Topical delivery of siRNA-based spherical nucleic acid nanoparticle conjugates for gene regulation", *PNAS*, Jul. 24, 2012, 109(30):11975-11980.
Randeria, P.S. et al., "siRNA-based spherical nucleic acids reverse impaired wound healing in diabetic mice by ganglioside GM3 synthase knockdown", *PNAS*, May 5, 2015, 112(18):5573-5578.
Jensen, S.A. et al., "Spherical Nucleic Acid Nanoparticle Conjugates as an RNAi-Based Therapy for Glioblastoma", *Sci Transl Med*, Oct. 30, 2013, 5(209):1-13, American Association for the Advancement of Science, Washington, DC.
Kouri, F.M. et al., "miR-182 integrates apoptosis, growth, and differentiation programs in glioblastoma", *Genes & Development*, 29:732-745, Cold Spring Harbor Laboratory Press.
Radovic-Moreno, A.F. etal., "Immunomodulatory spherical nucleic acids", *PNAS*, Mar. 31, 2015, 112(13):3892-3897.
Sita, T.L. et al., "Dual bioluminescence and near-infrared fluorescence monitoring to evaluate spherical nucleic acid nanoconjugate activity in vivo", *PNAS*, Apr. 18, 2017, 114(16):4129-4134.

(Continued)

*Primary Examiner* — Tracy Vivlemore
(74) *Attorney, Agent, or Firm* — Saliwanchik, Lloyd & Eisenschenk

(57) ABSTRACT

Provided are DNA-coated nanoparticles (DNA-NPS), superparamagnetic nanoparticles (DNA-SPNs), and superparamagnetic iron oxide nanopa rticles (DNA-SPIONs) as efficient imaging agents for targeting and imaging atherosclerotic lesions and treating atherosclerotic disease. The DNA-NS, DNA-SPNs, and DNA-SPIONs can enter macrophage cells via the Class A scavenger receptor (SR-A)-mediated pathways and can be used to specifically target atheroscleortic plaques.

8 Claims, 50 Drawing Sheets
(14 of 50 Drawing Sheet(s) Filed in Color)
Specification includes a Sequence Listing.

(56) References Cited

FOREIGN PATENT DOCUMENTS

| WO | WO-02/46483 A2 | 6/2002 |
|---|---|---|
| WO | WO-02/079490 A2 | 10/2002 |
| WO | WO-03/087188 A1 | 10/2003 |
| WO | WO-2005/108614 A2 | 11/2005 |
| WO | WO-2011/017691 A2 | 2/2011 |
| WO | WO-2017/031086 A1 | 2/2017 |

OTHER PUBLICATIONS

Wang, X. et al., "Spherical nucleic acid targeting microRNA-99b enhances intestinal MFG-E8 gene expression and restores enterocyte migration in lipopolysaccharide-induced septic mice", *Scientific Reports*, Aug. 19, 2016, 6(31687):1-13.

Lewis, D.R. et al., "Sugar-based amphiphilic nanoparticles arrest atherosclerosis in vivo", *PNAS*, Mar. 3, 2015, 112(9):2693-2698.

Kamaly, N. etal., "Targeted Interleukin-10 Nanotherapeutics Developed with a Microfluidic Chip Enhance Resolution of Inflammation in Advanced Atherosclerosis", *ACS Nano*, Apr. 21, 2016, 10:5280-5292, American Chemical Society.

Kheirolomoom, A. et al., "Multifunctional Nanoparticles Facilitate Molecular Targeting and miRNA Delivery to Inhibit Atherosclerosis in ApoE$^{-/-}$ Mice", *ACSNANO*, Aug. 26, 2015, 9(9):8885-8897, American Chemical Society.

Mozaffarian, D. et al., "Heart disease and stroke statistics—2015 update: a report from the American Heart Association", Dec. 17, 2014, pp. 1-4.

Frostegård, J. "Immunity, atherosclerosis, and cardiovascular disease", *BMC Medicine*, 2013, 11(117):1-13, BioMed Central.

Hansson, G.K. et al., "The immune system in atherosclerosis", *Nature Immunology*, Mar. 2011, 12(3):204-212, Nature America, Inc.

Libby, P. et al., "Progress and challenges in translating the biology of atherosclerosis", *Nature*, May 19, 2011, 473:317-325, Macmillan Publishers Limited.

Weissleder, R. et al., "Imaging macrophages with nanoparticles", *Nature Materials*, Feb. 2014, 13:125-138, Macmillan Publishers Limited.

Go, A.S. et al., "Heart Disease and Stroke Statistics—2014 Update", *Circulation*, 2013, 129:e28-e292, American Heart Association, Inc.

Mulder, W.J.M. et al., "Imaging and Nanomedicine in Inflammatory Atherosclerosis", *Sci Transl Med*, Jun. 4, 2014, 6(239):1-11, the American Association for the Advancement of Science, Washington, DC.

Tarkin, J.M. et al., "Imaging Atherosclerosis", *Circulation Research*, Feb. 19, 2016, 118:750-769, Wolters Kluwer.

Corti, R. et al., "New Understanding of Atherosclerosis (Clinically and Experimentally) with Evolving MRI Technology in Vivo", *Annals New York Academy of Sciences*, 2001, 947:181-198.

Lobatto, M.E. et al., "Perspectives and opportunities for nanomedicine in the management of atherosclerosis", *Nat Rev Drug Discov.*, 2011, 10(11):835-852, Macmillan Publishers Limited.

Kuai, R. et al., "High-Density Lipoproteins: Nature's Multifunctional Nanoparticles", *ACS Nano*, 2016, 10:3015-3041, American Chemical Society.

Bobryshev, Y.V. et al., "Macrophages and Their Role in Atherosclerosis: Pathophysiology and Transcriptome Analysis", *BioMed Research International*, 2016, 2016(9582430):13 pages, Hindawi Publishing Corporation.

McAteer, M.A. et al., "An approach to molecular imaging of atherosclerosis, thrombosis, and vascular inflammation using microparticles of iron oxide", *Atherosclerosis*, 2010, 209:18-27, Elsevier Ireland Ltd.

McAteer, M.A. et al., "Magnetic Resonance Imaging of Endothelial Adhesion Molecules in Mouse Atherosclerosis Using Dual-Targeted Microparticles of Iron Oxide", *Arterioscler Thromb Vasc Biol.*, Jan. 2008, 28:77-83, 2007 American Heart Association, Inc.

Chung, E.J., "Targeting and therapeutic peptides in nanomedicine for atherosclerosis", *Experimental Biology and Medicine*, 2016, 241:891-898, the Society for Experimental Biology and Medicine.

Wang, Y. et al., "In vivo MR and Fluorescence Dual-modality Imaging of Atherosclerosis Characteristics in Mice Using Profilin-1 Targeted Magnetic Nanoparticles", *Theranostics*, 2016, 6(2):272-286, Ivyspring International Publisher.

Chen, W. et al., "Collagen-Specific Peptide Conjugated HDL Nanoparticles as MRI Contrast Agent to Evaluate Compositional Changes in Atherosclerotic Plaque Regression", *JACC: Cardiovascualr Imaging*, Mar. 2013, 6(3):373-384, Elsevier Inc.

Sinha, A. et al., "Nanoparticle targeting to diseased vasculature for imaging and therapy", *Nanomedicine: Nanotechnology, Biology, and Medicine*, 2014, 10:1003-1012, Elsevier Inc.

Hamzah, J. et al., "Specific penetration and accumulation of a homing peptide within atherosclerotic plaques of apolipoprotein E-deficient mice", *PNAS*, Apr. 26, 2011, 108(17):7154-7159.

Chen, W. et al., "Incorporation of an apoE-derived lipopeptide in high-density lipoprotein MRI contrast agents for enhanced imaging of macrophages in atherosclerosis", *Contrast Media Mol. Imaging*, 2008, 3:233-242, John Wiley & Sons, Ltd.

Amirbekian, V. et al., "Detecting and assessing macrophages in vivo to evaluate atherosclerosis noninvasively using molecular MRI", *PNAS*, Jan. 16, 2007, 104(3):961-966.

Lipinski, M.J. et al., "Macrophage-Specific Lipid-Based Nanoparticles Improve Cardiac Magnetic Resonance Detection and Characterization of Human Atherosclerosis", *JACC: Cardiovascular Imaging*, May 2009, 2(5):637-647, Elsevier Inc.

Dellinger, A. et al., "Functionalization of gadolinium metallofullerenes for detecting atherosclerotic plaque lesions by cardiovascular magnetic resonance", *Journal of Cardiovascular Magnetic Resonance*, 2013, 15(7):1-12, BioMed Central.

Kamat, M. et al., "Hyaluronic Acid Immobilized Magnetic Nanoparticles for Active Targeting and Imaging of Macrophages", *Bioconjugate Chem.*, 2010, 21(11):2128-2135, American Chemical Society.

Lee, G.Y. et al., "Hyaluronic acid nanoparticles for active targeting atherosclerosis", *Biomaterials*, 2015, 53:341-348, Elsevier Ltd.

Beldman, T.J. et al., "Hyaluronan Nanoparticles Selectively Target Plaque-Associated Macrophages and Improve Plaque Stability in Atherosclerosis", *ACS Nano*, May 2, 2017, 11:5785-5799, American Chemical Society.

Taniguchi, R. et al., "Adequately-Sized Nanocarriers Allow Sustained Targeted Drug Delivery to Neointimal Lesions in Rat Arteries", *Mol. Pharmaceutics*, May 16, 2016, 13:2108-2116, American Chemical Society.

Petersen, L.K. et al., "Amphiphilic Nanoparticles Repress Macrophage Atherogenesis: Novel Core/Shell Designs for Scavenger Receptor Targeting and Down-Regulation", *Mol. Pharmaceutics*, Jun. 27, 2014, 11:2815-2824, American Chemical Society.

Li, J.M. et al., "Local arterial nanoparticle delivery of siRNA for NOX2 knockdown to prevent restenosis in an atherosclerotic rat model", *Gene Therapy*, 2010, 17:1279-1287, Macmillan Publishers Limited.

Katsuki, S. et al., "Nanoparticle-Mediated Delivery of Pitavastatin Inhibits Atherosclerotic Plaque Destabilization/Rupture in Mice by Regulating the Recruitment of Inflammatory Monocytes", *Circulation*, 2014, 129:896-906, 2013 American Heart Association, Inc.

Boyer, C. et al., "The design and utility of polymer-stabilized iron-oxide nanoparticles for nanomedicine applications", *NPG Asia Mater.*, Jan. 2010, 2(1):23-30, Tokyo Institute of Technology.

Lin, C. et al., "Positive Contrast Imaging of SPIO Nanoparticles", *Journal of Nanomaterials*, 2012, 2012(734842):9 pages, Hindawi Publishing Corporation.

Kooi, M.E. et al., "Accumulation of Ultrasmall Superparamagnetic Particles of Iron Oxide in Human Atherosclerotic Plaques Can Be Detected by In Vivo Magnetic Resonance Imaging", *Circulation*, May 20, 2003, 107:2453-2458, American Chemical Society.

Corot, C. et al., "Macrophage Imaging in Central Nervous System and in Carotid Atherosclerotic Plaque Using Ultrasmall Superparamagnetic Iron Oxide in Magnetic Resonance Imaging", *Investigative Radiology*, Oct. 2004, 39(10):619-625, Lippincott Williams & Wilkins.

(56) References Cited

OTHER PUBLICATIONS

Gough, P.J. et al., "Analysis of Macrophage Scavenger Receptor (SR-A) Expression in Human Aortic Atherosclerotic Lesions", *Arterioscler Thromb Vasc Biol.*, Mar. 1999, 19:461-471, American Heart Association, Inc.

De Winther, M.P.J. et al., "Macrophage Scavenger Receptor Class A", *Arterioscler Thromb Vasc Biol.*, Feb. 2000, 20:290-297, American Heart Association, Inc.

Rekhter, M.D. et al., "Active Proliferation of Different Cell Types, Including Lymphocytes, in Human Atherosclerotic Plaques", *American Journal of Pathology*, Sep. 1995, 147(3):668-677, American Society for Investigative Pathology.

Thapa, N. et al., "Identification of a peptide ligand recognizing dysfunctional endothelial cells for targeting atherosclerosis", *Journal of Controlled Release*, 2008, 131:27-33, Elsevier B.V.

Segers, F.M.E. et al., "Scavenger Receptor-A1-Targeted Iron Oxide Nanoparticles for In Vivo MRI Detection of Atherosclerotic Lesions", *Arterioscler Thromb Vasc Biol.*, Aug. 2013, 33:1812-1819, American Heart Association, Inc.

Jia, Q. et al., "Gelification: An Effective Measure for Achieving Differently Sized Biocompatible $Fe_3O_4$ Nanocrystals through a Single Preparation Recipe", *J. Am. Chem. Soc.*, Oct. 27, 2011, 133:19512-19523, American Chemical Society.

Li, Z. et al., "One-Pot Reaction to Synthesize Biocompatible Magnetite Nanoparticles", *Advanced Materials*, Apr. 18, 2005, 17(8):1001-1005, Wiley-VCH Verlag GmbH & Co. KGaA, Weinheim.

Butcher, M.J. et al., "Flow Cytometry Analysis of Immune Cells Within Murine Aortas", *Journal of Visualized Experiments*, 2011, pp. 1-6, Journal of Visualized Experiments.

Dunlop, D.J., "Superparamagnetic and Single-Domain Threshold Sizes in Magnetite", *Journal of Geophysical Research*, Apr. 10, 1973, 78(11):1780-1793, the American Geophysical Union.

Kolosnjaj-Tabi, J. et al., "The One Year Fate of Iron Oxide Coated Gold Nanoparticles in Mice", *ACS NANO*, Jul. 13, 2015, 9(8):7925-7939, American Chemical Society.

Qiao, R. et al., "Superparamagnetic iron oxide nanoparticles: from preparations to in vivo MRI applications", *Journal of Materials Chemistry*, 2009, 19:6274-6293, the Royal Society of Chemistry.

Giljohann, D.A. et al., "Oligonucleotide Loading Determines Cellular Uptake of DNA-Modified Gold Nanoparticles", *Nano Letters*, 2007, 7(12):3818-3821, American Chemical Society.

Hurst, S.J. et al., "Maximizing DNA Loading on a Range of Gold Nanoparticle Sizes", *Anal. Chem.*, Dec. 15, 2006, 78(24):8313-8318, American Chemical Society.

Cutler, J.I. et al., "Polyvalent Oligonucleotide Iron Oxide Nanoparticle "Click" Conjugates", *Nano Lett.*, Apr. 14, 2010,10(4):1477-1480.

Tabas, I. et al., "Recent insights into the cellular biology of atherosclerosis", *J. Cell Biol.*, Apr. 13, 2015, 209(1):13-22, The Rockefeller University Press.

Tarbell, J.M., "Shear stress and the endothelial transport barrier", *Cardiovascular Research*, 2010, 87:320-330, the European Society of Cardiology.

Rajendran, P. et al., "The Vascular Endothelium and Human Diseases", *International Journal of Biological Sciences*, 2013, 9(10):1057-1069, Ivyspring International Publisher.

Gu, L. et al., "In Vivo Clearance and Toxicity of Monodisperse Iron Oxide Nanocrystals", *ACSNANO*, 2012, 6(6):4947-4954, American Chemical Society.

Bancos, S. et al., "Evaluating the effect of assay preparation on the uptake of gold nanoparticles by RAW264.7 cells", *Journal of Nanobiotechnology*, 2014, 12(45):1-11, BioMed Central.

Kim, J.A. et al., "Role of cell cycle on the cellular uptake and dilution of nanoparticles in a cell population", *Nature Nanotechnology*, Jan. 2012, 7:62-68, Macmillan Publishers Limited.

Lorenz, J.N. et al., "A simple, nonradioactive method for evaluating single-nephron filtration rate using FITC-insulin", *Am. J. Physiol.*, 1999, 276(*Renal Physiol.* 15):F172-F177, the American Physiological Society.

Geisow, M.J., "Fluorescein Conjugates as Indicators of Subcellular pH", *Experimental Cell Research*, 1984, 150:29-35, Academic Press, Inc., Sweden.

Wu, X.A. et al., "Intracellular Fate of Spherical Nucleic Acid Nanoparticle Conjugates", *Journal of the American Chemical Society*, May 19, 2014, 136:7726-7733, American Chemical Society.

Choi, C.H.J. et al., "Mechanism for the endocytosis of spherical nucleic acid nanoparticle conjugates", *PNAS*, May 7, 2013, 110(19):7625-7630.

Verma, A. et al., "Analysis of the Fc Gamma Receptor-Dependent Component of Neutralization Measured by Anthrax Toxin Neutralization Assays", *Clinical and Vaccine Immunology*, Oct. 2009, 16(10):1405-1412, American Society for Microbiology.

Dobrovolskaia, M.A. et al., "Immunological properties of engineered nanomaterials", *nature nanotechnology*, Aug. 2007, 2:469-478, Nature Publishing Group.

Khalil, I.A. et al., "Uptake Pathways and Subsequent Intracellular Trafficking in Nonviral Gene Delivery", *Pharmacological Reviews*, 2006, 58(1):32-45, The American Society for Pharmacology and Experimental Therapeutics, U.S.A.

Luo, Y. et al., "Phagocytic efficacy of macrophage-like cells as a function of cell cycle and Fcy receptors (FcγR) and complement receptor (CR)3 expression", *Clinical and Experimental Immunology*, 2006, 145:380-387, British Society for Immunology.

Herter, S. et al., "Glycoengineering of Therapeutic Antibodies Enhances Monocyte/Macrophage-Mediated Phagocytosis and Cytotoxicity", *The Journal of Immunology*, 2014, 192:2252-2260, The American Association of Immunologists, Inc., Rockville, Maryland.

Mayor, S. et al., "Pathways of clathrin-independent endocytosis", *Nature Reviews*, Aug. 2007, 8:603-612, Nature Publishing Group.

Oh, P. et al., "Dynamin at the Neck of Caveolae Mediates Their Budding to Form Transport Vesicles by GTP-driven Fission from the Plasma Membrane of Endothelium", *The Journal of Cell Biology*, Apr. 6, 1998, 141(1):101-114, The Rockefeller University Press.

Parton, R.G. et al., "The multiple faces of caveolae", *Nature Reviews*, Mar. 2007, 8:185-194, Nature Publishing Group.

Mellman, I., "Endocytosis and Molecular Sorting", *Annu. Rev. Cell Dev. Biol.*, 1996, 12:575-625, Annual Reviews, Inc.

Hopkins, C.R. et al., "Internalization and Processing of Transferrin and the Transferrin Receptor in Human Carcinoma A431 Cells", *The Journal of Cell Biology*, Aug. 1983, 97:508-521, The Rockefeller University Press.

He, K. et al., "Internalization of the TGF-β type I receptor into caveolin-1 and EEA1 double-positive early endosomes", *Cell Research*, 2015, 25:738-752, IBCB, SIBS, CAS.

Ganley, I.G. et al., "Rab9 GTPase Regulates Late Endosome Size and Requires Effector Interaction for Its Stability", *Molecular Biology of the Cell*, Dec. 2004, 15:5420-5430, The American Society for Cell Biology.

Nielsen, E. et al., "Rab5 regulates motility of early endosomes on microtubules", *Nature Cell Biology*, Oct. 1999, 1:376-382.

Barbero, P. et al., "Visualization of Rab9-mediated vesicle transport from endosomes to the trans-Golgi in living cells", *The Journal of Cell Biology*, Feb. 4, 2002, 156(3):511-518, The Rockefeller University Press.

Carlsson, S.R. et al., "Structure of Human Lysosomal Membrane Glycoprotein 1", *The Journal of Biological Chemistry*, Dec. 5, 1989, 264(34):20526-20531, The American Society for Biochemistry and Molecular Biology, Inc., U.S.A.

Doherty, G.J. et al., "Mechanisms of Endocytosis", *Annu. Rev. Biochem.*, 2009, 78:857-902, Annual Reviews.

Xiao, K. et al., "The effect of surface charge on in vivo biodistribution of PEG-oligocholic acid based micellar nanoparticles", *Biomaterials*, 2011, 32:3435-3446, Elsevier Ltd.

Chinen, A.B. et al., "Relationships between Poly(ethylene glycol) Modifications on RNA-Spherical Nucleic Acid Conjugates and Cellular Uptake and Circulation Time", *Bioconjugate Chemistry*, Oct. 20, 2016, 27:2715-2721, American Chemical Society.

Arami, H. et al., "In vivo delivery, pharmacokinetics, biodistribution, and toxicity or iron oxide nanoparticles", *Chem. Soc. Rev.*, 2015, 44:8576-8607, The Royal Society of Chemistry.

(56) References Cited

OTHER PUBLICATIONS

Choi, H.S. et al., "Renal clearance of quantum dots", *Nature Biotechnology*, Oct. 2007, 25(10)1165-1170, Nature Publishing Group.

Zuckerman, J.E. et al., "Polycation-siRNA nanoparticles can disassemble at the kidney glomerular basement membrane", *PNAS*, Feb. 21, 2012, 109(8):3137-3142.

Choi, C.H.J. et al., "Targeting kidney mesangium by nanoparticles of defined size", *PNAS*, Apr. 19, 2011, 108(16):6656-6661.

Kimura, R.H. et al., "Engineered Knottin Peptides: A New Class of Agents for Imaging Integrin Expression in Living Subjects", *Cancer Res*, 2009, 69(6):2435-2442, American Association for Cancer Research.

Kimura, R.H. et al., "A Dual-Labeled Knottin Peptide for PET and Near-Infrared Fluorescence Imaging of Integrin Expression in Living Subjects", *Bioconjugate Chem.*, 2010, 21:436-444, American Chemical Society.

Knolle, P.A. et al., "Control of immune responses by scavenger liver endothelial cells", *Swiss Med Wkly*, 2003, 133:501-506.

Steffan, A. et al., "Phagocytosis, An Unrecognized Property of Murine Endothelial Liver Cells", *Hepatology*, 1986, 6(5):830-836, The American Association for the Study of Liver Diseases, U.S.A.

Shiratori, Y. et al., "Quantification of Sinusoidal Cell Function in Vivo", *Seminars in Liver Disease*, 1992, 13(1):1-3, Thieme Medical Publishers, Inc. New York, NY.

Elvevold, K. et al., "The liver sinusoidal endothelial cell: a cell type of controversial and confusing identity", *Am J Physiol Gastroinest Liver Physiol*, 2008, 294:G391-G400, the American Physiological Society.

Smedsrød, B., "Clearance function of scavenger endothelial cells", *Comparative Hepatology*, 2004, 3(Suppl I)S22:1-10, BioMed Central.

Tsoi, K.M. et al., "Mechanism of hard-nanomaterial clearance by the liver", *Nature Materials*, Nov. 2016, 15:1212-1221, Macmillan Publishers Limited.

Moghadasian, M.H. et al., "Pathophysiology of apolipoprotein E deficiency in mice: relevance to apo E-related disorders in humans", *FASEB J.*, 2001, 15:2623-2630, FASEB.

Schierwagen, R. et al., "Seven weeks of Western diet in apolipoprotein-E-deficient mice induce metabolic syndrome and non-alcoholic steatohepatitis with liver fibrosis", *Scientific Reports*, Aug. 11, 2015, 5(12931):1-14.

Cole, A.J. et al., "Magnetic brain tumor targeting and biodistribution of long-circulating PEG-modified, cross-linked starch-coated iron oxide nanoparticles", *Biomaterials*, 2011, 32:6291-6301, Elsevier Ltd.

* cited by examiner

| Sample | Hydrodynamic diameter (nm) | | ζ potential (mV) |
|---|---|---|---|
| | in H$_2$O | In DMEM+10 % FBS | |
| PEG-SPION | 40.9±3.1 | 60.6±7.7 | -12.16±1.41 |
| DNA-SPION | 55.8±1.7 | 74.7±4.4 | -25.16±0.78 |

1. PEG-SPION
2. DNA-SPION

PEG-SPIONs

MATERIALS AND METHODS FOR EFFECTIVE IN VIVO DELIVERY OF DNA NANOSTRUCTURES TO ATHEROSCLEROTIC PLAQUES

CROSS-REFERENCE TO RELATED APPLICATION

This application claims the benefit of U.S. Provisional Application Ser. No. 62/550,995, filed Aug. 28, 2017, the disclosure of which is hereby incorporated by reference in its entirety, including all figures, tables and drawings.

BACKGROUND OF THE INVENTION

Cardiovascular diseases (CVD) are the leading cause of death globally, causing 17.3 million deaths per year (1). Initially triggered by chronic inflammation of the endothelium, atherosclerosis is characterized by persistent inflammation and accumulation of lipid-rich plaques or lesions in arterial walls and is the major cause of CVD (2). The hallmark feature of atherosclerosis is the development of atheromatous plaques or lesions characterized by the retention of lipids in the artery wall and infiltration of leukocytes (3). As the most populous cell type in the plaque, monocyte-derived macrophages readily internalize lipids and become foam cells (4). Macrophages also contriubute to the rupture of plaques by digesting extracellular matrix, leading to stroke and myocardial infarction (5). However, because progression of atherosclerosis is gradual and asymptomatic (6), detection of atherosclerotic plaques at the early stage and accurate identification of inflammatory cells that promote atherosclerosis necessitate the development of advanced technologies for detecting plaques at higher specificity and sensitivity (7). The indolent process of atherosclerosis usually does not cause clinical symptoms for more than half of the patients who die of coronary heart diseases (5). Atherosclerosis underpins many cardiovascular diseases with high mortality rates globally, such as stroke and ischemic heart disease. Due to the slow and asymptomatic progression of atherosclerosis, an ongoing clinical challenge is to image and treat atherosclerotic plaques at the earliest possible stage. Despite advances in drug development and stent design in angioplasty procedure, substantial residual risk still remains. Effective delivery of therapeutic and/or contrast agents to the plaques in vivo is crucial.

Currently it is challenging to accurately identify at-risk patients, as conventional imaging tools can only determine the degree of artery stenosis but not to detect early lesions or analyze plaque size, composition, activity or overall disease burden. Most current noninvasive cardiovascular imaging methods, such as positron emission tomography (PET), single-photo emission computed tomography (SPECT) and X-ray angiography rely on radiation exposure to generate photos and is associated with an increased risk of cancer (8).

Recently, high-resolution MM provides characterizations of pathologic plaque components in an accurate and noninvasive manner (9), and hence is regarded as an optimal technique to diagnose and monitoring therapeutic effects of atherosclerosis. The development of MRI technique, however, needs the involvement of appropriate contrast imaging agents, some of which are based on superparamagnetic iron oxide nanoparticles (SPIONs).

Engineered bionanomaterials are now under active investigation for treating and diagnosing atherosclerosis. They not only enhance the delivery of therapeutic and contrast agents to the plaque, but also enable their delivery to specific tissues and cells of the plaque (10). Nanoparticles are considered to be optimal imaging probes mainly due to their favorable nanosize-dependent properties and feasibility in surface modification (5). Bionanomaterials are promising delivery carriers due to their natural ability to accumulate inside plaques upon intravenous (i.v.) injection. Endogenous high-density lipoproteins, a type of lipid-based nanoparticle (NP) with anti-inflammaotry and anti-oxidative properties, are common carriers of therapeutic and contrast moelcules to atherosclerotic plaques (11); circulating lipoproteins can penetrate the arterial wall and accumulate in the sub-endothelial proteoglycan-rich layer within the lamina (12). Peptides and antibodies, when conjugated to the surface of NPs as targeting ligands, can facilitate the delivery of NPs to specific components of the plaque, such as the activated endothelium (13-15), vascular smooth muscle cells (16), collagen (17-18), elastin (19), fibronectin (20), and macrophages (21-24). Recent studies showcased the application of sugar-based bionanomaterials, such as hyaluronic acid-based NPs (25-27) and amphiphilic polymeric NPs containing mucic acid cores (28-30) for targeting the plaque, mitigating inflammation, and attenuating the proliferation of plaque macrophages. With regard to bionanomaterials containing nucleic acids, the existing literature featured the encapsulation of nucleic acids (e.g., siRNA (31), microRNA (32) or DNA plasmid (33) as genetic cargoes of the NPs for promoting their delivery to the plaque and regulating the expression of genes linked to atherogenesis.

SPIONs are preferred MRI contrast agents, not only because they can achieve longer circulation time than other contrast agents such as gadolinium chelates in vivo (34), but also because they can generate reliable visualization with increase of contrast-to-noise ratio (35).

Traditional MRI contrast agents, such as ferumoxtra-10, an ultrasmall superparamagnetic iron oxide nanoparticle (USPIO), visualize atherosclerotic plaques in a "passive targeting" manner and end up in lymph node macrophages after long circulation time (36-37).

To achieve specific targeting to atherosclerotic plaques, various targeting ligands have been incorporated, including vascular cell adhesion molecule-1 (VCAM-1) and P-selectin expressed in vascular inflammation and activated platelet thrombosis (13-14), and profilin-1 for targeting vascular smooth muscle cells (VSMCs) (16). Recently, macrophages have become of interest in targeting due to their preponderant proliferative existence in atherosclerotic plaques (38-40). For example, apolipoprotein-derived peptides (21, 41) or monoclonal antibodies (22), antibodies such as anti-CD36 (23-24), and peptide (42) have been used to target macrophage scavenger receptors. In these studies, in vivo MM images were obtained at 24 h or longer time periods post injection, and the clearance of nanoparticles took even longer time periods. For clinical applications, more rapid targeting and clearance of MRI contrast agents are needed.

For imaging atherosclerotic plaques, commercially available nanoparticles, such as Ferumoxytol and Ferumoxtra-10, are used, but they do not contain DNA.

To achieve targeted delivery of therapuetic agents to atherosclerotic plaques, currently available delivery vehicles often entail the use of peptides, lipid-based proteins, and sugars for targeting certain components of the plaque.

For example, available methods of targeting atherosclerosis plaques with nanoparticles mostly aim at targeting either (1) vascular cell adhesion molecule-1 (VCAM-1) or P-selectin at the inflammed vascular endothelium, (2) non-cellular components such as collegen and fibrin, or (3)

immune cells such as macrophages. Given their abundance in atherosclerotic plaques and their pivotal role in the development of atherosclerosis, macrophages are considered the most attractive targets. Among the available biomolecules for targeting macrophages, peptides, sugars, and lipoproteins are common and often displayed on the surface of nanoparticles.

Reported preclinical applications of bionanomaterials to target atherosclerotic plaques typically use peptides, proteins, lipids, or sugars. For those that contain nucleic acids, the nucleic acids only serve as the payload to regulate genes in the plaque instead of targeting ligands of the plaque components.

No clinically approved nanoparticle-based therapies are currently available for treating atherosclerosis. One of the critical problems that remain in the clinical application is a lack of high accuracy, noninvasive methods for diagnosis and prognosis of atherosclerosis.

Magnetic resonance imaging, as one of the most promising methods, mainly uses SPIONs as contrast agents for enhanced spatial resolution and atherosclerotic lesions. However, few of the nanomaterials have been approved in clinical trials for imaging atherosclerosis due to the lack of specificity, long waiting time and slow clearance rate.

Therefore, nanoparticle-based methods for high accuracy, noninvasive diagnosis and prognosis of atherosclerosis and specific and efficient delivery of therapeutics to atherosclerotic plaques is needed.

BRIEF SUMMARY OF THE INVENTION

Provided herein are materials and methods for generating and using nanoparticle-cored spherical nucleic acids (DNA-NPs). The DNA-NPs of the invention can comprise at least one therapeutic agent. The DNA-NPs of the invention can be superparamagnetic nanoparticle (SPN)-cored spherical nucleic acids (DNA-SPNs). Further, the DNA-SNPs of the invention can be superparamagnetic iron oxide nanoparticle (SPION)-cored spherical nucleic acids (DNA-SPIONs). The DNA-SPIONs of the invention are efficient imaging agents to selectively target and treat atherosclerotic lesions in subjects suffering from or suspected to suffer from atherosclerotic disease.

The DNA-NPs of the subject invention are surface engrafted with DNA oligonucleotides. If the nanoparticle core contains contrast molecules, such as iron oxide or gadolinium ions, the DNA-NPs can be used as in vivo imaging agents of plaques, e.g. as MRI contrast agents. If the core is loaded with anti-inflammatory molecules such as statins or cytokines such as interleukin IL-10, the DNA-NPs can be used as in vivo therapeutic agents for atherosclerosis.

In specific preferred embodiments, the DNA-SPIONs contain a superparamagnetic iron oxide nanoparticle core, a polymeric spacer layer, and an outer DNA oligonucleotide shell. However, the core can generally be replaced by other contrast agents or therapeutic molecules.

Advantageously, when systemically injected, the DNA-SPIONs accumulate rapidly inside the atherosclerotic plaques as demonstrated in Apoprotein E knockout mice. For example, the DNA-SPIONs of the subject invention accumulated in aortic lesions of ApoE−/− mice rapidly, i.e., in as short as 2 hours post-injection, and abundantly, i.e., around 60% of the injected dose per gram of tissue. Inside the plaques, the DNA-coated nanoparticles localize in close vicinity to intralesion macrophages and are more likely to internalize into M2 macrophages than M1 macrophages, endothelial cells, and dendritic cells. The DNA-SPIONs of the subject invention remain inside the plaque for up to 24 hours post-injection. Taken together, DNA-SPIONs of the subejct invention can be useful carriers of therapeutic and contrast agents to atherosclerotic plaques.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 511 shows TEM images of RAW 264.7 cells exposed to DNA-SPIONs.

FIG. 20A shows ex vivo near-infrared fluorescence (NIRF) imaging of the heart and aorta excised from ApoE$^{-/-}$ mice 0.5 h, 2 h and 24 h post-injection of Cy5.5-PEG-SPIONs or Cy5.5-DNA-SPIONs. FIG. 20B shows the flow cytometric analysis of endothelial cells collected from the aorta. FIG. 20C shows the flow cytometric analysis of dendritic cells collected from the aorta. FIG. 20D shows the flow cytometric analysis of total macrophages collected from the aorta. FIG. 20E shows the flow cytometric analysis of M2 macrophages collected from the aorta. FIG. 20F shows representative low cytometry histograms of M2 macrophages collected from the aorta. FIG. 20G shows immunofluorescence images of the aortic root 0.5 hours, 2 hours, and 24 hours following injection of ApoE−/− mice with Cy5.5-PEG- and Cy5.5-DNA-SPIONs, with the artic root stained for plaque macrophages (green) and elastic lamina (blue).

FIG. 22A shows the percentage of Cy5.5-positive cells in the liver. FIG. 22B shows a representative histogram of endothelial cells in the liver. FIG. 22C shows the percentage of Cy5.5-positive cells in the spleen. FIG. 22D shows a representative histogram of total macrophages in the spleen. FIG. 22E shows a representative histogram of dendritic cells in the spleen. FIG. 22F shows the percentage of Cy5.5-positive cells in the lung.

BRIEF DESCRIPTION OF THE SEQUENCES

Figure 1A:
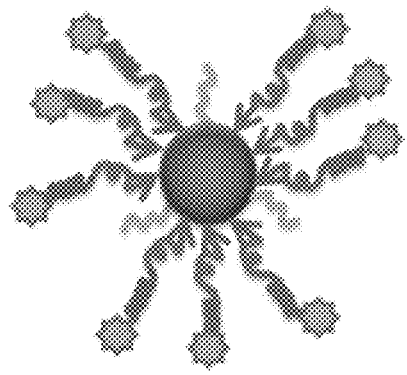
FIG. 1A shows a schematic drawing of a DNA-coated superparamagnetic iron oxide nanoparticle (DNA-SPIONs) that is fluorescently labeled. Single stranded oligonucleotides (ssDNAs), with or without fluorescent tags, are coupled to the poly(ethylene glycol) (PEG) molecules on the surface of SPIONs.
Figure 1A:
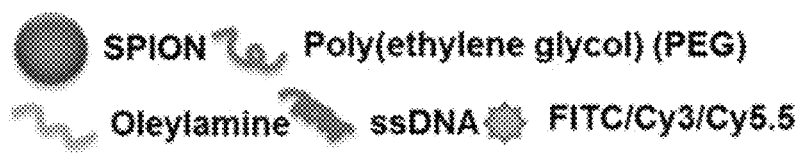

SEQ ID NO: 1 shows the DNA sequence of an oligonucleotide associated with DNA-SPIONs SEQ ID NO: 2 shows the DNA sequence of an oligonucleotide associated with FITC-DNA-SPIONs SEQ ID NO: 3 shows the DNA sequence of an oligonucleotide associated with Cy3-DNA-SPIONs SEQ ID NO: 4 shows the DNA sequence of an oligonucleotide associated with Cy5.5-DNA-SPIONs

DETAILED DISCLOSURE OF THE INVENTION

Provided herein are materials and methods for generating and using nanoparticle-cored spherical nucleic acids (DNA-NPs), which DNA-NPs can comprise at least one therapeutic agent. The DNA-NPs of the invention can be superparamagnetic nanoparticle (SPN)-cored spherical nucleic acids (DNA-SPNs). Furthermore, the DNA-SNPs of the invention can be superparamagnetic iron oxide nanoparticle (SPION)-cored spherical nucleic acids, i.e. DNA-SPIONs, that can be used as efficient imaging and therapeutic agents to selectively target atherosclerotic lesions in subjects suffering from or suspected to suffer from atherosclerotic disease. The nanoparticles of the subject invention display a coating of DNA oligonucleotides on their surface and preferentially accumulate inside atherosclerotic plaques or lesions compared to nanoparticles devoid of the DNA coating. The DNA-NPs, DNA-SPNs, and/or DNA-SPIONs of the subject invention can rapidly enter a variety of cell types without the aid of transfection agents.

Further provided are materials and methods for generating and using DNA-NPs, DNA-SPNs, and/or DNA-SPIONs as therapeutic targeting agents for the targeted delivery of therapeutics to atherosclerotic lesions in patients suffering from or suspected to suffer from atherosclerotic disease.

In specific embodiments, the subject invention provides methods for targeting DNA-NPs, DNA-SPNs, and/or DNA-SPIONs to macrophages present in atherosclerotic lesions in blood vessels, wherein the DNA-NPs, DNA-SPNs, and/or DNA-SPIONS of the subject invention are rapidly taken up by macrophages through endocytosis via Class A scavenger receptors (SR-A). Advantageously, the DNA-NPs, DNA-SPNs, and/or DNA-SPIONs of the subject invention accumulate at enhanced rates and amounts in atherosclerotic plaques following, e.g., intravenous (i.v.) injection.

In preferred embodiments, the DNA-NPs, DNA-SPNs, and/or DNA-SPIONs are prepared by covalently attaching DNA oligonucleotides to poly(ethylene glycol) (PEG) molecules present on PEG-NPs, PEG-SPNs, and/or PEG-SPIONs. PEG-NPs, PEG-SPNs, and/or PEG-SPIONs are highly biocompatible, have previously been used for in vivo applications, and have a low binding affinity to SR-A compared to DNA-coated NPs, SPNs, and/or SPIONs.

The PEG-coated SPNs and/or SPIONs of the subject invention are prepared by decomposing iron (III) acetylacetonate with PEG diacid, a PEG strand bearing a carboxyl group at both ends, and oleylamine as chelating agent under reflux. The supermagnetic properties and high saturation magnetization render the PEG-coated SPNs and/or SPIONs attractive T2-weighed magnetic resonance imaging (MRI) contrast agents. Accordingly, methods are provided for the use PEG-SPNs and/or PEG-SPIONs and DNA-SPNs and/or DNA-SPIONs according to the subject invention as MRI contrast agents in T2-weighed MRI imaging.

According to one of the methods of the subject invention, one of the carboxyl groups of the PEG strands of the PEG-SPNs and/or PEG-SPIONs remains chelated to the iron oxide nanoparticle core, while the other carboxyl group allows for subsequent chemical modification. One such chemical modification according to the methods of the subject invention is the covalent linkage of amide-containing DNA oligonucleotides to the carboxy-terminated PEG-SPNs and/or PEG-SPIONs via 1-ethyl-3-[3-dimethylamino)propyl]-carbodiimide/N-hydroxysuccimide (EDS/NHS) chemistry.

In some embodiments, the DNA-SPNs and/or DNA-SPIONs of the subject invention comprise a superparamagnetic core coated with polyethylene glycol (PEG) and oleylamine and amine-modified single-stranded DNA oligonucleotides covalently attached to the polyethylene glycol chains.

In preferred embodiments, the PEG chains comprise from a low of 10 PEG units to a high of 5000 PEG units. For example, the PEG chains can comprise from about 15 units to about 4900 units; from about 20 units to about 4800 units; from about 25 units to about 4700 units; from about 30 units to about 4600 units; from about 50 units to about 4500 units; from about 100 units to about 4200 units; from about 150 units to about 4000 units; from about 200 units to about 3500 units; from about 250 units to about 3300 units; from about 300 units to about 3000 units; from about 350 units to about 2800 units; from about 400 units to about 2600 units; from about 450 units to about 2400 units; from about 500 units to about 2200 units; from about 550 units to about 2100 units; from about 600 units to about 2000 units from about 650 units to about 2100 units; from about 700 units to about 2000 units; from about 750 units to about 1900 units; from about 800 units to about 1800 units; from about 850 units to about 1700 units; from about 900 units to about 1600 units; from about 950 units to about 1500 units; from about 1000 to about 1400 units; from about 1200 to about 1300 units.

In preferred embodiments, the oligonucleotides attached to NPs, SPNs, and/or SPIONs of the subject invention are single-stranded oligonucleotides. In other embodiments, the oligonucleotides attached to SPIONs of the subject invention are double-stranded oligonucleotides.

In other preferred embodiments, the oligonucleotides are covalently linked to the surface of NPs, SPNs, and/or SPIONs. Any method providing covalent linkage of oligonucleotides can be used to practice the methods of the subject invention and such methods are included in the practice of the subject invention.

In some embodiments, the oligonucleotides are bound to the NP, SPN and/or SPION through a 5' linkage. In other embodiments, the oligonucleotides are bound to the NP, SPN and/or SPION through a 3' linkage.

In preferred embodiments, the covalent linkage is through linkage of amine-modified oligonucleotide attachment to PEG chains. In other embodiments, the covalent linkage is through thiol groups at the 3'end of the oligonucleotides.

In some embodiments, one or more additional oligonucleotides are attached to a DNA-NP, DNA-SPN and/or DNA-SPION by hybridization to the oligonucleotides covalently attached to the NPs, SNPs and/or SPIONs. Advantageously, larger and more complex DNA oligonucleotides can be attached to PEG-NPs, PEG-SPNs, and/or PEG-SPIONs according to the methods of the subject invention to generate DNA-NPs, DNA-SPNs, and/or DNA-SPIONS with properties desirable for a specific clinical intervention and/or specific clinical diagnosis method.

In some embodiments, the oligonucleotides consist of exclusively thymidine nucleotides. In other embodiments, the oligonucleotides comprise repeat sequences of thymidine nucleotides with interspersed non-thymidine nucleotides. The interspersed non-thymidine nucleotides can be adenosine, guanosine or cytosine nucleotides or any of the variety of modified nucleotides known in the art. The repeat sequences of thymidine nucleotides can range in length from a low of about 5 nucleotides to a high of about 200 nucleotides.

For example, the oligonucleotides comprised of thymidine nucleotides can be about 7 nucleotides to a high of 190 nucleotides; from about 10 nucleotides to about 180 nucleotides; from about 15 nucleotides to about 170 nucleotides; from about 20 nucleotides to about 160 nucleotides; from about 30 nucleotides to about 150 nucleotides; from about 40 nucleotides to about 140 nucleotides; from about 50 nucleotides to about 130 nucleotides; from about 55 nucleotides to about 120 nucleotides; from about 60 nucleotides to about 110 nucleotides; from about 65 nucleotides to about 100 nucleotides; from about 70 nucleotides to about 75 nucleotides.

In preferred embodiments, the oligonucleotides are from about 25 to about 100 nucleotides. In further preferred embodiments, the oligonucleotides are from about 25 to about 75 nucleotides. In more preferred embodiments, the oligonucleotides are from about 25 to about 50 nucleotides. In most preferred embodiments, the oligonucleotides about 30 nucleotides in length. In further preferred embodiments, the DNA oligonucleotides of the DNA-NPs, DNA-SPN, and/or DNA-SPIONS contain 30 repeating thymidines. Advantageously, said DNA-SPIONs containing 30 thymidines are characterized by a higher DNA loading on the NP, SPN, and/or SPION surface than DNA sequences of the same length but composed of other types of nucleotides.

In some embodiments, the oligonucleotides comprising interspersed non-thymidine nucleotides comprise between a low of about 5 non-thymidine nucleotides to a high of about 100 non-thymidine nucleotides interspersed between repeat sequences comprised of consecutive thymidine nucleotides.

For example, the interspersed non-thymidine nucleotides can be from about 7 nucleotides to about 190 nucleotides; from about 10 nucleotides to about 180 nucleotides; from about 15 nucleotides to about 170 nucleotides; from about 20 nucleotides to about 160 nucleotides; from about 30 nucleotides to about 150 nucleotides; from about 40 nucleotides to about 140 nucleotides; from about 50 nucleotides to about 130 nucleotides; from about 55 nucleotides to about 120 nucleotides; from about 60 nucleotides to about 110 nucleotides; from about 65 nucleotides to about 100 nucleotides; from about 70 nucleotides to about 75 nucleotides.

In some embodiments, the DNA-NPs, DNA-SPNs, and/or DNA-SPIONs of the subject invention comprise fluorescent marker molecules attached to the oligonucleotides. The fluorescence markers can be attached to either the 5' end or the 3' end of the oligonucleotides depending on which end is attached to the NP, SPN, and/or SPION core. For example, where the 5' ends of the oligonucleotides are covalently linked to the NP, SPN, and/or SPION core or to PEG molecules covalently attached to the NP, SPN, and/or SPION core, the fluorescence marker proteins are attached to the 3' ends of the oligonucleotide. Where the 3' ends of the oligonucleotides are covalently linked to the NP, SPNs, and/or SPION core or to PEG molecules covalently attached to the NP, SPN, and/or SPION core, the fluorescence marker proteins are attached to the 5' ends of the oligonucleotide.

The fluorescent marker can be any fluorescent marker known in the art. For example, the fluorescent marker can be 6-FAM (fluoroscein), Cy3™, TAMRA™, JOE, Cy5™, Cy5.5™, MAX, TET™, Carboxy-X-Rhodamine, TYE™ 563, TYE™ 665, TYE 705, Yakima Yellow®, Hexachlorofluorescein, TEX 615, Alexa Fluor® 488, Alexa Fluor® 532, Alexa Fluor® 546, Alexa Fluor® 594, Alexa Fluor® 647, Alexa Fluor® 660, Alexa Fluor® 750m 5' IRDye® 700, 5'IRDye® 800, 5' IRDye®800CW, ATTO™ 488, ATTO™ 532, ATTO™ 550, ATTO™ 565, ATTO™ Rho101, ATTO™ 590, ATTO™ 633, ATTO™ 647, Rhodamine Green™-X, Rhodamine Red™-X, 5-TAMRA™, WEllRED D2, WellRED D3, WellRED D4, Texas Red®-X, Lightcycler® 640, DY 750, BODIPY FL, EDANS, or IAEDANS.

In preferred embodiments, the fluorescent marker is a fluorescein attached to the 5' end of the oligonucleotide. In further preferred embodiments, the fluorescence marker is a Cy3 attached to the 5' end of the oligonucleotide. In yet other preferred embodiments, the fluorescence marker is a Cy5.5 attached to the 5' end of the oligonucleotide.

The physical diameter of the naked SPION core can be from a low of 10 nm to a high of 200 nm. For example, the size of the SPION core can be from about 12 nm to about 180 nm; from about 15 nm to about 150 nm; from about 20 nm to about 125 nm; from about 25 nm to about 100 nm; from about 30 nm to about 75 nm; from about 35 nm to about 70 nm; from about 40 nm to about 65 nm; from about 45 nm to about 60nm; from about 50 to about 55 nm. In a preferred embodiment, the size of the SPION is from about 15 nm to about 20 nm. In a more preferred embodiment the size of the SPION is about 16 nm.

The hydrodynamic diameter of the PEG-NP, PEG-SPN, and/or PEG-SPION can be from a low of 10 nm to a high of 200 nm. For example, the hydrodynamic diameter of the PEG-NP, PEG-SPN, and/or PEG-SPION can be from about 12 nm to about 180 nm; from about 15 nm to about 150 nm; from about 20 nm to about 125 nm; from about 25 nm to about 100 nm; from about 30 nm to about 75 nm; from about 35 nm to about 70 nm; from about 40 nm to about 65 nm; from about 45 nm to about 60nm; from about 50 to about 55 nm. In a preferred embodiment, the hydrodynamic diameter of the PEG-NP, PEG-SPN, and/or PEG-SPION is from about 40 nm to about 50 nm. In a more preferred embodiment the hydrodynamic diameter of the PEG-NP, PEG-SPN, and/or PEG-SPION is about 41 nm.

The zeta potential of the PEG-SPNs and/or PEG-SPIONs of the subject invention can be from about −50 mV to about −5 mV; from about −45 mV to about −10 mV; from about −40 mV to about −12 mV from about −30 mV to about −13 mV; from about −25 mV to about −14 mV; or from about −20 mV to about −15 mV. In a preferred embodiment, the zeta potential of the PEG-SPIONs is −12 mV.

The hydrodynamic diameter of the DNA-NP, DNA-SPN, and/or DNA-SPION can be from a low of 10 nm to a high of 200 nm. For example, the hydrodynamic diameter of the DNA-NP, DNA-SPN, and/or DNA-SPION can be from about 12 nm to about 180 nm; from about 15 nm to about 150 nm; from about 20 nm to about 125 nm; from about 25 nm to about 100 nm; from about 30 nm to about 75 nm; from about 35 nm to about 70 nm; from about 40 nm to about 65 nm; from about 45 nm to about 60 nm; from about 50 to about 55 nm. In a preferred embodiment, the hydrodynamic diameter of the DNA-NP, DNA-SPN, and/or DNA-SPION is from about 50 nm to about 60 nm. In a more preferred embodiment the hydrodynamic diameter of the DNA-NP, DNA-SPN, and/or DNA-SPION is about 56 nm.

Advantageously, the DNA-NPs, DNA-SPNs, and/or DNA-SPIONs of the subject invention do not increase in hydrodynamic diameter in the presence of proteinaceous solutions by more than 40% compared to a similar NPs, SPNs, and/or SPIONs that lack oligonucleotides, e.g., PEG-NPs, PEG-SPNs, and/or PEG-SPIONs. In preferred embodiments, the DNA-NPs, DNA-SPNs, and/or DNA-SPIONs of the subject invention increase in hydrodynamic diameter by a high of about 40% and a low of about 20%. In some embodiments, the DNA-NPs, DNA-SPNs, and/or DNA-SPIONs increase in hydrodynamic diameter by about 38% to 22%, about 36% to about 24%, about 34% to about 26%, about 32% to about 28% in the presence of proteinaceous solutions. In more preferred embodiments, the DNA-NPs, DNA-SPNs, and/or DNA-SPIONs of the subject invention increase in hydrodynamic diameter by about 27% in the presence of proteinaceous solutions.

In many embodiments of the invention, the weight percentage of PEG to the NP, SPN, and/or SPION core is more than 5:1. In preferred embodiments, the weight percentage of PEG to the NP, SPN, and/or SPION core is more than 7:1. In most preferred embodiments, the weight percentage of PEG to the NP, SPN, and/or SPION core is 9:1.

In many embodiments of the invention, the number of PEG molecules per NP, SPN, and/or SPION can be from a low of about 5 to a high of about 500. For example, the number of PEG molecules per NP, SPN, and/or SPION can be from about 7 to about 480 PEG molecules per NP, SPN, and/or SPION; from about 10 to about 450; from about 15 to about 400; from about 20 to about 380; from about 25 to about 350; from about 30 to about 300; from about 35 to about 280; from about 40 to about 260; from about 45 to about 240 nucleotides. from about 50 to about 220; from about 55 to about 200; from about 60 to about 180; from about 65o about 160; from about 70 to about 140; from about 75 to about 120; from about 80 to about 100 nucleotides In preferred embodiments, the number of PEG molecules per NP, SPN, and/or SPION is between 60 and 100. In more preferred embodiments the number of PEG molecules per NP, SPN, and/or SPION is between 80 and 90.

In many embodiments of the invention, the number of DNA strands per NP, SPN, and/or SPION is between a low of 20 strands and a high of 100 strands.

For example, the number of DNA strands per SPION can be from about 22 to about 95; from about 25 to about 90; from about 30 to about 85; from about 35 to about 80; from about 40 to about 75; from about 45 to about 70; from about 50 to about 65.

In a preferred embodiment, the number of DNA strands per NP, SPN, and/or SPION is from about 55 to about 65. In a more preferred embodiment the number of DNA strands per NP, SPN, and/or SPION is from about 57 to about 63. In the most preferred embodiment, the number of DNA strands per NP, SPN, and/or SPION is about 61.

In some embodiments, the NP, SPN, and/or SPIONs of the subject invention comprise NP, SPN, and/or SPION cores covalently linked to fluorescently-labeled PEG molecules. Further provided are methods for fluorescently-labeling PEG-NPs, PEG-SPNs, and/or PEG-SPIONs by reacting carboxy-terminated PEG-NPs, PEG-SPNs, and/or PEG-SPIONs with amine-functionalized FITC (fluorescein cadaverine). The number of FITC-labeled PEG molecules per NP, SPN, and/or SPION can be from about a low of 5 to about a high of 500 FITC-labeled PEG molecules per NP, SPN, and/or SPION.

For example, the number of FITC-labeled PEG molecules per NP, SPN, and/or SPION can be from about 7 to about 450; from about 10 to about 400; from about 15 to about 350; from about 20 to about 300; from about 30 to about 250; from about 40 to about 200; from about 50 to about 150; from about 55 to about 100; from about 60 to about 80.

In preferred embodiments, the number of FITC-labeled PEG molecules per NP, SPN, and/or SPION is between 60 and 100. In further preferred embodiments the number of FITC-labeled PEG molecules per NP, SPN, and/or SPION is between 80 and 90. In the most preferred embodiments, the number of FITC-labeled PEG molecules per NP, SPN, and/or SPION is about 85.

The zeta potential of the DNA-SPNs and/or DNA-SPIONs of the subject invention can be from about −100 mV to about −5 mV; from about −90 mV to about −10 mV; from about −80 mV to about −12 mV from about −70 mV to about −14 mV; from about −60 mV to about −15 mV; from about −50 mV to about −17 mV; from about −40 mV to about −20 mV. In a preferred embodiment, the zeta potential of the DNA-SPNs and/or DNA-SPIONs is −25 mV.

Also provided herein are methods for generating DNA-SPNs and/or DNA-SPIONs. The methods comprise the steps of synthesizing PEG-SPNs and/or PEG-SPIONs by thermal decomposition of ferric acetylacetonate (Fe(aca)$_3$) with oleylamine and PEG in diphenyl ether and the steps of attaching amine-modified DNA oligonucleotides to PEG-SPNs and/or PEG-SPIONs via EDC/NHS chemistry. Any method suitable to generate DNA-NPs, DNA-SPNs, and/or DNA-SPIONs according to the limitations provided herein can be used to generate the DNA-NPs, DNA-SPNs, and/or DNA-SPIONs of the subject invention.

In some embodiments, the DNA-SPNs and/or DNA-SPIONs of the subject invention comprise a superparamagnetic iron oxide nanoparticle core, oleylamine, polyethylene glycol chains, and amine-modified DNA oligonucleotides but are devoid of other polymerized structures in the layers between the core and DNA oligonucleotides.

Further provided are methods for using DNA-NPs comprising an imaging reagent associated with or incorporated into the DNA-NP, DNA-SPNs and/or DNA-SPIONs of the subject invention as imaging agents for selective and sensitive imaging of atherosclerotic lesions in subjects suffering from or suspected to suffer from atherosclerotic disease. Advantageously, following systemic administration, the DNA-NPs, DNA-SPNs and/or DNA-SPIONs of the subject invention accumulate rapidly in atherosclerotic lesions of subject. In preferred embodiments, the routes of administration include, but are not limited to, intravenous, intraperitoneal, intramuscular, subcutaneous, intracerebral, intraocular, intrarenal, intrahepatic, intra-arterial, intra-carotid, intra-inguinal, intracardial.

In some embodiments, the subject invention provides compositions comprising DNA-NPs, DNA-SPNs and/or DNA-SPIONs of the subject invention and pharmaceutical excipients. In preferred embodiments, the compositions of the subject invention are injected intravenously. In further preferred embodiments, the methods of diagnosing comprise the step of administering to a subject in need of diagnosis a composition comprising DNA-NPs, DNA-SPNs and/or DNA-SPIONs of the subject invention and the step of acquiring at least one image of a body region of the subject suspected to contain atherosclerotic lesions using Magnetic Resonance Imaging (MRI). In further preferred embodiments, the step of acquiring at least one image of a body region using MRI is performed between about 0.1 hours and 100 hours after administration of the composition comprising DNA-NPs, DNA-SPNs and/or DNA-SPIONs.

For example, the step of acquiring at least one image of a body region using MRI is performed from about 90 hours to about 0.2 hours; from about 80 hours to about 0.3 hours; from about 70 hours to about 0.5 hours; from about 60 hours to about 0.7 hours; from about 50 hours to about 1 hour; from about 40 hours to about 1.2 hours; from about 30 hours to about 1.5 hours; from about 20 hours to about 2 hours; from about 15 hours to about 2.5 hours; from about 20 hours to about 3 hours; from about 18 hours to about 4 hours; from about 16 hours to about 5 hours; from about 15 hours to about 6 hours; from about 14 hours to about 7 hours; from about 12 hours to about 8 hours; from about 10 hours to about 9 hours. In preferred embodiments, the at least one MRI image is acquired between about 0.2 hours and about 8 hours. In more preferred embodiments, the at least one MRI image is acquired between about 0.4 hours and about 4 hours. In most preferred embodiments, the at least one MRI image is acquired between about 0.5 hours and about 2 hours after administration of the composition comprising DNA-NPs, DNA-SPNs and/or DNA-SPIONs.

In some embodiments of the subject invention, the method for using DNA-NPs, DNA-SPNs and/or DNA-SPIONs as imaging agents comprises administering to a subject that suffers from or is suspected of suffering from cardiovascular disease.

In some embodiments of the subject invention, the method for using DNA-NPs, DNA-SPNs and/or DNA-SPIONs as imaging agents comprises administering to a subject that suffers from or is suspected of suffering from cerebral atherosclerotic disease.

In other embodiments, the method for using DNA-NPs, DNA-SPNs and/or DNA-SPIONs as imaging agents comprises administering to a subject that suffers from or is suspected of suffering from renal atherosclerotic disease.

Also provided herein are materials and methods for generating and using DNA-SPIONs as therapeutic targeting agents for the targeted delivery of therapeutics to atherosclerotic lesions in patients suffering from or suspected to suffer from atherosclerotic disease.

Advantageously, the DNA-NPs, DNA-SPNs and/or DNA-SPIONS of the subject invention selectively localize to atherosclerotic plaque lesions and are internalized into macrophages present in atherosclerotic plaque lesions. Specifically, the DNA-NPs, DNA-SPNs and/or DNA-SPIONs of the subject invention are internalized into M2 macrophages present in atherosclerotic plaque lesions. Therefore, the DNA-NPs, DNA-SPNs and/or DNA-SPIONs of the subject invention are novel therapeutic targeting agents to specifically target atherosclerotic lesions and macrophages, specifically M2 macrophages, within atherosclerotic lesions. As such, the subject invention provides novel therapies for atherosclerosis of any organ system in an individual suffering from atherosclerotic disease or having atherosclerotic lesions in any vessel of any organ system.

In some embodiments, methods are provided for using DNA-NPs, DNA-SPNs and/or DNA-SPIONs as therapeutic targeting agents for the targeted delivery of therapeutics to atherosclerotic lesions in patients suffering from or suspected to suffer from cardiovascular disease.

In other embodiments, methods are provided for using DNA-NPs, DNA-SPNs and/or DNA-SPIONs as therapeutic targeting agents for the targeted delivery of therapeutics to atherosclerotic lesions in patients suffering from or suspected to suffer from cerebral atherosclerotic disease.

In further embodiments, methods are provided for using DNA-NPs, DNA-SPNs and/or DNA-SPIONs as therapeutic targeting agents for the targeted delivery of therapeutics to atherosclerotic lesions in patients suffering from or suspected to suffer from renal atherosclerotic disease.

In preferred embodiments, the DNA-NPs, DNA-SPNs and/or DNA-SPIONs of the subject invention are loaded with therapeutic molecules or nucleic acids to regulate gene expression in cells present in atherosclerotic lesions. The DNA-NPs, DNA-SPNs and/or DNA-SPIONs of the subject invention can be loaded with any therapeutic agent that is useful in the therapy of atherosclerotic disease.

In some embodiments, the DNA-NPs, DNA-SPNs and/or DNA-SPIONs of the subject invention are loaded with therapeutic agents such that the therapeutic agents are contained within and/or associated with the NP, SPN, and/or SPION core. In other embodiments, the DNA-NPs, DNA-SPNs and/or DNA-SPIONs are loaded with therapeutic agents such that the therapeutic agents are present on the surface of the NP, SPN, and/or SPION core and/or the surface of the DNA-NPs, DNA-SPNs and/or DNA-SPION. In yet other embodiments, the DNA-NPs, DNA-SPNs and/or DNA-SPIONs are loaded with therapeutic agents such that the therapeutic agents are present on or associated with PEG chains present in DNA-NPs, DNA-SPNs and/or DNA-SPIONs. In yet further embodiments, the DNA-SPIONs are loaded with therapeutic agents such that the therapeutic agents are present on and/or associated with the oligonucleotides present on the surface of DNA-NPs, DNA-SPNs and/or DNA-SPIONs.

Agents loaded in and/or on and/or associated with the DNA-NPs, DNA-SPNs and/or DNA-SPIONs of the subject invention can include, but are not limited to, anti-inflammatory molecules, including, but not limited to, statins, cytokines, thrombin inhibitors, inhibitory nucleic acids, including, but not limited to, anti-miRs, immune suppressants, steroids, and/or prostaglandins. For example, the agents loaded in and/or on the DNA-NPs, DNA-SPNs and/or DNA-SPIONs can include, but are not limited to, simvastatin, atorvastatin, interleukin-10 (IL-10), hirulog, anti-miR712, anti-miR12, pioglitazone, didodecyl methotrexate, carmustine, siRNA against chemokine receptor 2 (CCR2), prednisolone, and/or prostacycline, or any combination thereof.

In preferred embodiments, the methods for using DNA-NPs, DNA-SPNs and/or DNA-SPIONs as therapeutic targeting agents for the targeted delivery of therapeutics to atherosclerotic lesions comprise delivering therapeutic molecules to macrophages in atherosclerotic lesions of the patients suffering from or suspected to suffer from atherosclerotic disease.

In more preferred embodiments, the methods for using DNA-NPs, DNA-SPNs and/or DNA-SPIONs for the targeted delivery of therapeutics comprise delivering therapeutic molecules to M2 macrophages in atherosclerotic lesions of the patients suffering from or suspected to suffer from atherosclerotic disease. M2 macrophages are known to be a subgroup of macrophages involved in anti-inflammatory processes and tissue repair.

In most preferred embodiments, the methods for using DNA-NPs, DNA-SPNs and/or DNA-SPIONs for the targeted delivery of therapeutics comprise delivering therapeutic molecules to M2 macrophages through interaction of the DNA-NPs, DNA-SPNs and/or DNA-SPIONS with class A scavenger receptors (SR-A) on M2 macrophages in atherosclerotic lesions of the patients suffering from or suspected to suffer from atherosclerotic disease.

Advantageously, the DNA-NPs, DNA-SPNs and/or DNA-SPIONs of the subject invention can be administered via intravenous injection and localize to macrophages present in atherosclerotic lesions or plaques anywhere in the blood circulation system of a subject, thereby allowing the targeted delivery of one or several therapeutic agents to the macrophages and/or other cells present in the atherosclerotic lesions or plaques anywhere in the blood circulation system of a subject and/or delivering one or several therapeutic agents to the extracellular space between cells present in an atherosclerotic lesions or plaques anywhere in the blood circulation system of a subject.

In some embodiments, the DNA-NPs, DNA-SPNs and/or DNA-SPIONs of the subject invention comprise a single therapeutic agent associated with the SPION core and/or the PEG layer and/or the DNA layer of the DNA-NPs, DNA-SPNs and/or DNA-SPION.

In other embodiments, the DNA-NPs, DNA-SPNs and/or DNA-SPIONs of the subject invention comprise more than one therapeutic agent associated with the SPION core and/or the PEG layer and/or the DNA layer of the DNA-NPs, DNA-SPNs and/or DNA-SPION.

In further embodiments, the DNA-NPs, DNA-SPNs and/or DNA-SPIONs of the subject invention comprise at least one therapeutic agent associated with the SPION core, at least one therapeutic agent associated with the PEG molecules of the PEG layer and/or at least one therapeutic agent associated with the DNA oligonucleotides of the DNA layer of the DNA-NPs, DNA-SPNs and/or DNA-SPION.

In some embodiments, the at least one therapeutic agent is the same therapeutic agent associated with the NP, SPN, and/or SPION core and/or the PEG layer and/or the DNA layer.

In some embodiments, the at least one therapeutic agent is at least one therapeutic agent associated with the NP, SPN, and/or SPION core, at least one different therapeutic agent associated with the PEG layer and/or at least one different therapeutic agent associated with the DNA layer.

In other embodiments, the at least one therapeutic agent can be associated with the NP, SPN, and/or SPION core and the PEG layer or the at least one therapeutic agent can be associated with the NP, SPN, and/or SPION core and the DNA layer or the least one therapeutic agent can be associated with the PEG layer and the DNA layer. Further provided are methods to examine and quantify the extent of cellular uptake mediated by SR-A receptors. Due to the role of SR-A in uptake mechanisms into macrophages and foam cells present in atherosclerotic lesions or plaques, the subject invention provides methods to detect and quantify uptake SR-A-mediated uptake and methods to examine or screen compounds for their ability to inhibit SR-A mediated uptake in macrophages and foam cells in atherosclerotic lesions or plaques.

In some embodiments, the methods provided use DNA-SPIONs of the subject invention to detect and quantify SR-A mediated uptake in cells in vitro and atherosclerotic plaque-associated cells in vivo.

In preferred embodiments, the methods provide the incubation of DNA-SPIONs with macrophages in vitro and/or injection of DNA-NPs, DNA-SPNs and/or DNA-SPIONs into animal in vivo, which animals carry atherosclerotic plaques in their blood circulation system. In some embodiments, compounds suspected to affect SR-A-mediated uptake in macrophages and/or foam cells are added to the cells in vitro or injected into the animals in vivo prior to administration of the DNA-NPs, DNA-SPNs and/or DNA-SPIONs. Advantageously, quantification of DNA-NPs, DNA-SPNs and/or DNA-SPION uptake into cells in vitro or animals in vivo in the presence of the respective compound(s) compared to the cells in vitro or animals in vivo that have not received the compound(s) allows determination and quantification of an effect of the respective compound(s) on SR-A-mediated uptake in the cells in vitro or animals in vivo.

Such compound(s) that inhibit SR-A-mediated uptake into cells in vitro or animals in vivo can then be used to block macrophages and/or foam cells from taking up matter through SR-A receptors and can aid in reducing macrophage and/or foam cell growth and development within an atherosclerotic plaques.

Further, such compound(s) that enhance SR-A-mediated uptake into cells in vitro or animals in vivo can be used either in conjunction with the DNA-NPs, DNA-SPNs and/or DNA-SPIONs of the subject invention or can be used in the context of other therapeutic compounds that target macrophages and/or foam cells in atherosclerotic lesions or plaques to inhibit macrophage survival and/or macrophage proliferation and/or transformation of macrophages into foam cells in atherosclerotic lesions or plaques and/or therapeutic compounds that aid in the stabilization of atherosclerotic lesions or plaques and/or inhibit inflammatory signaling in macrophages and/or foam cells present in atherosclerotic lesions or plaques to prevent plaque rupture and blood vessels occlusion often associated with the rupture of atherosclerotic lesions or plaques.

Materials and Methods

Synthesis of Oligonucleotides.

DNAs were synthesized on an Oligo-800 oligonucleotide synthesizer (Azco Biotech) using standard solid phase synthesis and reagents (Azco Biotech and Glen Research). All DNAs were purified using an Agilent 1260 Inifinity Quaternary LC system with a Microsob C18 column (Agilent Technologies). Table S1 contains detailed sequence information on the conjugates used for DNA-NPs, DNA-SPNs and/or DNA-SPION and their associated oligonucleotide sequences. The Table S1 exemplarily lists only DNA-SPIONs but similar conjugates and oligonucleotides apply to DNA-NPs and DNA-SPNs.

| Type of SPION | Application | Sequence |
| --- | --- | --- |
| DNA-SPION | ICP-MS/ICP-OES, TEM, Prussian blue staining, cytotoxicity study | 5' TTT TTT TTT TTT TTT TTT TTT TTT TTT TTT-NH$_2$ 3' |
| FITC-DNA-SPION | Confocal microscopy/immunofluorescence | 5' FITC-TTT TTT TTT TTT TTT TTT TTT TTT TTT TTT-NH$_2$ 3' |

-continued

| Type of SPION | Application | Sequence |
|---|---|---|
| Cy3-DNA-SPION | Confocal microscopy/fluorescence microscopy | 5' Cy3-TTT TTT TTT TTT TTT TTT TTT TTT TTT-NH$_2$ 3' |
| Cy5.5-DNA-SPION | in vivo NIRF, imaging, flow cytometry, confocal immunofluorescence | 5' Cy5.5-TTT TTT TTT TTT TTT TTT TTT TTT TTT-NH$_2$ 3' |

Synthesis of PEG-NPS, PEG-SPNs and/or PEG-SPIONs and DNA-NPs, DNA-SPNs and/or DNA-SPIONs.

Nanoparticles (NPs) of the subject invention can be natural, incidental or manufactured materials containing particles in an unbound state or as an aggregate or as an agglomerate and for 50% or more of the particles in the number size distribution, one or more external dimensions are in the size range of 1 nm to 1000 nm. The nanoparticles can be made of a variety of materials including, but not limited to, carbon, cellulose, polysaccharides, proteins, peptides, lipids, with lipid-based materials including, but not limited to, phospholipids and poly-lactide-co-glycolide, and metals, with metal-based materials including, but not limited to, silver, gold, platinum, aluminum oxide, and titanium oxide.

PEG-coated SPNs and/or SPIONs (PEG-SPNs, PEG-SPIONs) with functionalized carboxylate groups were synthesized by thermal decomposition of ferric acetylacetonate (Fe(acac)3) with oleylamine and poly(ethylene glycol) diacid 2000 (HOOC-PEG2000-COOH) in diphenyl ether (43) and later purified and lyophilized. HOOC-PEG2000-COOH was synthesized according to literature (44). Amine-modified DNA oligonucleotides were attached to PEG-SPNs and/or PEG-SPIONs via EDC/NHS chemistry. Typically, 5 mg PEG-SPNs or PEG-SPIONs was dissolved in 0.5 mL DMSO and activated with 20 µmol DCC and NHS for 2 h, then 6 nmol amine-modified DNA was added to the mixture under shaking overnight. The DNA-coated SPNs and/or SPIONs (DNA-SPNs and/or DNA-SPIONs) were dialyzed against nanopure water by a centrifugal filter (MWCO: 50000) for three times, and re-suspended in nanopure water. The size and morphology of nanoparticles were examined by transmission electron microscopy (TEM) using a Tecnai™ Spirit electron microscope (FEI).

Magnetization Curve.

The magnetic property of the lyophilized PEG-coated SPNs and/or SPIONs (PEG-SPNs and/or PEG-SPIONs) powder was measured at room temperature by using a vibrating sample magnetometer (VSM, Lakeshore VSM 7400). Magnetization was measured over a range of applied field from −6,000 Oe to 6,000 Oe.

DNA-NPs, DNA-SPNs and/or DNA-SPION associated Oligonucleotide Sequences For ICP-MS and TEM studies, amine-terminated DNA oligonucleotide strands were attached to NPs, SPNs and/or SPIONs (with a core size of 16 nm) that contained carboxylate-terminated poly(ethylene glycol) strands on their surface by EDC/NHS chemistry.

For confocal immunofluorescence studies, the same procedures as for ICP-MS and TEM studies were used except that bifunctional DNA oligonucleotides were used that contained an amine group for conjugation to the carboxylated PEG shell of the NP, SPN and/or SPION at the 3' end and a FITC (fluorescein isothiocyanate) or Cy3 (Cyanine 3) moiety at the 5' end.

For in vivo NIRF imaging, the same procedures as for confocal immunofluorescence studies were used except that the bifunctional DNA oligonucleotides were replaced with bifunctional DNA oligonucleotides that contained an amine group at the 3' end and a Cy5.5 moiety at the 5' end.

Cell Culture and Nanoparticle Treatment.

The cellular uptake of PEG-NPs, PEG-SPNs and/or PEG-SPIONs and DNA-NPs, DNA-SPNs and/or DNA-SPIONs were conducted in three cell lines: AML-12 (mouse hepatocyte), C166 (mouse endothelial), MOVAS (mouse smooth muscle) RAW 264.7 (mouse macrophage) and primary bone marrow derived macrophages (BMDM) and bone marrow derived dendritic cells (BMDC), which were cultured at 37° C. and 5% CO2 in medium and supplements described by ATCC. To measure the extent of cellular uptake by ICP-MS, cells were first seeded in a 24-well plate at proper populations ($10^4$-$10^5$) varied by cell sizes and growth rates. Cells were incubated with 2.5 nM or 5 nM PEG-NPs, PEG-SPNs and/or PEG-SPIONs and DNA-NPs, DNA-SPNs and/or DNA-SPIONs for 24 h. Then nanoparticles were removed. Cells were rinsed with PBS and trypsinized or pipetted down for determination of cell number by counting using a hemacytometer. Cells were centrifuged at 8000 rpm for 5 min to form a pellet for quantification by ICP-MS or imaging by TEM. Uptake kinetics of both SPIONs was conducted in RAW 264.7 cells, which followed the same protocol as mentioned above, with cells incubated at 5 nM in each well and harvested at different time points for ICP-MS analysis.

ICP-MS.

Cell pellets were digested in 0.3 mL of concentrated trace-metal HNO3 at RT overnight. After adding 5 µL of 5 ppm indium (internal standard) and 10 mL 2% HNO3 solution, the Fe content of the resultant solution was measured by ICP-MS after subtracting the background Fe content of untreated cells. Unless otherwise mentioned, repots values represent mean±SE from the average of three independent experiments.

TEM.

Cell pellets were first suspended in 0.3 mL PB solution and pelleted again by centrifugation at 4000 rpm for 10 min. Cells were fixed in 2.5% glutaraldehyde for 2 h at RT, stained by 2% OsO4, followed by rinsing in H2O three times. After gradual dehydration with ethanol and propylene oxide, cell pellets were embedded in Epon 812 resins (Electron Microscopy Sciences). We deposited 70-nm-thick sections on 200-mesh copper grids (Electron Microscopy Sciences) and stained with 4% uranyl acetate (SPI Supplies) and Renylds lead citrate for visualization under a H7700 transmission electron microscope (Hitachi) using beam voltage of 80 kV.

Cytotoxicity Studies.

To evaluate the cytotoxicity PEG-NPs, PEG-SPNs and/or PEG-SPIONs and DNA-NPs, DNA-SPNs and/or DNA-SPIONs, four types of cells (AML-12, C166, MOVAS and RAW 264.7) were plated on a 96 well plate with proper cell densities, e.g., at a density of 105 cells per well 24 hours before the experiment. The cells were then incubated with either PEG-NPs, PEG-SPNs and/or PEG-SPIONs or DNA-NPs, DNA-SPNs and/or DNA-SPIONs over a range of final Fe concentrations (1-500 µg/mL) for 24 h. After that, the cells were washed three times with 1× PBS and incubated in MTT reagent (Cayman Chemical) at 37° C. for 4 h under in a 5% $CO_2$ incubator. After removing the medium, 100 uL of acidified isopropanol (0.04 M HCl in absolute isopropanol) were added into each well with gentle shaking to completely dissolve the dark purple crystals. The absorbance of each well at 570 nm was recorded using a Multiskan™ GO Microplate Spectrophotometer (Thermo Scientific). After normalized to the signals for untreated cells, the relative cytotoxicity of both nanoparticles can be compared. Reported data represented mean±SD from six independent experiments.

Confocal Microscopy and Immunofluorescence. Cells were seeded on a glass slide of 12 mm in diameter (Marienfeld Superior) in 24-well plate (SPL Life Sciences) at $5 \times 10^5$ cells per well 24 h before staining and incubated with 2.5 nM or 5 nM of FITC-PEG-NPs, FITC-PEG-SPNs and/or FITC-PEG-SPIONs or FITC-DNA-NPs, FITC-DNA-SPNs and/or FITC-DNA-SPIONs for different time points. Cells were rinsed with PBS, fixed in 4% paraformaldehyde (PFA) with 1% Triton X-100 (Sigma-Aldrich in PBS for 15 min. Cells were stained with primary antibodies at 5 µg/mL (1% BSA in PBS) overnight at 4° C. After rinses with 0.05% Tween-20 in PBS, cells were stained with a fluorescently labeled secondary antibody at 1 µg/mL (1% BSA in PBS) for 1 h at RT.

For detection of expression of MSR-1, the primary antibody used was rat anti-mouse CD204 (AbD Serotec; MCA1322GA), and the secondary antibody was 488-labeled goat anti-mouse IgG secondary antibody (Thermo Fisher Scientific; R37120). Cells were counterstained with DAPI and imaged with a Nikon C1si confocal laser scanning microscope. The excitation wavelength for DAPI was 405 nm, and the corresponding emission filter was 480/25 nm. The excitation wavelength for FITC was 488 nm, and the corresponding emission filter was 500-530 nm.

For determining the efficiency of gene knockdown, the primary antibodies used included those antibodies against MSR1 (rat anti-mouse CD204 antibody, AbD Serotec; MCA1322GA), CAV1 (caveolin-1 rabbit mAb, Cell Signaling; D46G3), and FLOT1 (flotillin-1 rabbit mAb, Abcam; ab41927). The secondary antibodies included Cyanine 5-labeled goat anti-rat IgG secondary antibody (Thermo Fisher Scientific; A10525) and Cyanine 5-labeled goat anti-rabbit IgG secondary antibody (Thermo Fisher Scientific; A10523). Cells were counterstained with DAPI, and imaged with an Olympus confocal microscope (FV1000 IX81-TIRF). The excitation wavelength for DAPI was 405 nm, and the corresponding emission filter was 440-500 nm. The excitation wavelength for the Cy5 was 635 nm, and the corresponding emission filter was 650-750 nm.

The cells were imaged with a Nikon C1si confocal laser scanning microscope equipped with a spectral imaging detector (Nikon, Japan). The excitation wavelength was 488 nm, and the corresponding emission filter was 495-540 nm. To track the co-localization of NPs, SPNs, and/or SPIONs with cellular proteins, after the cells were incubated with FITC-DNA-NPs, FITC-DNA-SPNs and/or FITC-DNA-SPIONs for different time, the cells were washed, fixed, and permeated with 1% Triton-100 for 10 min. After blocking with 2% BSA in PBS for 1 h, cells were stained with a primary antibody against the protein marker of interest at 5 µg/mL (1% BSA in PBS) overnight at 4° C. After rinses with 0.05% Tween-20 in PBS, cells were stained with a Cy3-labeled secondary antibody [Life Technologies, Cy3 Goat Anti-Rabbit IgG (H+L)] at 1 µg/mL (1% BSA in PBS) for 1 h at RT. The cells were imaged using an Olympus confocal microscope (FV1000 IX81-TIRF). The excitation wavelength for secondary antibody was 543 nm, and the corresponding emission filter was 550-630 nm. The primary antibodies include rabbit against Rab5 (Abcam ab18211), rabbit against Rab 9 (Santa Cruz Biotechnology FL-201), and rabbit against LAMP1 (Abcam ab 24170). To label the MSR1, cells were washed, fixed and permeated, cells were incubated with Rat Anti-Mouse CD204 (AbD Serotec, MCA1322GA) as the primary antibody, then stained with an AlexaFluor 488-labeled secondary antibody (Life Technologies, AlexaFluor 488 Goat Anti-Rat IgG (H+L)). The cells were imaged with a Nikon C1si confocal laser scanning microscope.

Cellular Uptake by Confocal Microscopy.

Seeded in 24-well plate (SPL Life Sciences) with a glass slide of 12 mm in diameter (Marienfeld Superior), RAW 264.7 cells were incubated with 0.3 mL of FITC-labeled PEG-SPIONs or DNA-SPIONs (5 nM in serum-containing DMEM) for various durations of time. The cells were rinsed with PBS, fixed in 4% paraformaldehyde (PFA) in PBS for 15 min, and imaged with a Nikon C1si confocal laser scanning microscope. The excitation wavelength for FITC was 488 nm, and the corresponding emission filter was 500-530 nm. In another experiment, RAW 264.7 cells were treated with FITC-labeled NPs, SPNs, and/or SPIONs for different durations of time, followed by trypsinization, centrifugation to form cell pellets, and imaging by using a UV transilluminator (GeneDireX).Cytotoxicity of Pharmacological Inhibitors.

RAW 264.7 cells were plated on a 96-well plate at a density of 105 cells per well 24 h before the experiment. The cells were incubated with chemical blockers or blocking antibodies in serum-containing DMEM for 24 h at the same concentrations as used in the pharmacological inhibition experiment. After removing the medium and rinsing the cells, the alamarBlue reagent (Invitrogen) was used to test the cell viability according to the manufacturer's instructions by measuring the optical absorbance at 570 nm and 600 nm. Reported data represented mean±SD from six independent experiments.

Chemical and Antibody Blocking Studies.

In 24-well plates, cells were pretreated with 300 µL of OptiMEM that contains different concentrations of chemical blockers and two antibodies per well for 1 h. We added 280 µL DMEM supplemented with 10% fetal bovine serum that contains 75 nM of DNA-NPs, DNA-SPNs and/or DNA-SPIONs to each well, and cells were incubated for another 4 h. To extent of blocking, cells were pelleted and digested for ICP-MS analysis.

siRNA Transfection.

RAW 264.7 cells were seeded in 24-well plate 12 h before transfection. Cells were transfected with the scrambled siRNA control (ON-TARGETplus Non-targeting, Dharmacon), MSR1 siRNA (ON-TARGETplus Msr1 siRNA-SMARTpool, Dharmacon) and CAV1 siRNA (ON-TARGETplus Msr1 siRNA-SMARTpool, Dharmacon) at 200 nM with Lipofectamine® 2000 transfection reagent (Thermofisher Scientific) according to the standard protocol provided by the manufacturer. After 24 h, cells were serum-starved for 24 h followed by treatment with 5.0 nM PEG- SPIONs for 4 h. Two days after transfection, cells were harvested, pelleted and digested for ICP-MS analysis.

Western Blotting for Gene Knockdown Analysis.

RAW 264.7 cells were seeded in 6-well plate 12 h before transfection. Celle were washed three times with ice-cold TBS buffer and homogenized with 0.1 mL ice-chilled RIPA buffer containing 1× protease and phosphatase inhibitor (Thermo Scientific). The homogenate were cleared by centrifugation at 12,000×g for 15 min and the supernatant were kept as protein lysate. The total protein amount was quantified by a Pierce BCA protein assay kit. The lysate with same amount of total protein was transferred to a 0.5 mL microcentrifuge tube, diluted with 4× Laemmi sample buffer (Bio-Rad) containing 10% mercaptoethanol (Sigma-Aldrich). After boiling for 5 min, samples with equal amount of total protein were fractioned by 10-15% precast polyacrylamide gel (Bio-Rad). The intact gel was then transferred to a polyvinylidene difluoride (PVDF) membrane (Bio-Rad) and blocked with 5% non-fat milk (for MSR1 and β-actin) or 5% BSA (for CAV1 in TBST buffer for 1 h. Proteins were treated with primary antibodies against MSR1 (1:500) (Rat Anti-Mouse CD204 antibody, AbD Serotec), CAV1 (1:1000) (Caveolin-1 Rabbit mAb, Cell Signaling), β-actin antibody (1:1000) (ab8227, Abcam) followed by rabbit anti-rat IgG H&L (HRP) (1:1000) (ab6734, Abcam) and goat anti-rabbit IgG H&L (HRP) (1:1000) (Bio-Rad) diluted in TBST containing 5% non-fat milk. The membranes were then treated with Clarity™ Western ECL Substrate (Bio-Rad) and the proteins were visualized with ChemiDoc Touch Imaging System (Bio-Rad).

Animal Experiments, Mice.

Six to eight-week-old ApoE−/− mice were fed with a high-fat diet (Atherogenic diet, MP Biomedicals) for either 6 or 12 weeks to induce early and advanced atherosclerotic lesions, respectively. After the diet period, the mice received an intravenous injection of PEG-NPs, PEG-SPNs and/or PEG-SPIONs and DNA-NPs, DNA-SPNs and/or DNA-SPIONs at a dosage of 5 mg Fe/kg, which were labeled with a fluorescent dye (Cy5.5) when necessary (for NIRF imaging, immunohistochemistry, flow cytometric analysis of heart and aorta). At designated time points post injection, the mice were first anesthetized and sacrificed by cervical dislocation.

Pharmacokinetics and Biodistribution in Mice.

To determine the blood clearance parameters, blood were drawn by cardiac puncture and stored in EDTA-coated tubes (Becton Dickinson). After centrifuge at 1,500×g for 10 min, 200 μL of blood plasma in the supernatant were collected, lysed in 0.5 mL 65% HNO3. For biodistribution study of SPIONs, different organs including brain, heart (lower half part), aorta, lung, liver, spleen and kidney were removed, cut into small pieces, and oxidized in 0.5 mL 65% HNO3 until they were fully dissolved. Blood and organ samples were diluted into 2% HNO3 solution, filtered with 0.2 μm hydrophilic syringe filters before Fe content analysis by inductively coupled plasma optical emission spectrometry (ICP-OES) (Perkin Elmer). Blood and tissues from uninjected ApoE−/− mice were used to account for background Fe content. Reported values are expressed as percent ID per gram of tissue. Error bars indicate 1 SD in each mouse group (n=3). The blood clearance data were fitted by a mono and bi-exponential decay model using Prism Graphpad 6 software. The best fitting model, as concluded from the correlation coefficient, r2, was used for reporting.

In Vivo and Ex Vivo near Infrared Fluorescence Imaging of Mice.

ApoE−/− mice with both early and advanced atherosclerotic lesions received tail-vein injection of Cy5.5-PEG-NPs, Cy5.5-PEG-SPNs and/or Cy5.5-PEG-SPIONs and Cy5.5-DNA-NPs, Cy5.5-DNA-SPNs and/or Cy5.5-DNA-SPIONs at a dosage of 5 mg Fe/kg weight. At 2 h and 24 h post injection, anesthesia was induced by intraperitoneal injection of ketamine combined with xylazine. To acquire in vivo NIRF imaging, signals were collected with Bruker In Vivo Xtreme imaging system (Bruker) using 675 nm excitation and 720 nm emission filters. The mice were then sacrificed and perfused with PBS. Aortas, hearts, livers, spleens, pancreas and kidneys were imaged with the same equipment. Photon counts were used to quantify the fluorescence intensity from each tissue and it was reflected by color-coded scale bar.

Immunohistochemistry of Mice Aortic Roots.

From mice that were injected with Cy5.5-labeled nanoparticles, several samples of upper part of hearts were collected. The samples were frozen in Shandon Cryomatrix Frozen Embedding Medium (Thermo Fisher Scientific) and cut into 10-μm-thick sections. Before staining, they were fixed for 10 min in % paraformaldehyde. After blocking with SEA BLOCK Blocking Buffer (Thermo Fisher Scientific), the aortic root sections were stained with mouse monoclonal [ED1] to CD68 (Abcam, ab31630). After incubation for 2 h and washing with PBS, Alexa Fluor 532-conjugated goat anti-mouse IgG (H+L) cross-adsorbed secondary antibody (Thermo Fisher Scientific, A-11002) was added and incubated for 1 h. The images were acquired using an Olympus confocal microscope (FV1000 IX81-TIRF).

Flow Cytometry.

ApoE−/− mice with advanced atherosclerotic lesions received tail-vein injection of Cy5.5-PEG-NPs, Cy5.5-PEG-SPNs and/or Cy5.5-PEG-SPIONs and CY5.5-DNA-NPs, Cy5.5-DNA-SPNs and/or Cy5.5-DNA-SPIONs at a dosage of 5 mg Fe/kg weight. The mice were killed at both 2 and 24 h post injection (N=3 or 4 per time point for each nanoparticle). Aortas were perfused with phosphate-buffered saline with heparin (100 U/mL), dissected free from adventitia and perivascular adipose tissue and dissociated with enzyme mixtures containing collagenase I (450 U/ml), collagenase XI (125 U/ml), DNase I (60 U/ml) and hyaluronidase (60 U/ml) (Worthington) at 37° C. for 1 hour with gentle shaking. Livers and lungs were first sliced into small pieces and treated similarly. Digested tissues were minced and filtered (70 μm) to get single-cell suspension (45) Spleens were grinded and filtered (70 μm) to get single-cell suspension, treated with RBC lysis buffer for 10 min at room temperature and centrifuged. Pelleted cells were re-suspended in FACS buffer (PBS, 5 mM EDTA, and 1% FBS) for immunostaining and the subsequent flow cytometric analyses. For staining lung, liver and aorta, antibodies used after Fc-block (BioLegend. Cat.101320) include the following three staining panels. (1) CD31 (BioLegend, MEC13.3, Cat.102514). (2) F4/80 (Invitrogen, BM8, Cat. MF48020) and CD301 (Bio-Rad, ER-MP23, Cat. MCA2392A647). (3) MHC Class II (BioLegend, M5/114.15.2, Cat.107616) and CD11c (BioLegend, N418, Cat. 117327). Antibodies for staining splenocytes include the following two staining panels. (1) F4/80 (Invitrogen, BM8, Cat. MF48020) and CD301 (Bio-Rad, ER-MP23, Cat. MCA2392A647). (2) MHC Class II (BioLegend, M5/114.15.2, Cat.107616) and CD11c (BioLegend, N418, Cat. 117327). Samples were fixed in FluoroFix buffer (Biolegend) and stored at 4° C. prior to analysis. Fluorescence was detected using a flow cytometer (BD Biosciences Diva), and the data were analysed using the FlowJO software (Tree Star). Endothelial cells from aorta, liver and lung were identified as CD31+ cells, dendritic cells from all organs were identified MCHII+ and CD11c+ cells, macrophages were identified as F4/80+ cells, and M2 cells were identified as F4/80+ and CD301+ cells.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

EXAMPLE 1

Figure 1B:
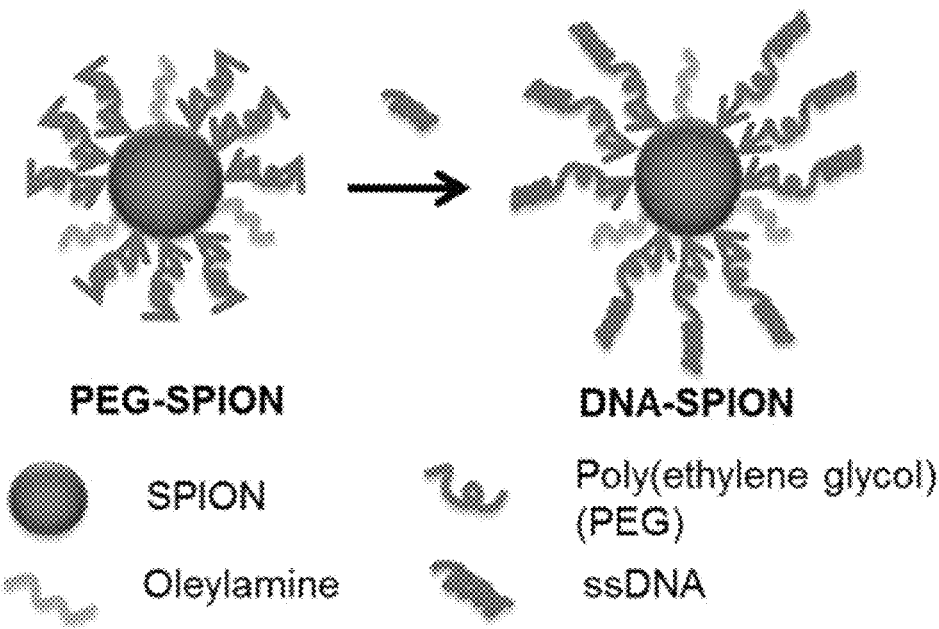
FIG. 1B shows a schematic drawing of the preparation of a DNA-SPION.

Characterizations of PEG-NPs, PEG-SPNs and/or PEG-SPIONs and DNA-NPs, DNA-SPNs and/or DNA-SPIONs Although the core material of NP, SPN, and/or SPION-cored spherical nucleic acids does not affect their biological properties, their biocompatibility is still a great concern when NPs, SPNs, and/or SPIONs are used as in vivo delivery vehicles or imaging agents. Iron oxide nanoparticles were chosen as the model material due to their well-known biocompatibility and superior performances as MRI contrast agents. FIG. 1A shows the composition of fluorescently-labeled DNA-coated SPIONs (DNA-SPIONs), consisting of a SPION core, a dense poly(ethylene glycol) (PEG) layer and DNA conjugation in the outmost layer, which DNA is conjugated to a fluorescent molecule. Before DNA conjugation, the PEG-coated SPIONs (PEG-SPIONs) were synthesized from the high temperature decomposition of iron (III) acetylacetonate with PEG diacid and oleylamine as chelating agents (FIG. 1B, left). To the surface of a SPION core coated with PEG strands that bear carboxylate groups (HOOC-PEG-SPION) at their distal ends, single-stranded amine-terminated DNA oligonucleotides (ssDNA-NH$_2$) were covalently conjugated via EDC/NHS chemistry through the cross-linking of carboxylic acid to amine with catalyst in DMSO (FIG. 1B, right). Fluorescent tags were added to the DNA oligonucleotides (FIG. 1A). For in vitro and in vivo studies, the constituent DNA oligonucleotides of DNA-SPIONs comprised 30 repeating thymidines. This sequence was chosen due to its higher DNA loading onto a nanoparticle surfaces compared to DNA sequences of the same length composed of other types of nucleotides. However, repeating or non-repeating sequences of other types of nucleotides can be used in DNA-SPIONs. DNA-SPIONs of the subject invention are able to enter atherosclerotic plaques and interact with Class A scavenger receptors (SR-A) on cells resident in the atherosclerotic plaques, e.g., endothelial cells, smooth muscle cells and macrophages (FIG. 1C).

Figures 1C, 2A:
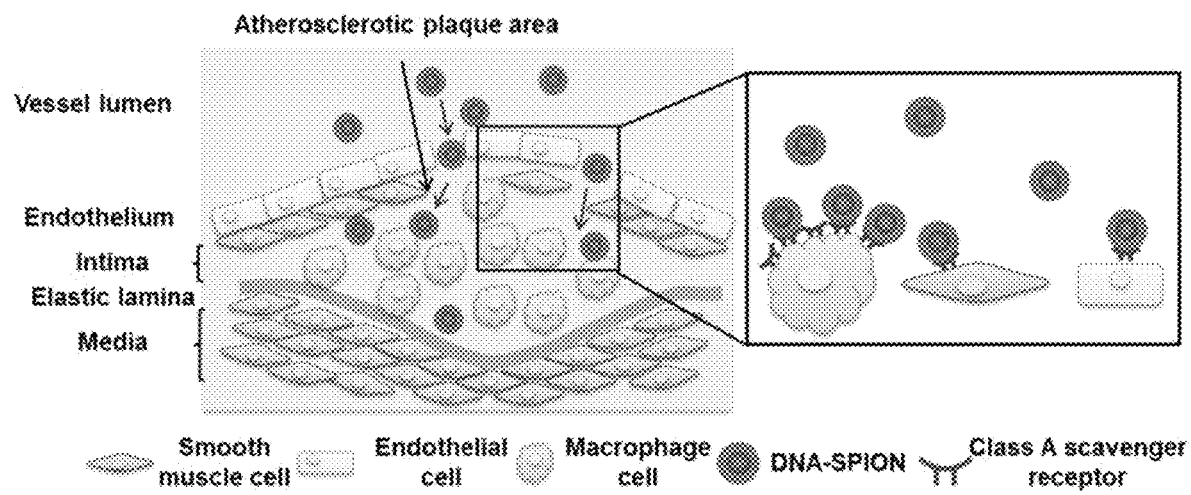
FIG. 1C shows a schematic drawing of DNA-SPIONs entering atherosclerotic plaques and binding to Class A scavenger receptors on macrophages in atherosclerotic plaques.
FIG. 2A shows the hydrodynamic size and charge of DNA-SPIONs incubated with DMEM containing 10% FBS.

Dynamic light scattering (DLS) measurements revealed that the mean hydrodynamic diameter and zeta potential of the as-synthesized PEG-SPIONs were 40.9 nm and −12.1 mV, respectively (FIG. 2A). The PEG-SPIONs were stable in serum-containing cell culture medium. The hydrodynamic diameter of PEG-SPIONs increased to 60.6 nm upon incubation in DMEM containing 10% fetal bovine serum (FBS) for 24 h at 37° C., which mimics the in vivo environment (FIG. 2A). By TEM imaging, the diameter of the Fe3O4 core of PEG- and DNA-SPIONs was determined to be ~16 nm (FIG. 2B), which is below the "critical size" of magnetic iron oxides (46); thus, the PEG- and DNA-SPIONs demonstrated superparamagnetic properties.

Figure 2B:
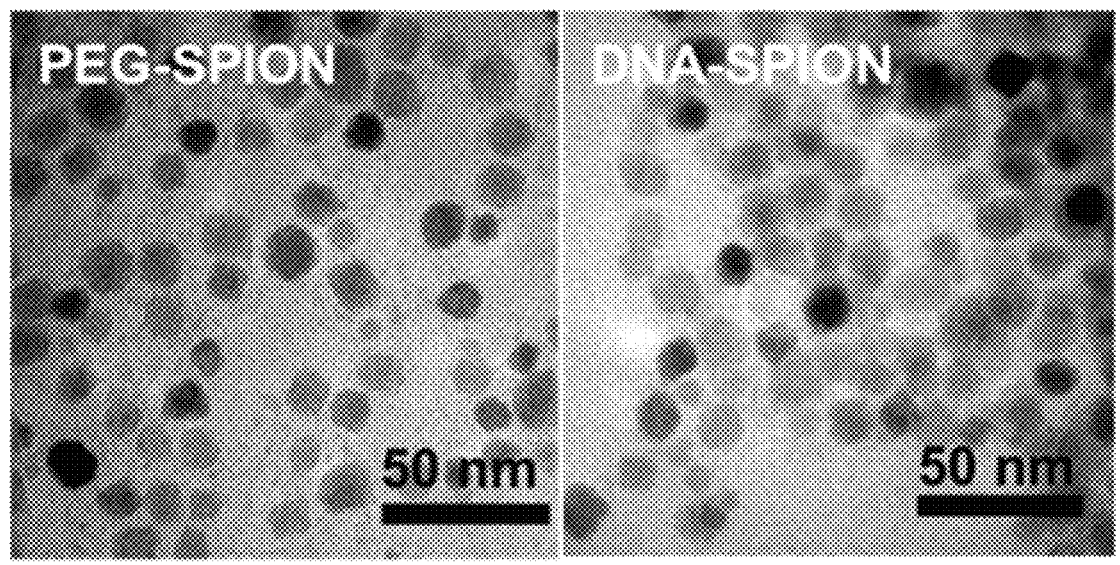
FIG. 2B shows Transmission Electron Microscopy (TEM) images of PEG-SPIONs and DNA-SPIONs.
Figure 2C:
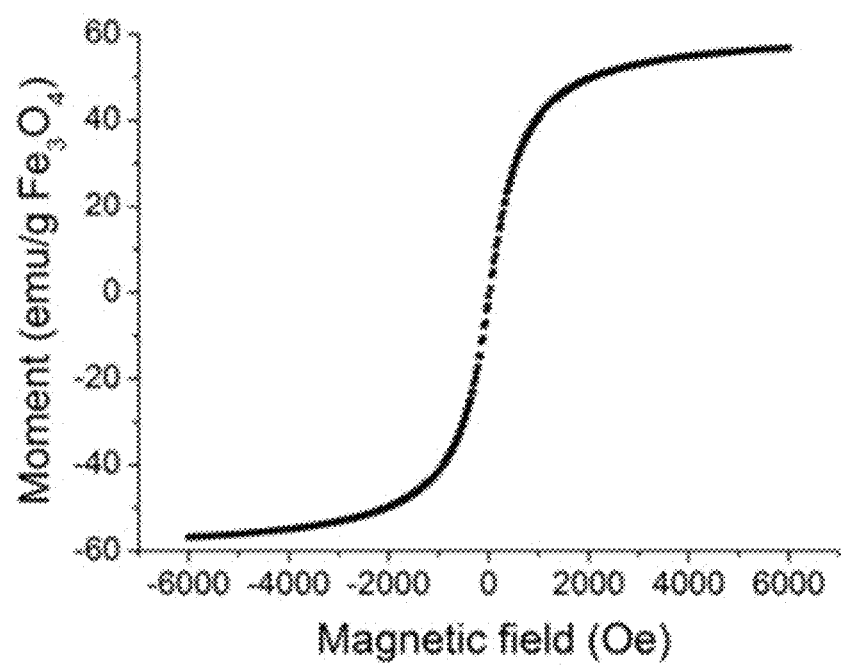
FIG. 2C shows a magnetization curve of PEG-SPIONs.
Figure 2D:
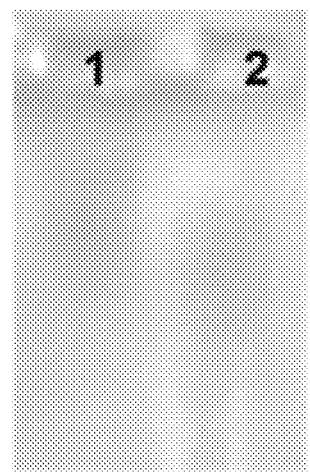
FIG. 2D shows an agarose gel electrophoresis of PEG-SPIONs and DNA-SPIONs.
Figure 2E:
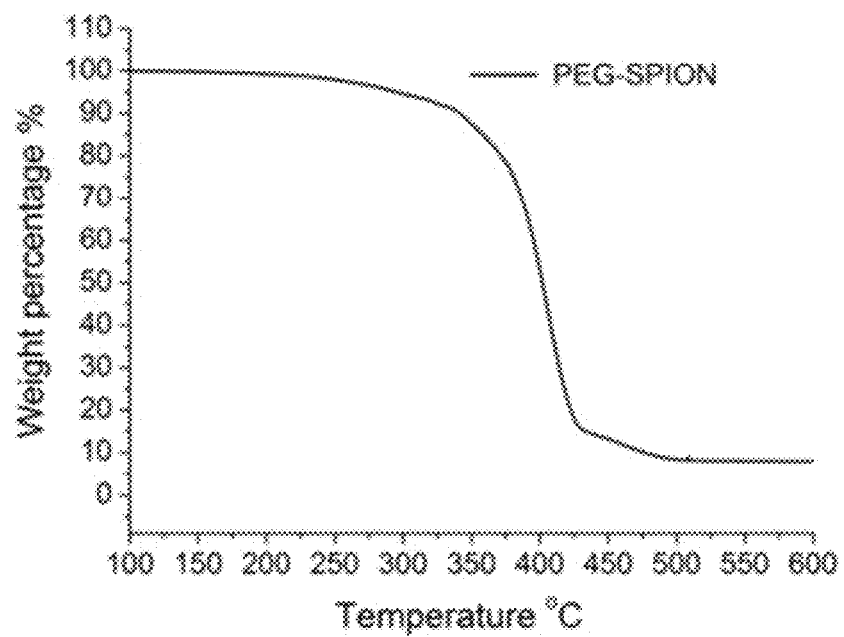
FIG. 2E shows a Thermogravimetric Analyzer (TGA) curve for PEG-SPIONs.

Due to the DNA layer on the surface, DNA-SPIONs showed more negative zeta potential, larger hydrodynamic size and higher electrophoretic mobility compared to PEG-SPIONs (FIGS. 2A and 2D). DLS measurements of DNA-SPIONs demonstrated a mean hydrodynamic diameter and zeta potential of 55.8 nm and −25.2 mV, respectively (FIG. 2A). TEM imaging of the DNA-SPIONs showed that the size and morphology of their SPION core was similar to those of PEG-SPIONs (FIG. 2B). Upon incubation with DMEM containing 10% FBS at 37° C. for 24 hours, the DNA-SPIONs attained a mean hydrodynamic diameter of 74.7 nm; 20 nm larger than their diameter before serum incubation in agreement with the PEG-SPION data (FIG. 2A). The higher electrophoretic mobility of DNA-SPIONS compared to PEG-SPIONs confirmed the attachment of the negatively charged DNA oligonucleotides (FIG. 2D). In general, the physical diameter revealed by TEM imaging is somewhat smaller than the hydrodynamic diameter measured by DLS due to the presence of an organic PEG coating layer. The data for PEG- and DNA-SPIONs demonstrated that both were stable, with only ~20 nm increase of hydrodynamic sizes, which was considered to be due to the adsorption of fetal bovine serum proteins ("protein corona") present in DMEM (47).

The magnetic properties of the SPIONs were investigated by a vibrating sample magnetometer (VSM). A near zero remanence for the PEG-SPIONs was detected and it was found that their saturation magnetization (Ms) value was 55 emu/(gram of iron oxide), which corresponds to 76 emu/(gram of Fe) (FIG. 2C). The superparamagnetic property and high magnetization of the as-synthesized PEG-SPIONs make them attractive T2-weighted magnetic resonance imaging (MRI) contrast agents, causing both local and global perturbations in the magnetic field and generating negative MRI signal contrast (48).

Figure 3A:
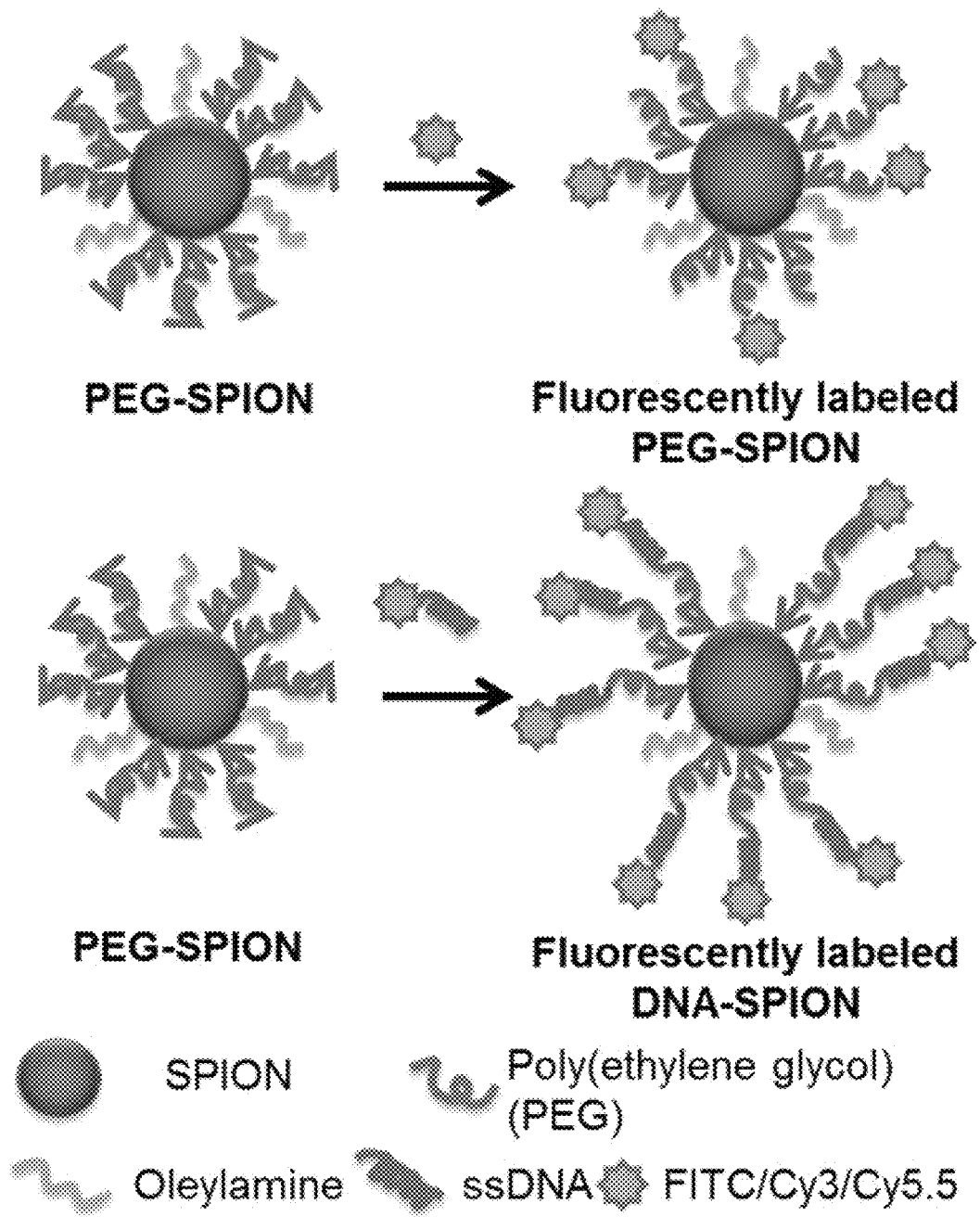
FIG. 3A shows a schematic the preparation of FITC-PEG-SPIONs and FITC-DNA-SPIONs.
Figure 3B:
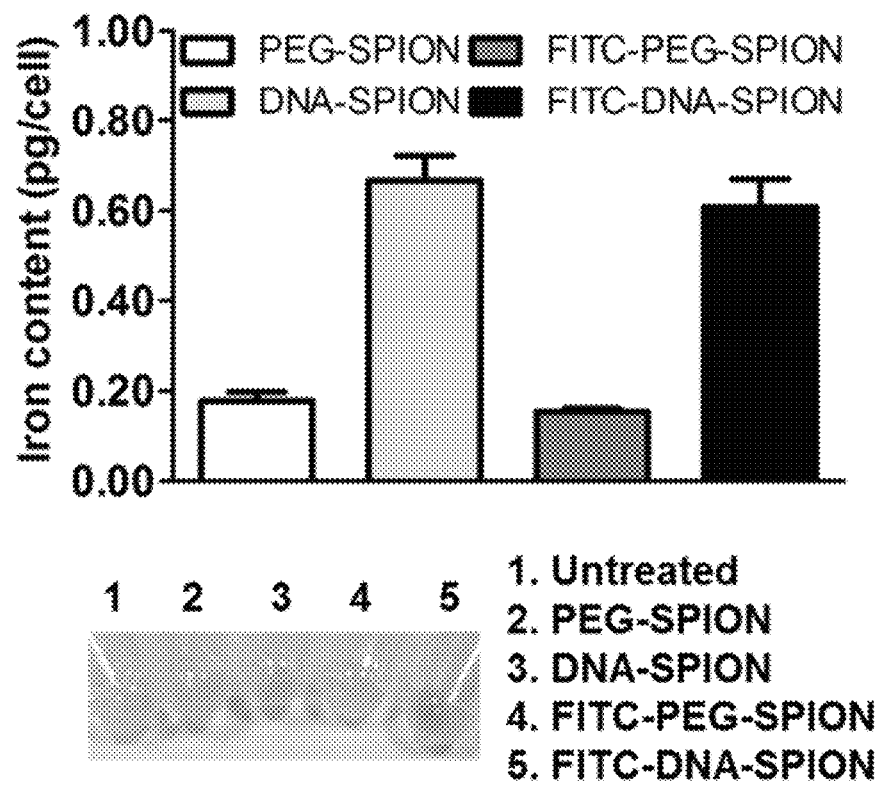
FIG. 3B shows cellular uptake of FITC-labeled SPIONs in RAW 267.4 cells.

Since the DNA loading density is a key parameter that governs the cellular uptake efficiency of DNA-SPIONs (49), the number of DNA sequences per nanoparticle was quantified by measuring the fluorescence intensity of FITC conjugated DNA. To this end, carboxy-terminated PEG-SPIONs were reacted with bifunctional DNA-oligonucleotides that comprised an amine group on one end and a fluorescein isothiocyanate (FITC) molecule on the other end to form FITC-labeled DNA-SPIONs (FIG. 3A and Table S1). The DNA loading was ascertained by measuring the concentration of FITC-labeled DNA strands in the reaction mixture before and after the EDC/NHS coupling reaction. The average DNA loading of the DNA-SPIONs amounted to ~61 DNA strands per PEG-SPION (FIG. 3B). Similarly, PEG-SPIONs were fluorescently labeled by reacting carboxy-terminated PEG-SPIONs with amine-functionalized FITC (fluorescein cadaverine). The reactivity of PEG-SPIONs toward amine-functionalized FITC was quantified as ~85 FITC-labeled PEG molecules per nanoparticle (FIG. 3B). Although the coverage of DNA was lower than, e.g., AuNP-based SNAs of similar sizes (50) and other SPION-based SNAs prepared via "click reactions" (51), the as-synthesized DNA-SPIONs of the subject invention already showed much higher efficiency in cellular uptake with this convenient and cost-effective synthesis method. Fluorophore-labeled SPIONs were used for confirmatory uptake and distribution studies both in vitro and in vivo. Since no significant difference in cellular uptake of SPIONs was observed after FITC labelling on both PEG and DNA (FIG. 3B), the fluorescent SPIONs were considered to have the same intracellular behavior as non-fluorescent ones.

EXAMPLE 2

SR-A Expression on Different Cell Types and Cellular Uptake of DNA-SPIONs.

Figure 4A:
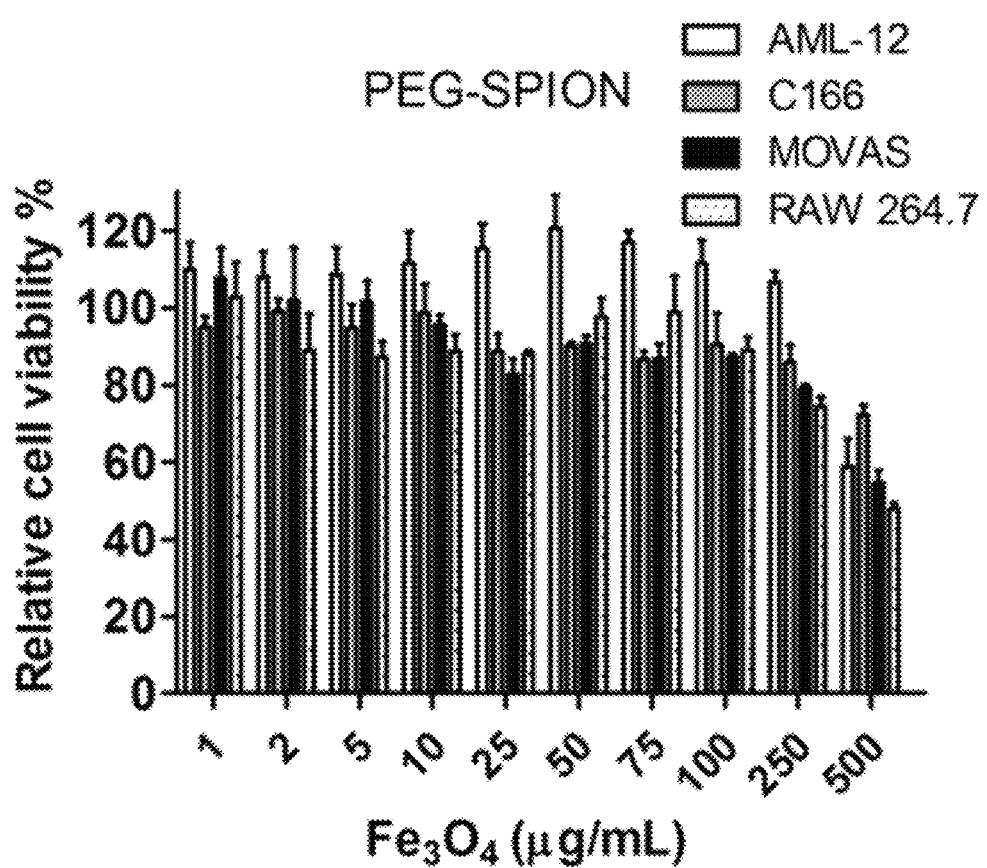
FIG. 4A shows MTT assay results to quantify cytotoxicity of PEG-SPIONs in AML-12, C166, MOVAS, and RAW 264.7 cells.
Figure 4B:
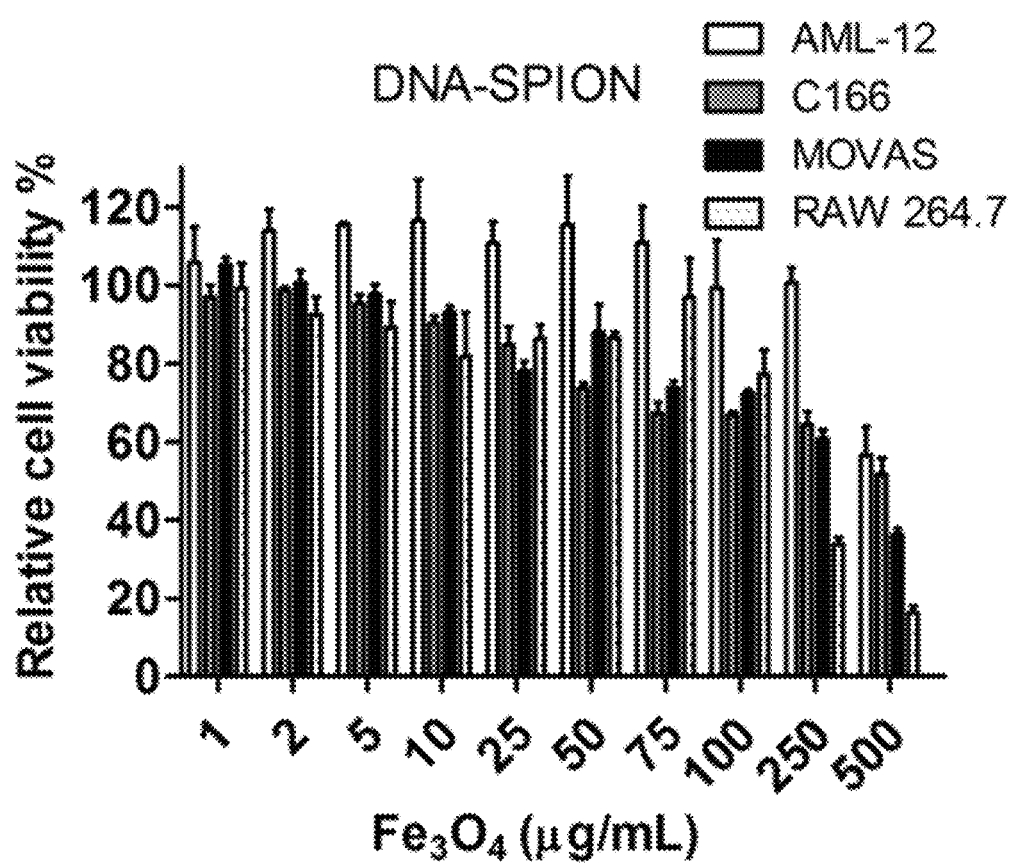
FIG. 4B shows MTT assay results to quantify cytotoxicity of DNA-SPIONs in AML-12, C166, MOVAS, and RAW 264.7 cells.

As shown in FIG. 1B, the major cell types in atherosclerotic plaques are monocyte/macrophage, smooth muscle cells and endothelial cells (40, 52). To probe the interaction of DNA-SPIONs with different types of cells representative of cells present inatherosclerotic plaques, the uptake of nanoparticles in four model cell types was studied in vitro, including mouse endothelial (C166), mouse smooth muscle (MOVAS) and mouse macrophage (RAW 264.7) cells. Since nanoparticles are known to be able to accumulate in organs of the mononuclear phagocyte system (MPS), including liver and spleen (55), mouse hepatocytes (AML-12) were also included for comparison. Before conducting cellular uptake studies, the cytotoxicity of PEG-SPIONs and DNA-SPIONs to the four types of cells was tested by MTT assay. In this MTT assay, PEG-SPIONs and DNA-SPIONs were incubated with cells for 24 hours (FIG. 4). No obvious cytotoxicity of PEG- or DNA-SPIONS at the concentration used for the cellular uptake studies was observed (50-100 µg/mL Fe3O4, which is equivalent to 2.5-5.0 nM SPIONs) (FIG. 4A and 4B).

Figure 5A:
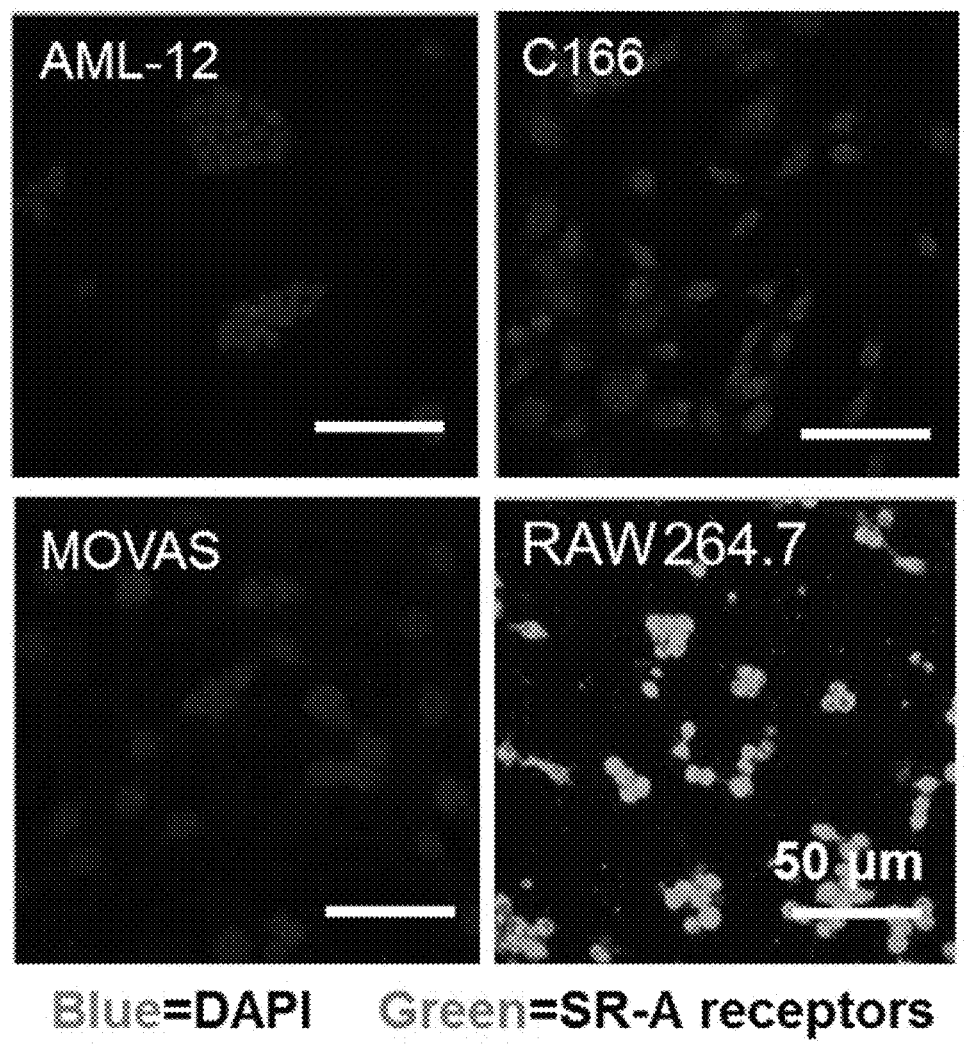
FIG. 5A shows confocal microscopy images of RAW 267.4 (macrophages), C166 (endothelial) cells, MOVAS (smooth muscle), and AML-12 (hepatocyte) cells labeled for SR-A (green).

For uptake studies, the expression of SR-A receptors on different cells was quantified by immunofluorescence staining. The SR-A receptors were shown as green signals, with cell nucleus stained with DAPI (FIG. 5A). The result indicated extensive SR-A expression on macrophage cells, evidenced by saturated green signals in RAW 264.7, while the other three cell lines, AML-12, C166, and MOVAS, showed neglectable green color suggesting detectable but little expression of SR-A. The difference was also shown in western blot analysis (FIG. 5B) suggesting enrichment in expression of SR-A receptors in RAW264.7 compared to the other three cell types. The cell lines were then incubated with 2.5 nM (FIG. 5C) or 5 nM SPIONs (FIG. 5D) for 4 hours and SPION association with the cells was quantified by ICP-MS. Two primary cell types were also included in these studies. Bone marrow derived macrophages (BMDM) and bone marrow derived dendritic cells (BMDC), which both express high levels of SR-A (FIG. 5F), were isolated from ApoE$^{-/-}$ mice. Primary BMDM and BMDC cells were incubated with 5 nM SPIONs for 4 hours.Cells were incubated with equal molar PEG-SPIONs as controls. After 24 hours, the cells were collected and lysed for ICP-MS quantification of iron content.

Figure 5B:
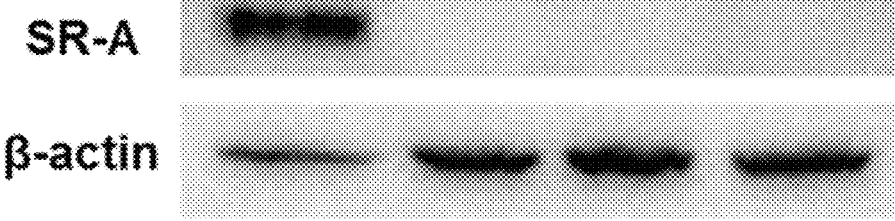
FIG. 5B shows a western blot analysis of SR-A expression in the four cell lines.
Figure 5C:
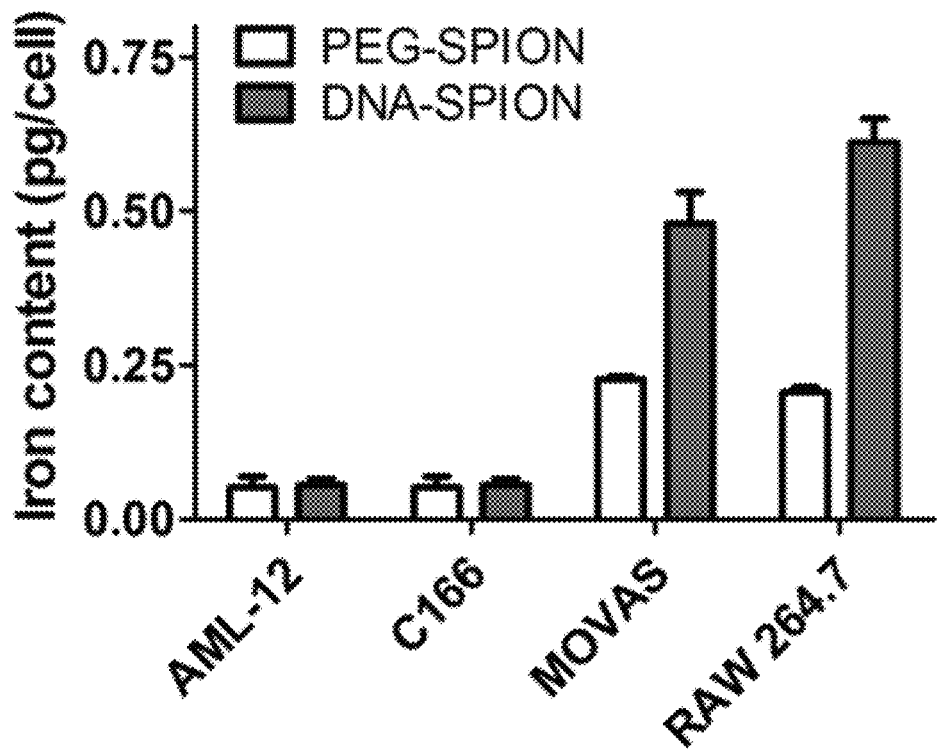
FIG. 5C shows the cellular uptake of 5 nM DNA-SPIONs and 5 nM PEG-SPIONs detected by inductively coupled plasma mass spectroscopy (ICP-MS).
Figure 5C:
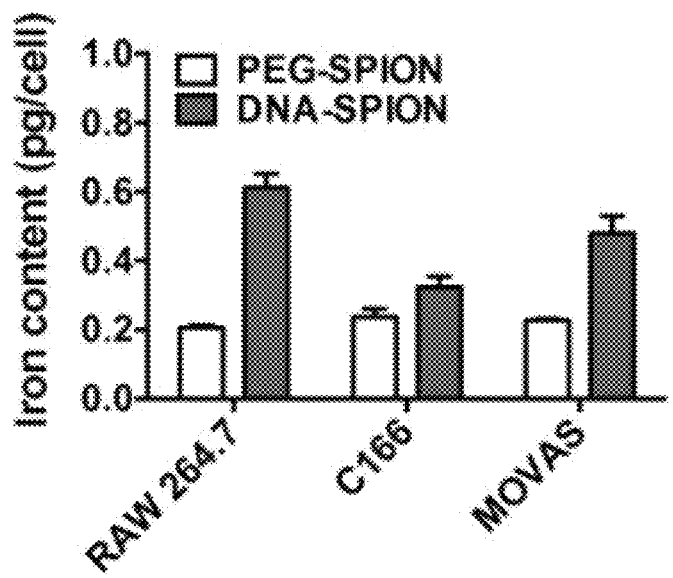
Figure 5D:
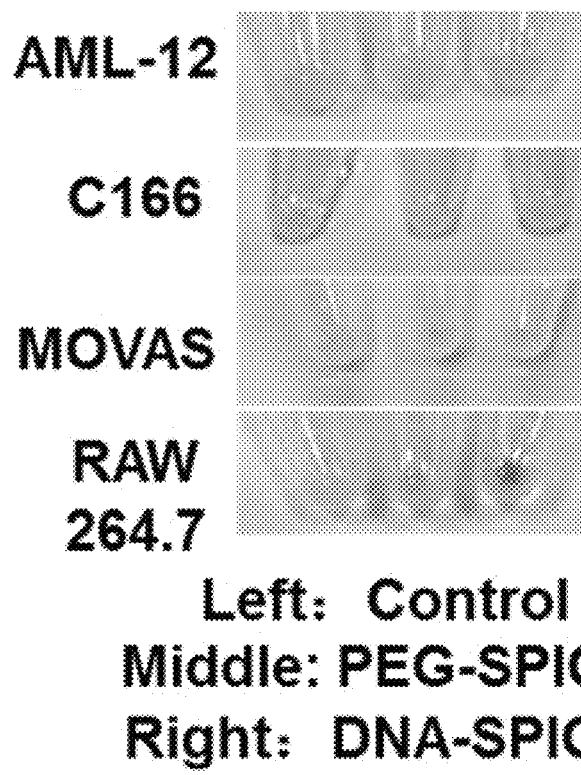
FIG. 5D shows images of iron content in cell pellets as indicated by brownish color.
Figure 5E:
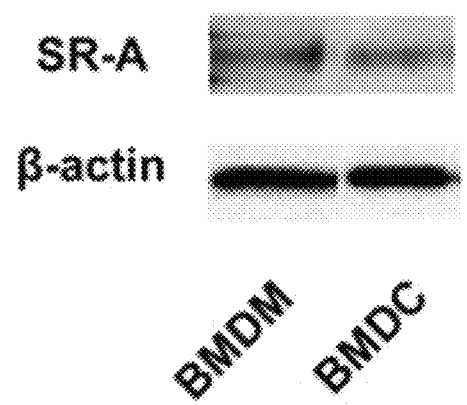
FIG. 5E shows a western blot analysis of SR-A expression in bone marrow derived macrophages (BMDM) and bone marrow derived dendritic cells (BMDC).
Figure 5F:
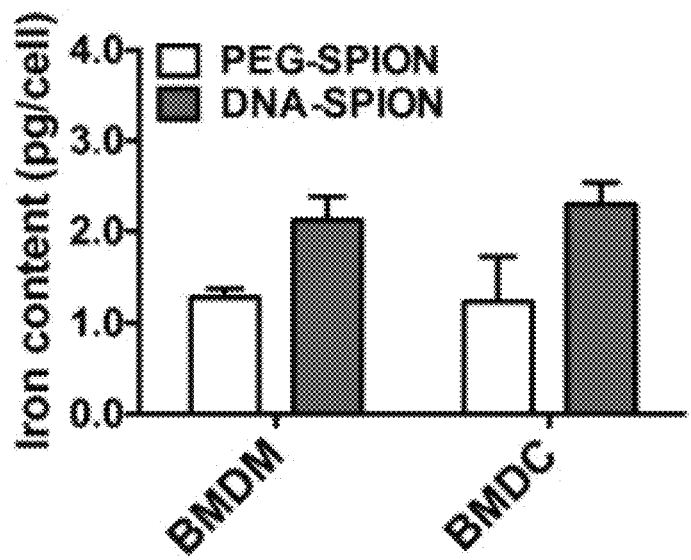
FIG. 5F shows the cellular uptake of PEG-SPIONs and DNA-SPIONs in BMDM and BMDC cells.

Upon 4 hour of incubation with 2.5 nM and 5 nM, respectively, the total association of DNA-SPIONs with each RAW 264.7 cell amounted to 0.6 pg, 3-fold higher than that of PEG-SPIONs (0.2 pg/cell) (FIGS. 5C and 5D). PEG-SPIONs and DNA-SPIONs did not show a remarkable difference in their inability to associate with AML-12 and C166 cells at 2.5 nM SPIONs (FIG. 5C). Even at 5 nM SPIONs, C166 cells did not demonstrate a marked difference between PEG-SPIONs and DNA-SPIONs (0.2 pg/cell versus 0.3 pg/cell, FIG. 5D). These results were consistent with the observation that AML-12 and C166 cells did not exhibit high expression levels of SR-A (FIG. 5B). For MOVAS cells, the cellular association of PEG-SPIONs and DNA-SPIONs at 2.5 nM and 5nM amounted to ~0.2 pg/cell and ~0.5 pg/cell, respectively (FIGS. 5C and 5D) despite immunofluorescence and western blot data that indicated only limited expression of SR-A (FIGS. 5A and 5B). MOVAS cells have an elongated shape and edge length of up to 100 µm and are significantly larger than RAW 264.7 cells with a round shape and diameter of about 10 µm (see, e.g., American Type Culture Collection (ATCC) website). Taking the shape and dimensions into considerations, the actual cellular association of both SPION types to MOVAS cells approximately approached the levels observed in C166 endothelial cells, i.e., ~0.2-0.3 pg/cell for both types of SPIONs. Pictures of the pellets of all cell types after 4 hour incubation with DNA-SPIONs and PEG-SPIONs portrayed the darkest brown color for RAW 264.7 cells treated with DNA-SPIONs (FIG. 5E).

Figure 5G:
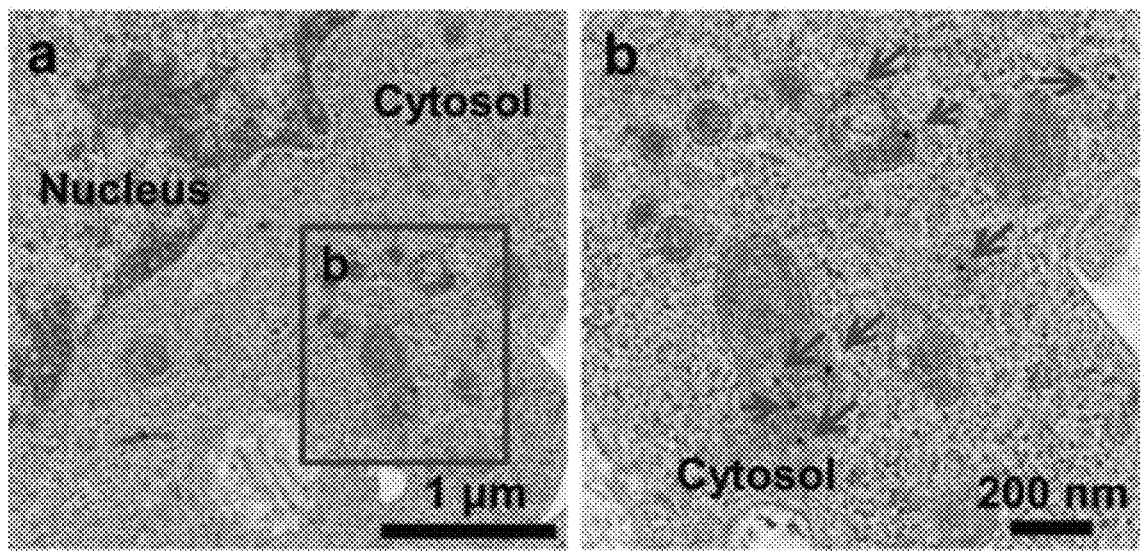
FIG. 5G shows TEM images of RAW 264.7 cells exposed to PEG-SPIONs.

Primary BMDM and BMDC cells associated with DNA-SPIONs nearly twice more preferentially compared to PEG-SPIONs, amounting to ~1.2 pg/cell for PEG-SPIONs and ~2.2 pg/cell for DNA-SPIONs (FIG. 5G).

Figure 5H:
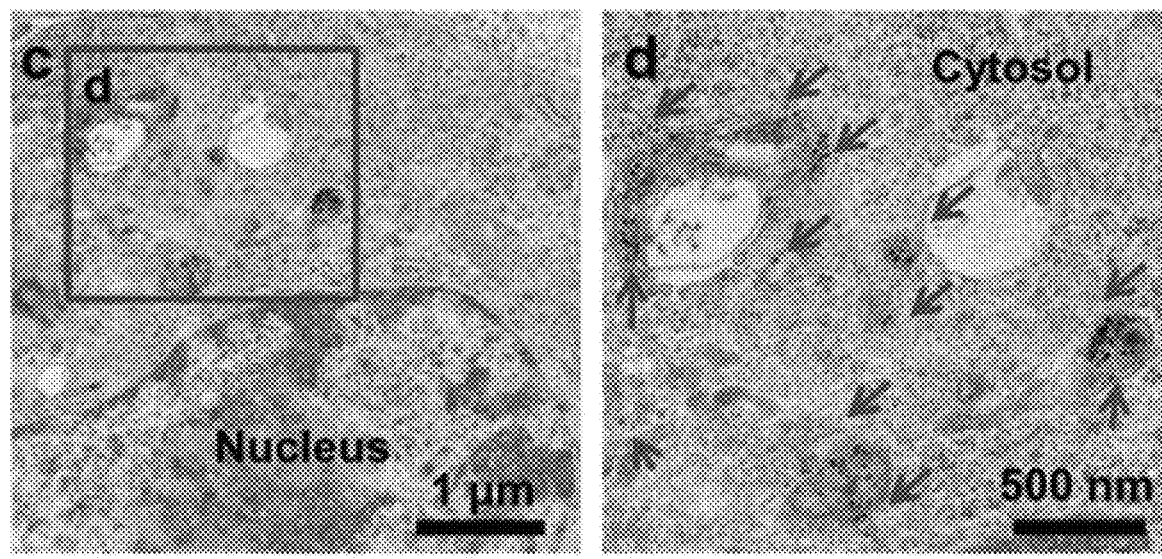

The selective association of DNA-SPIONs was confirmed in RAW 264.7 cells using TEM imaging. In agreement with the ICP-MS data, DNA-SPIONs entered RAW 264.7 cells more profusely (FIG. 5I) compared to PEG-SPIONs (FIG. 5H) with a higher number of DNA-SPIONs occupying intracellular vesicles compared to PEG-SPIONs. Taken together, these results indicated that DNA-SPIONs enter macrophages more selectively compared to PEG-SPIONs in vitro making DNA-SPIONs well-suited as imaging agents and drug carriers for atherosclerotic plaques.

EXAMPLE 3

Cellular Uptake Kinetics of PEG-SPIONs and DNA-SPIONs in RAW 264.7 Cells

Figure 6A:
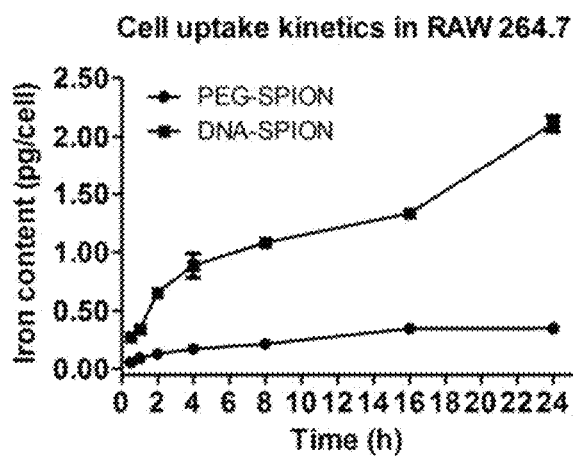
FIG. 6A shows the cellular uptake kinetics of DNA-SPIONs by RAW 264.7 cells determined by inductively coupled plasma mass spectroscopy (ICP-MS) of iron content (left) and images of iron content in cell pellets (right).
Figure 6A:
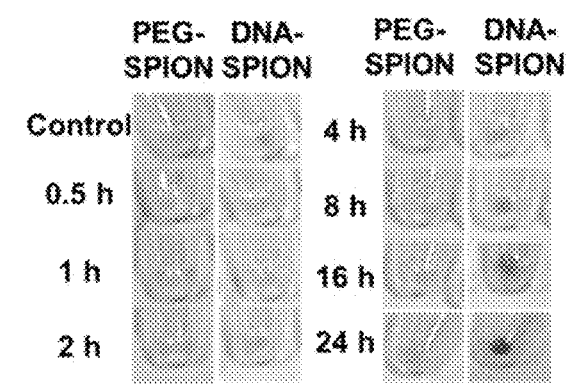

The time-course uptake of both types of nanoparticles was studied by ICP-MS for measurement of iron content after incubation for different durations of time. During the first 8 hours of uptake, DNA-SPIONs associated with RAW 264.7 cells much faster than PEG-SPIONs (FIG. 6A). For example, 4 hours post-incubation, the iron content of cells treated with DNA-SPIONs was more than 5-fold higher than that of cells treated with PEG-SPIONs (0.89 pg/cell versus 0.17 pg/cell), validating the selective uptake of DNA-SPIONs over PEG-SPIONs by RAW 264.7 macrophages as shown in FIGS. 5C and 5D. The cellular association of DNA-SPIONs showed little increment in iron content between 8 hours and 16 hours, an observation potentially related to the doubling time of RAW 264.7 cells that is ~12 hours for a standard plate set-up (56, 57).

Figure 7A:
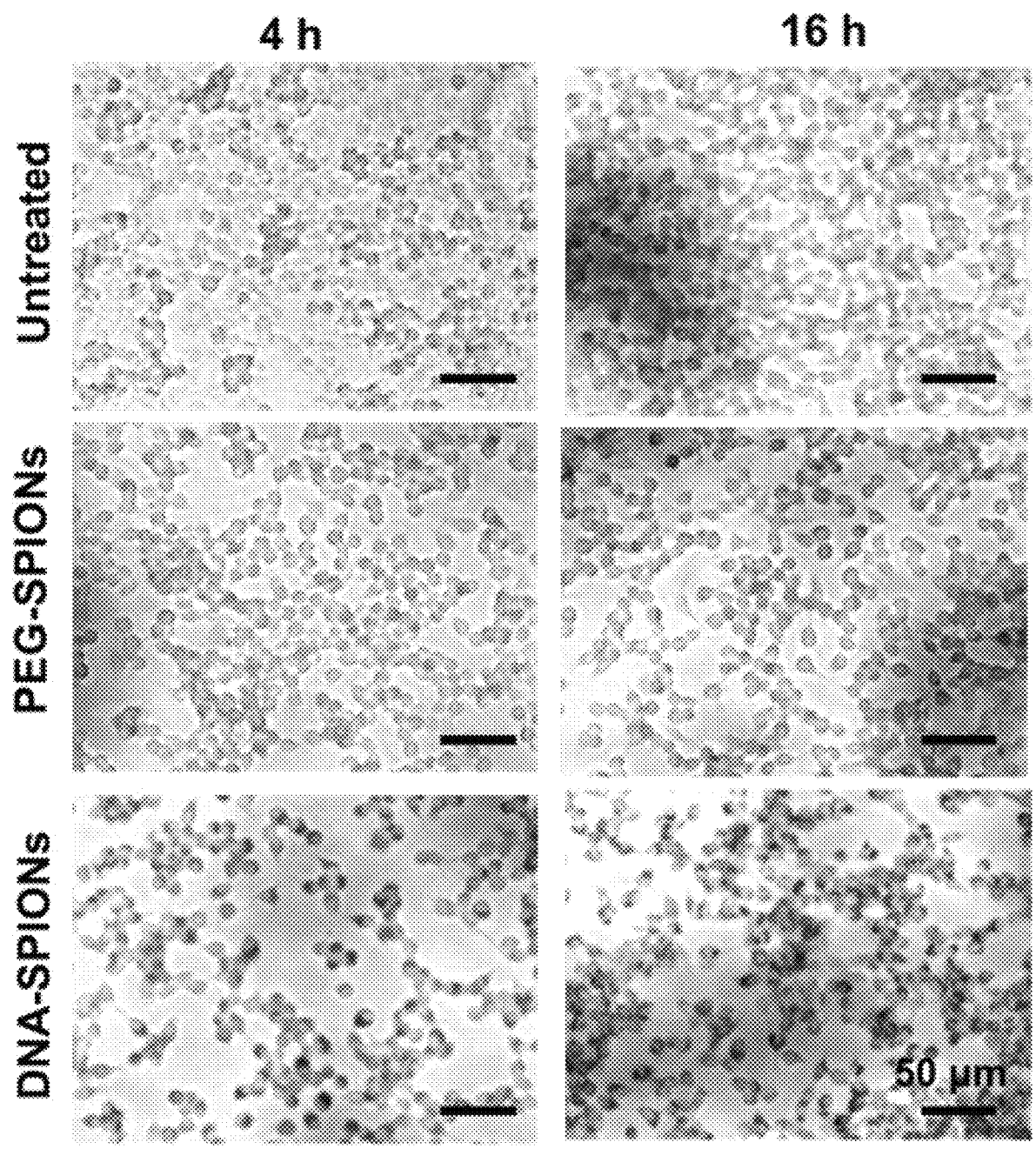
FIG. 7A shows microscopic images of cells incubated with PEG-SPIONs and DNA-SPIONs after Prussian blue staining.

Prussian blue staining, which turns content iron into blue signals and, thus, detects the presence of the SPION cores inside a cell, demonstrated an enormous difference in iron content 4 hours and 16 hours after SPION incubation with almost colorless cells incubated with PEG-SPIONs compared to intensely blue-stained cells incubated with DNA-SPIONs (FIG. 7A). The observed difference persisted up to 16 hours consistent with the ICP-MS data.

Figure 6B:
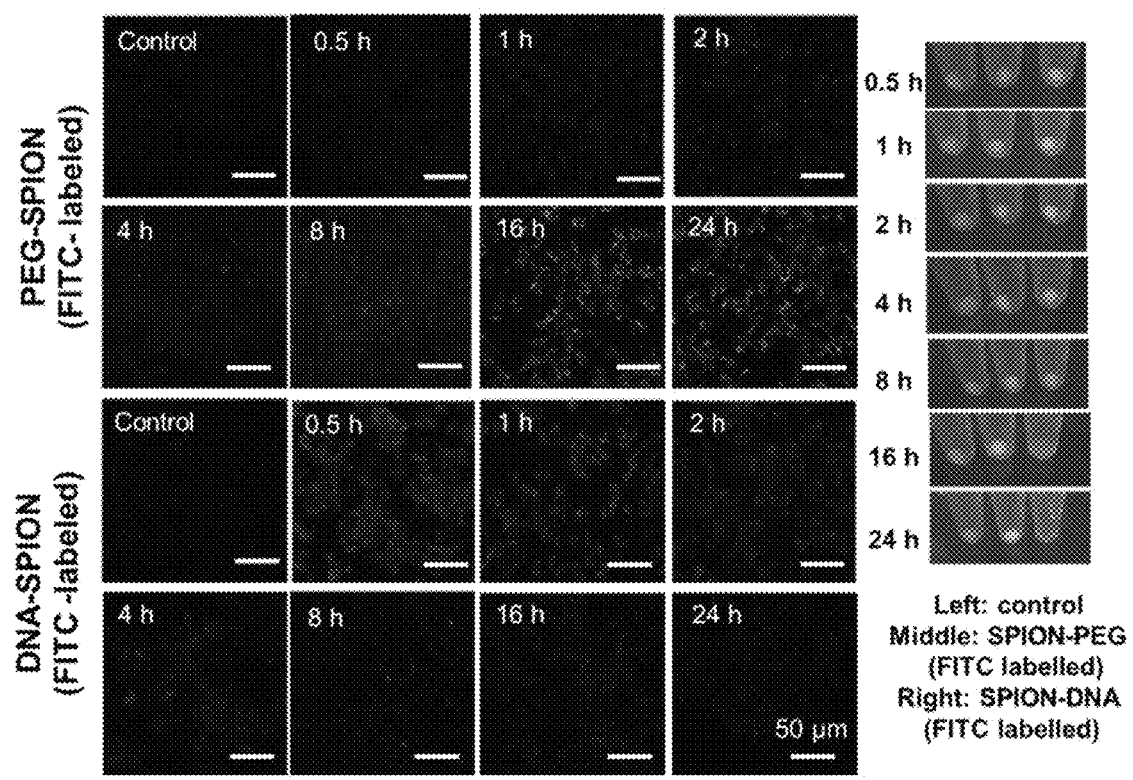
FIG. 6B shows confocal microscopy images of cells incubated with FITC-labeled DNA-SPIONs and PEG-SPIONs (left) and fluorescence intensity of cell pellets (right).

Since ICP-MS only measures the intracellular iron content due to the entry of Fe3O4-cored nanospheres but fails to provide information on the DNA sequences on the surface of nanoparticles after their intracellular entry, the cellular uptake kinetics of PEG- and DNA-SPIONs were monitored using immunofluorescence. To track the DNA oligonucleotides, FITC-labeled DNA-SPIONs were prepared identical to those used above for the quantification of DNA loading. To track PEG-SPIONs, EDC/NHS chemistry was used to couple amino-functionalized FITC to the carboxy-terminated PEG-SPIONs to form FITC-labeled PEG-SPIONs, each of which bore ~85 FITC molecules (FIG. 3B). By ICP-MS analysis it was confirmed that the covalent attachment of FITC molecules to the PEG-SPIONs and DNA-SPIONs did not drastically affect their ability to associate with RAW 264.7 cells when compared to their non-fluorescent counterpart SPIONs (FIG. 3B). Confocal microscope was used to study the time-course uptake of FITC-labelled PEG-SPIONs and DNA-SPIONs. Their uptake kinetics in RAW 264.7 cells were compared by recording different fluorescence intensities at various time points (FIG. 6B). FITC signals were first detected in FITC-PEG-SPION incubated cells 1 hour after incubation and gradually increased (FIG. 6B). Comparatively, very strong FITCsignals were detected in cells incubated with DNA-SPIONs after only 0.5 hours indicating a much more rapid accumulation of DNA-SPIONs in the cells. Four hours post-incubation, FITC-DNA-SPIONs associated with RAW 264.7 cells nearly 5 times more than FITC-PEG-SPIONs (FIG. 6B). Sixteen hours after incubation, the intracellular FITC fluorescence continued to increase in FITC-PEG-SPION incubated cells, corroborating the ICP-MS and Prussian blue data that suggested a continuous uptake of PEG-SPIONs by RAW 264.7 cells. However, the FITC fluorescence in the cells treated with FITC-DNA-SPIONs vanished after 8-16 hours in spite of the ICP-MS and Prussian blue staining data that demonstrated increasing accumulation of the SPION core (FIGS. 6A and 7A). This discrepancy in the time course of intracellular accumulation of SPIONs and DNA is attributed to the degradation of DNA strands attached to the SPION core, a phenomenon previously reported for FITC-labeled SNAs inside C166 cells 16 hours post-incubation (60).

Previous studies had shown that fluorescence intensity of FITC was strongly dependent on pH, with only ~10% fluorescence intensity in lysosomal pH (~4.8) compared to physiological environment (pH=7.4) (58, 59).

Figure 7B:
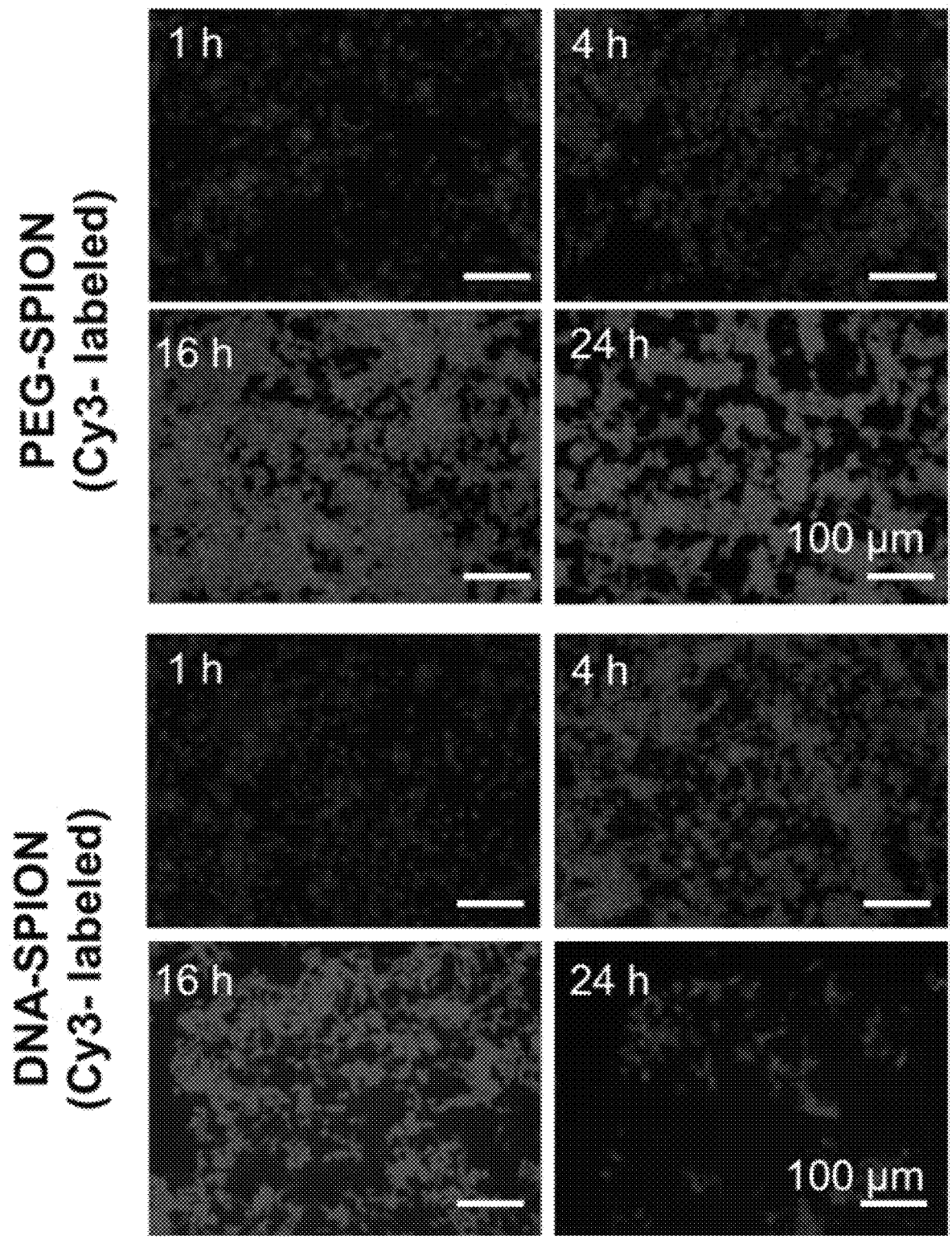
FIG. 7B shows confocal microscopy images of RAW 267.4 cells incubated with Cy3-labeled PEG-SPIONs and Cy3-labeled DNA-SPIONs.

The confocal imaging study was repeated using Cyanine 3 (Cy3)-labeled PEG-SPIONs and Cy3-DNA-SPIONs. By changing the fluorophores from FITC to Cy3, intense Cy3-fluorescence inside RAW 264.7 cells was observed for Cy3-PEG-SPIONs only after 16 hours of incubation, whereas the intracellular fluorescence was barely detectable during the first 4 hours (FIG. 7B). This observation was consistent with those for FITC-PEG-SPIONs. For Cy3-DNA-SPIONs, the Cy3 fluorescence was detectable as soon as 1 hour post incubation, mirroring the rapid cellular uptake kinetics of FITC-DNA-SPIONs (FIG. 7B). Importantly, the fluorescence of Cy3-DNA-SPIONs vanished to an undetectable level 24 hours post-incubation, further supporting the notion of degradation of DNA (FIG. 7B).

Figure 8:
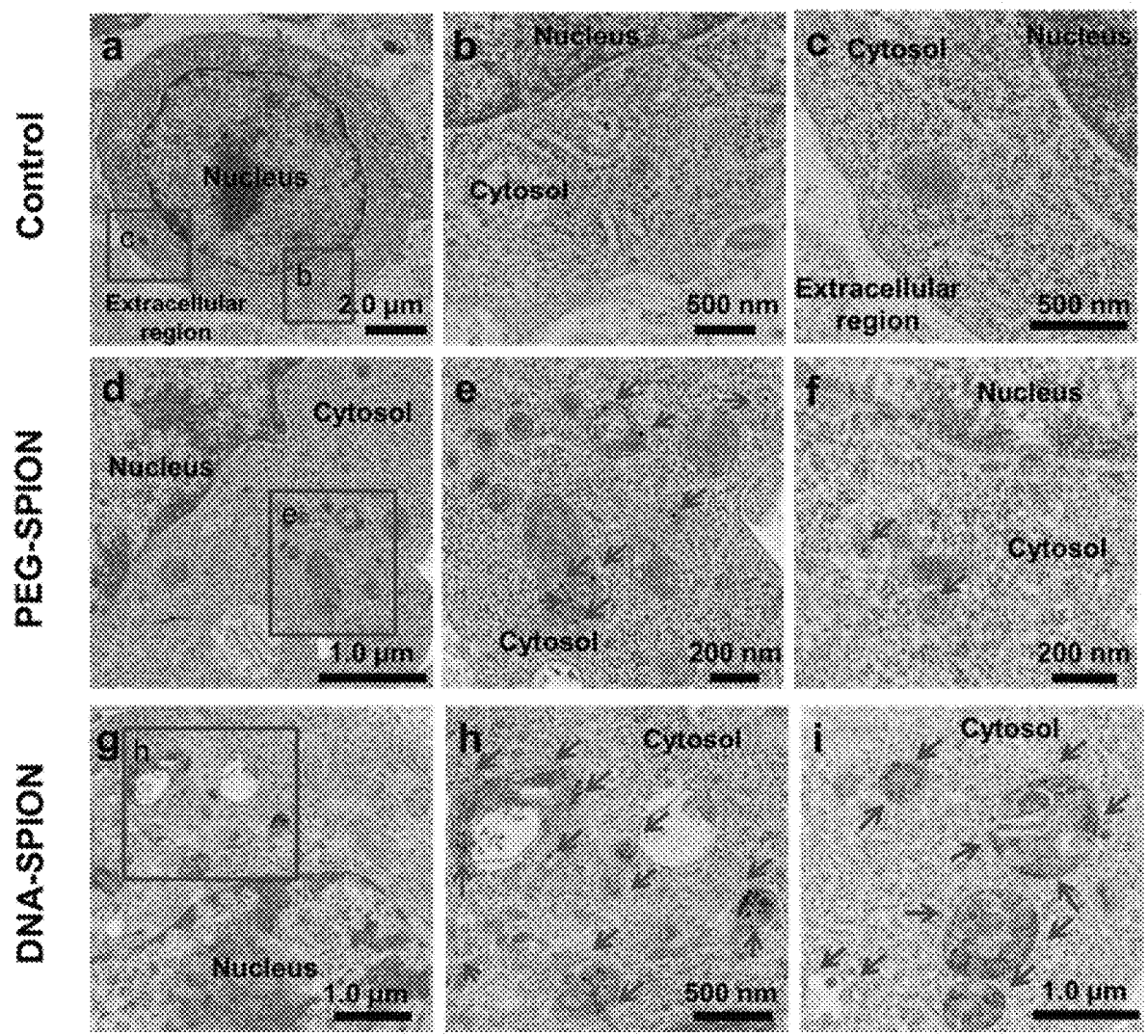
FIG. 8 shows Transmission Electron Microscopy (TEM) images of the cellular uptake of PEG-SPIONs and DNA-SPIONs by RAW 264.7 cells.

Cellular uptake of PEG- and DNA-SPIONs was also studied by TEM. Four hours post incubation was chosen as a representative time point. At this time point, large clusters of DNA-SPIONs were found abundantly present in peri-nuclear luminal vesicles (FIG. 8). On the other hand, only a few PEG-SPIONs were observed in smaller vesicles the typical size of early endosomes (~200 nm in diameter) (FIG. 8), indicating lower uptake efficiency and slower uptake kinetics of PEG-SPIONs.

EXAMPLE 4

Endocytosis of DNA-SPIONs in Macrophages Occurs via SR-A and Lipid-Raft

Figure 9A:
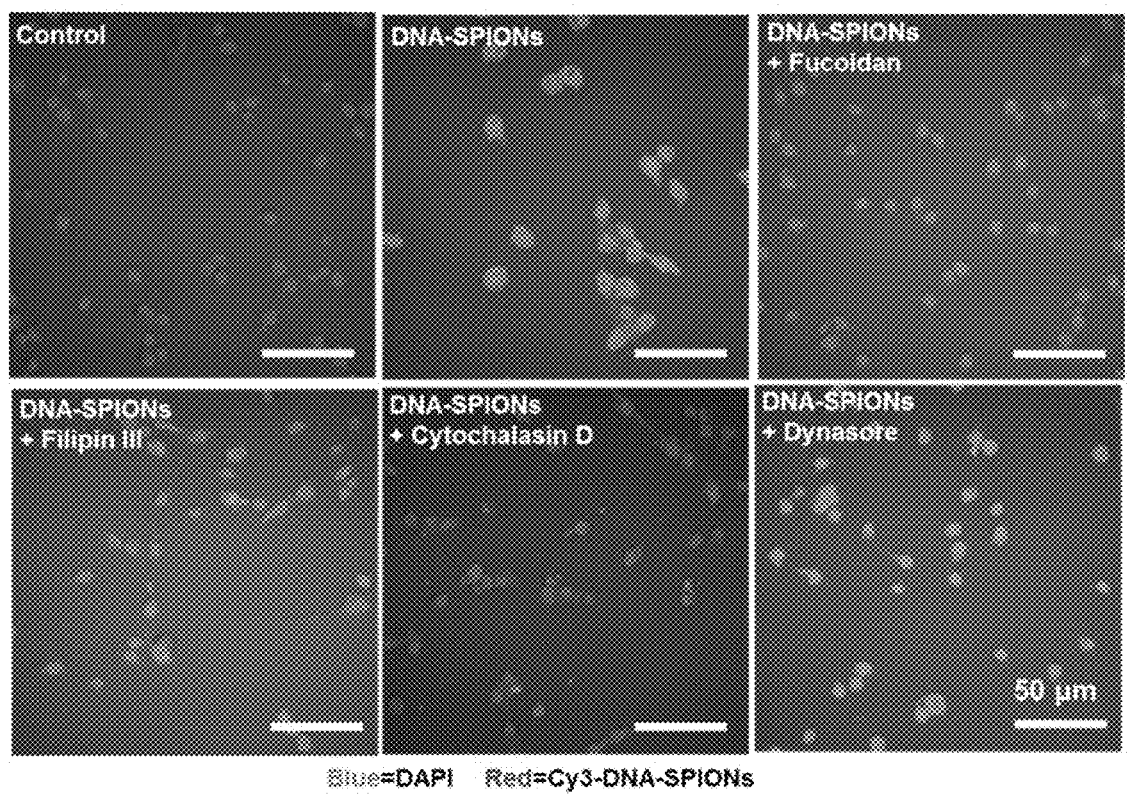
FIG. 9A shows confocal microscopy images of RAW 267.4 cells incubated with Cy3-labeled DNA-SPIONs following treatment with fucoidan, filipin III, cytochalasin D, and dynasore.
Figure 9B:
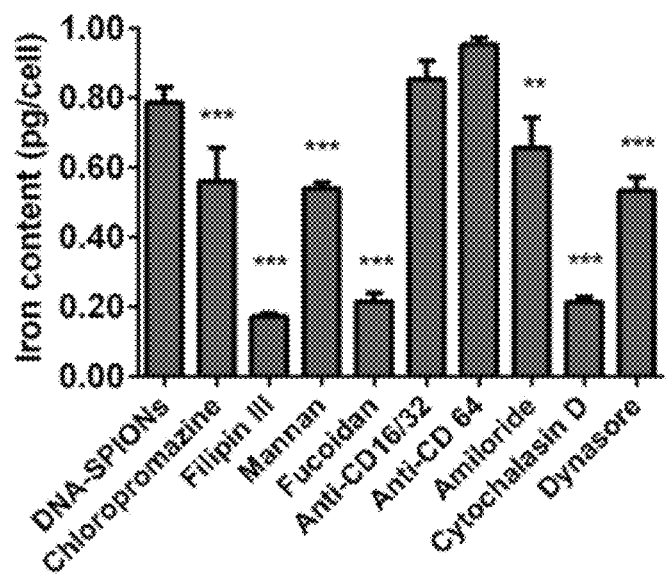
FIG. 9B shows ICP-MS measurement of iron content in RAW 267.4 cells incubated with Cy3-labeled DNA-SPIONs following treatment with fucoidan, filipin III, cytochalasin D, and dynasore.
Figure 9C:
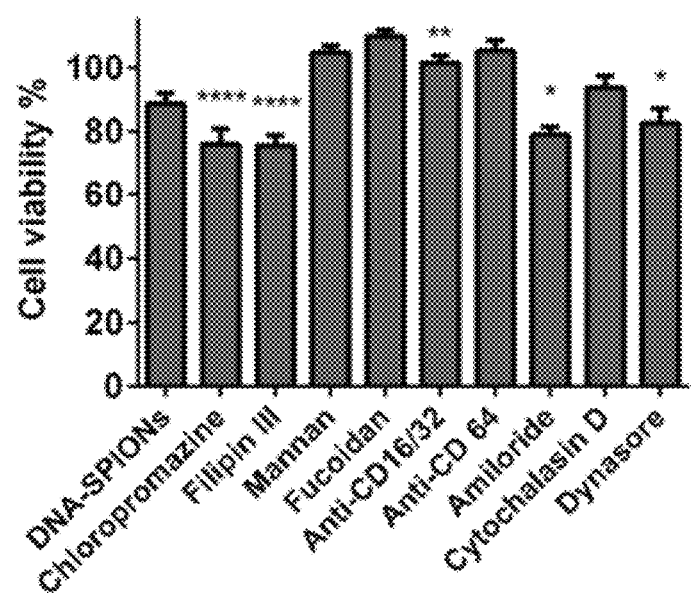
FIG. 9C shows cell viability by Almar Blue assay in RAW 267.4 cells incubated with Cy3-labeled DNA-SPIONs following treatment with fucoidan, filipin III, cytochalasin D, and dynasore.

A previous study had shown that SNAs enter mouse endothelial cells (C166) through targeting of SR-A (also known as MSR1) and endocytosis via a lipid-raft-dependent, caveolae-mediated pathway (35), irrespective of the chemical composition of nanoparticle cores (60). The uptake of DNA-SPIONs was examined in RAW 264.7 murine macrophages. To this end, RAW 264.7 cells were pre-treated with various pharmacological inhibitors (Table S2) for 1 hour to block certain pathways of cellular uptake at concentrations that did not induce cytotoxicity (FIG. 9C). Table S2 is a list of the pharmacological inhibitors and the final concentrations of such inhibitors used.

TABLE S2

| No. | Target | Chemical blocker/antibody | Stock solution | Final concentration |
| --- | --- | --- | --- | --- |
| 1 | Clathrin | Chlorpromazine | 1 mg/mL (in water) | 5 µg/mL |
| 2 | Lipid raft/caveolae | Filipin III | 2 mg/mL (in 100% DMSO), then dilute 1:7 in PBS | 2.5 µg/mL |
| 3 | Mannose receptor | Mannan | 100 mg/mL (in water) | 1 mg/mL |
| 4 | SR-A receptor | Fucoidan | 10 mg/mL (in water) | 100 mg/mL |
| 5 | FcγII/III receptor | Anti-CD16/32 antibody | 0.5 mg/mL (in water) | 10 µg/mL |
| 6 | FcγI receptor | Anti-CD64 antibody | 0.5 mg/mL (in water) | 10 µg/mL |
| 7 | Macropinocytosis | Amiloride | 250 mg/mL (in 100% DMSO), then dilute 1:9 in water | 250 µg/mL |
| 8 | Actin | Cytochalasin D | 20 mM (in 100% DMSO) | 20 µM |
| 9 | Dynamin | Dynasore | 80 mM (in 100% DMSO) | 80 µM |

The pre-treated RAW 264.7 cells were then exposed to Cy3-DNA-SPIONs for 4 hours followed by detection of any attenuation in cellular uptake by ICP-MS and confocal microscopy. Fucoidan was added as a competitive ligand of SR-A to block scavenger receptors, filipin III was used as a specific inhibitor of lipid raft/caveolae-mediated endocytosis that sequesters cholesterol, and cytochalasin D was added to disrupt the polymerization of actin filaments. By ICP-MS analysis, a severe reduction in iron content by ~73%, ~78%, and ~73%, respectively, was observed in RAW 264.7 cells treated with fucoidan filipin III, and cytochalasin D (FIG. 9B). In parallel confocal imaging experiments, RAW 264.7 cells were pre-treated with fucoidan, filipin III, and cytochalasin D before incubation with Cy3-DNA-SPIONs. Consistent with the ICP-MS results, the three inhibitors markedly reduced Cy3-DNA-SPION intracellular fluorescence compared to untreated control cells (FIG. 9A). The results demonstrated the involvement of SR-A, caveloae, and actin in mediating uptake of DNA-SPIONs. In parallel, ICP-MS was performed to quantitatively measure the iron content after pre-treating the cells with different pharmaceutical inhibitors and antibodies followed by incubation with DNA-SPIONs for 4 h (FIG. 9B). Pre-treatment with chemical blockers such as chlorpromazine, an inhibitor of clathrin-mediated endocytosis; amiloride, a blocker of micropinocytosis; dynasore, an inhibitor of dynamin-mediated endocytosis; and mannan, an inhibitor of phagocytosis mediated by the mannose receptor (61-64), merely yielded reductions in cellular DNA-SPION association by ~29%, ~17%, ~32%, and ~31%, respectively (FIG. 9B). Pre-treatment with antibodies against CD16/CD32 and CD64, both blockers of phagocytosis mediated by the Fcγ receptors (65-66) showed virtually no reduction in cellular DNA-SPION association (FIG. 9B). These data indicated no or limited involvement of clathrin-mediated endocytosis, micropinocytosis, and phagocytosis mediated by the mannose receptor and Fcγ receptor.

Since the toxicity of these blocking agents was a concern in affecting cellular uptake, an Alamar Blue assay was used to measure the cell viability after treatment of blockers for four hours (FIG. 9C). No observable toxicity was observed, validating the effectiveness of the chemical blockers and antibodies.

Figure 9D:
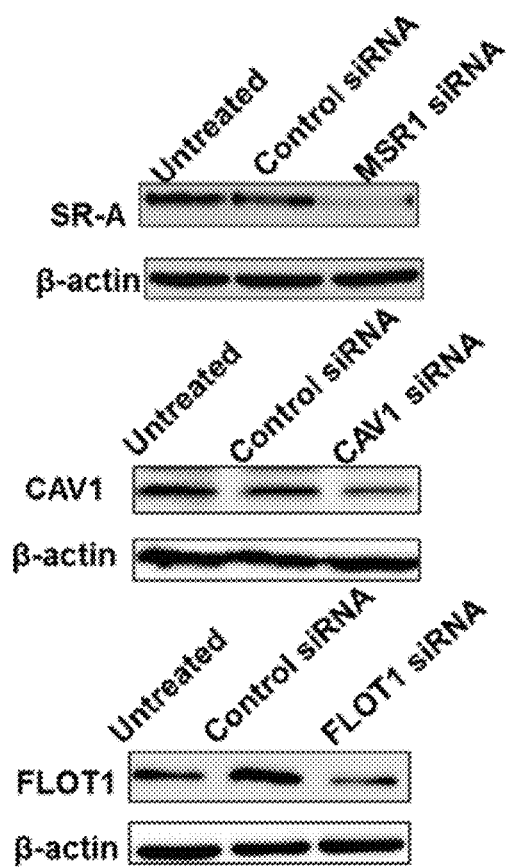
FIG. 9D shows a western blot analysis of si-RNA-transfected RAW 267.4 cells.
Figure 9E:
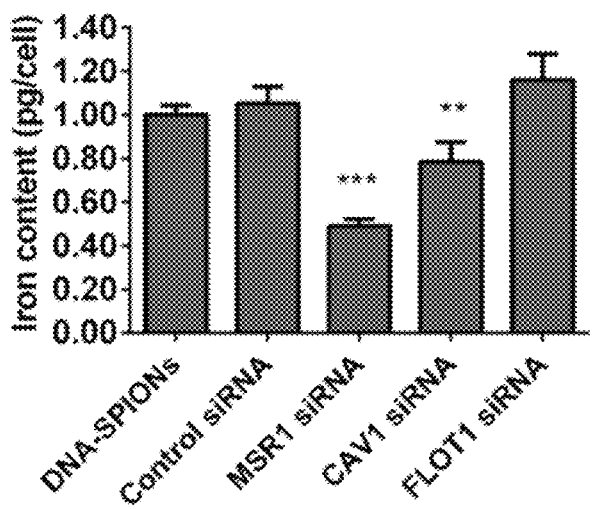
FIG. 9E shows ICP-MS measurement of iron content in RAW 267.4 cells incubated with Cy3-labeled DNA-SPIONs following treatment with fucoidan, filipin III, cytochalasin D, and dynasore.
Figure 10:
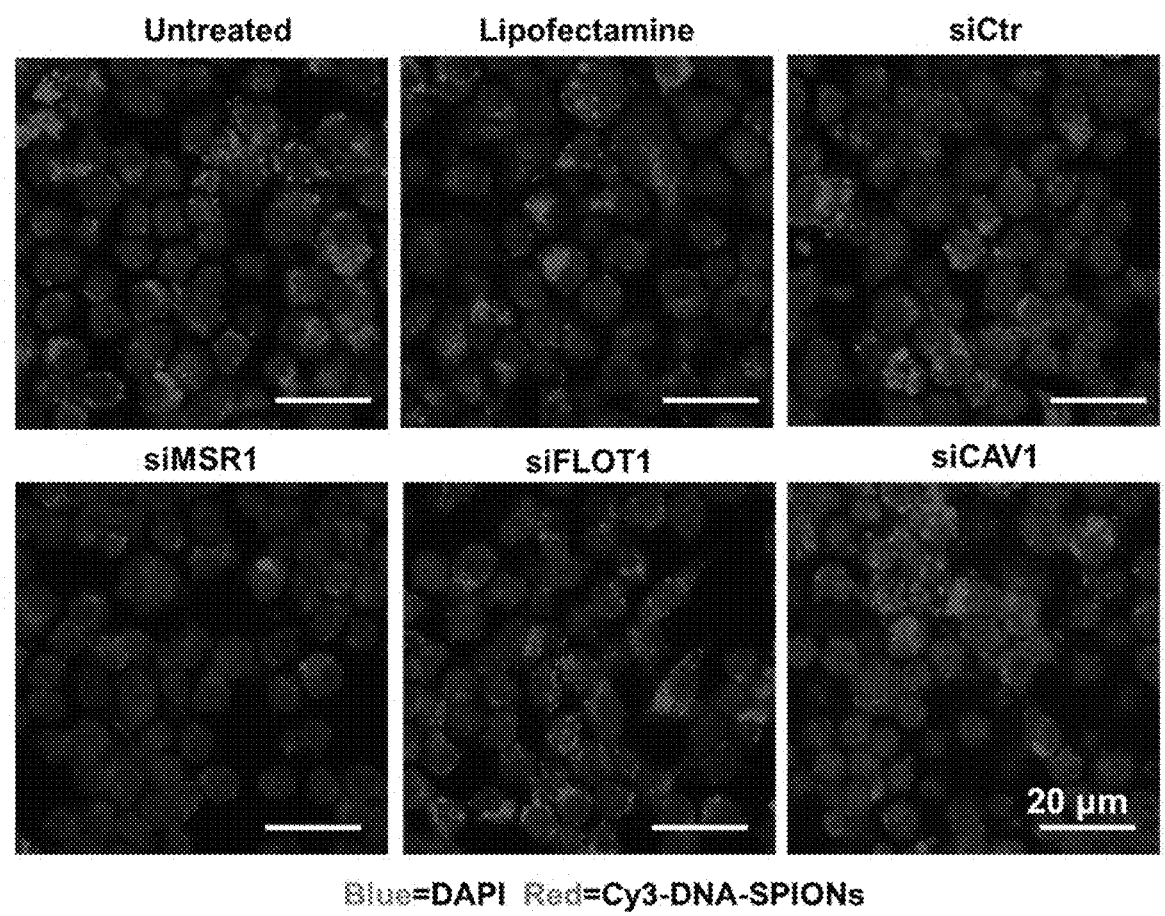
FIG. 10 shows confocal microscopy images of Cy3-labeled DNA-SPIONs and DAPI after treatment of RAW 267.4 cells with siRNA to MSR1, FLOT1, and CAV1.
Figure 11:
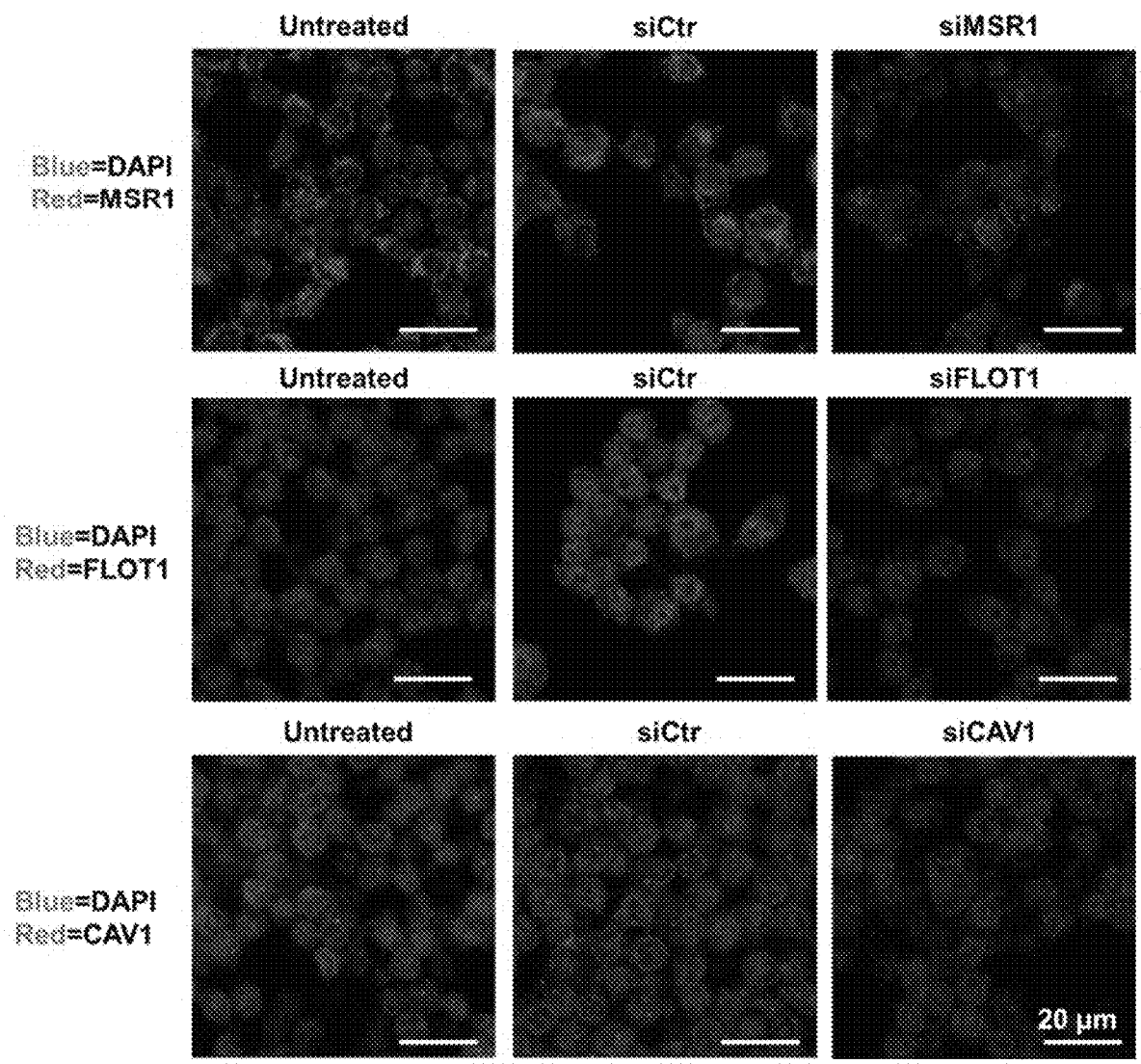
FIG. 11 shows confocal microscopy images of Cy3-labeled MSR1, FLOT1, and CAV1 and DAPI in RAW 264.7 cells after treatment with siRNA to MSR1, FLOT1, and CAV1.
Figure 12:
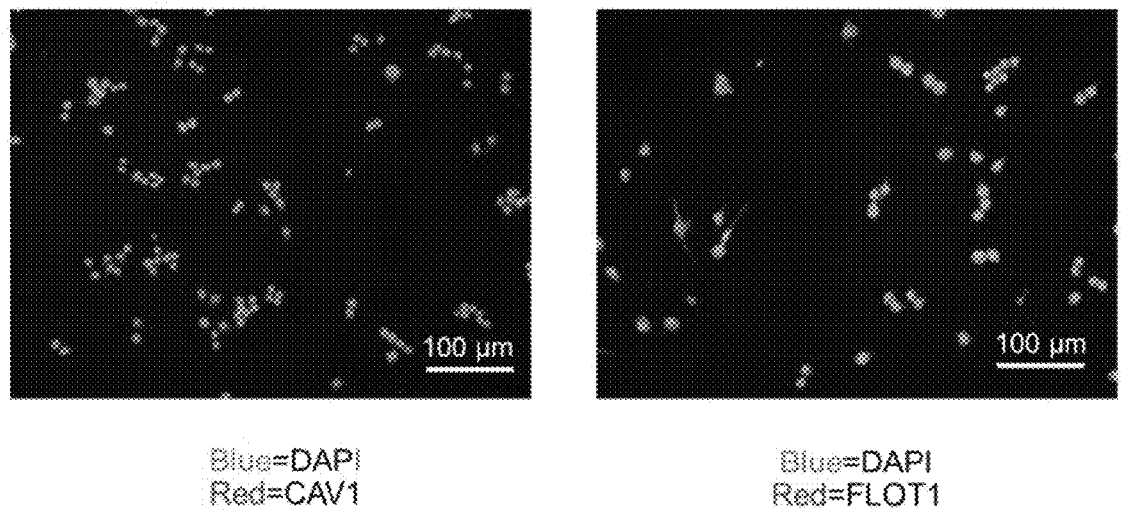
FIG. 12 shows fluorescence microscopy images of RAW 264.7 cells incubated with Cy3-labeled antibodies to CAV1 and FLOT1.
Figure 14A:
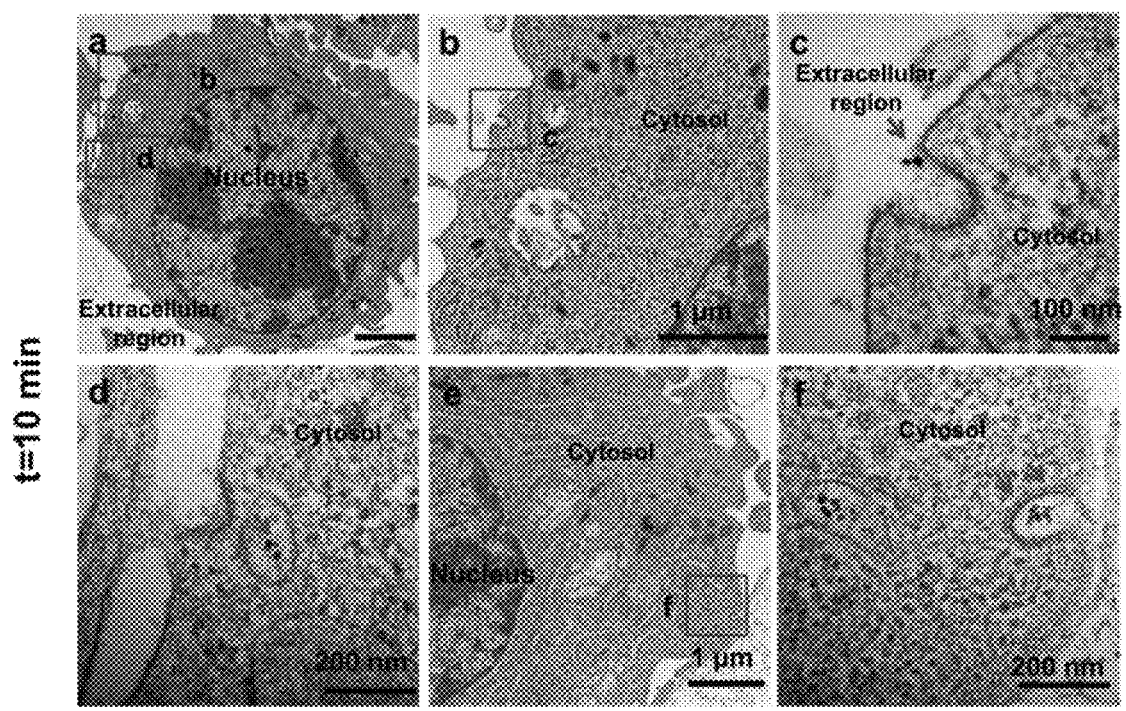
FIG. 14A shows TEM images of the uptake of DNA-SPIONs in RAW 264.7 cells at 10 min after addition of DNA-SPIONs.
Figure 14B:
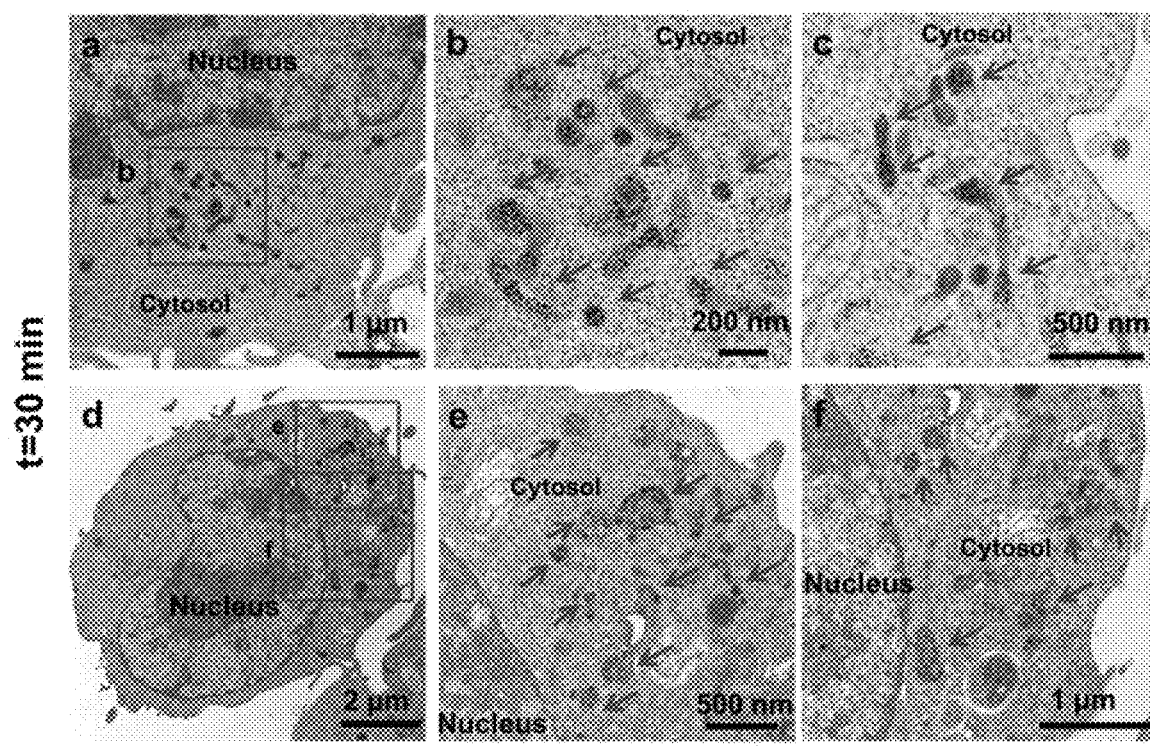
FIG. 14B shows TEM images at 30 min after addition of DNA-SPIONs.
Figure 15A:
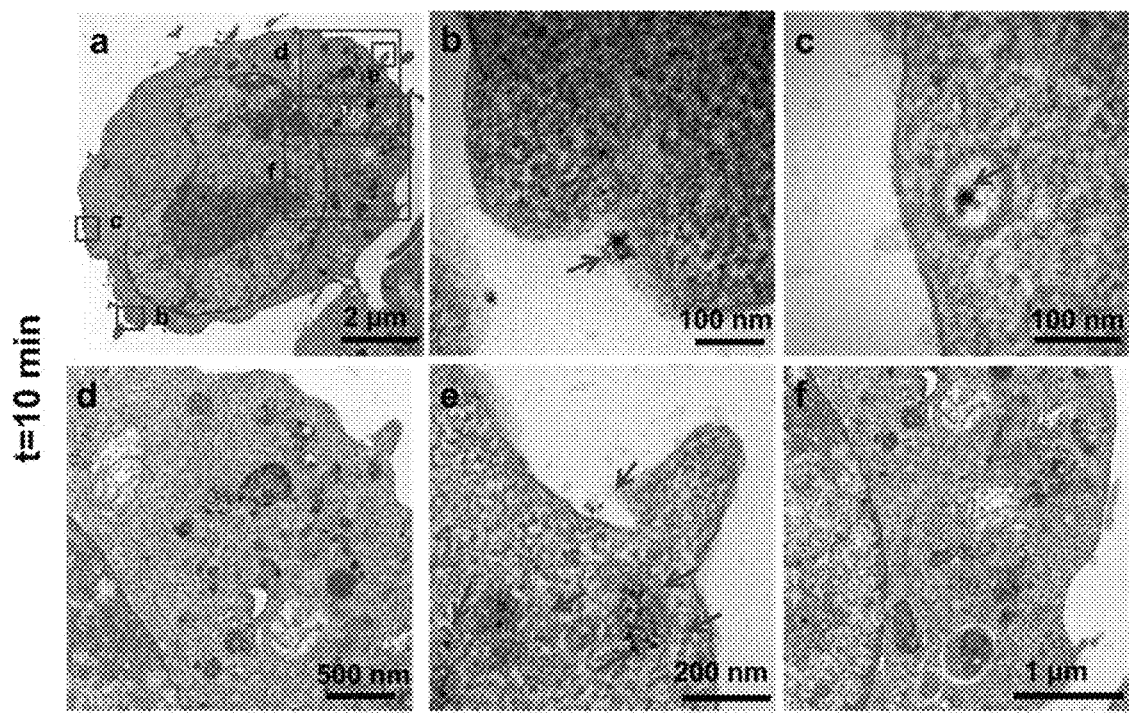
FIG. 15A shows TEM images of the uptake of DNA-SPIONs in RAW 264.7 cells at 10 min after addition of DNA-SPIONs.
Figure 15B:
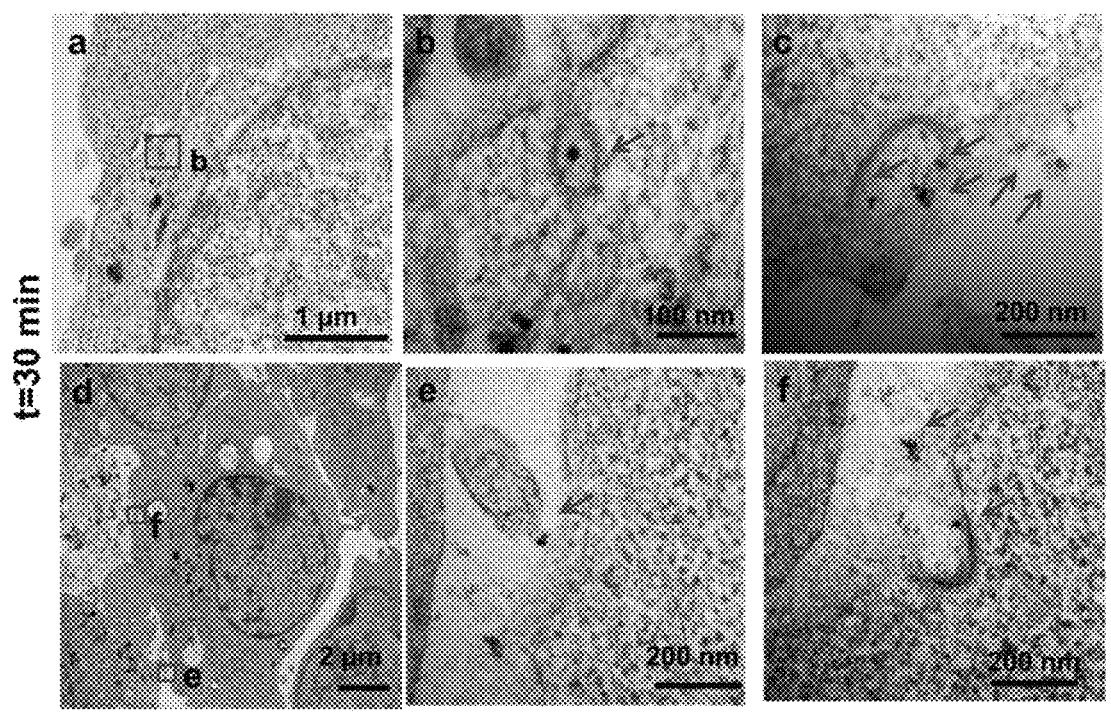
FIG. 15B shows TEM images at 30 min after addition of DNA-SPIONs.

To further address the role of receptors or pathway proteins that govern the uptake of DNA-SPIONs, RAW 264.7 cells were transfected with siRNA that specifically suppressed the expression of the protein in question, followed by probing the cellular uptake of Cy3-DNA-SPIONs by ICP-MS and confocal microscopy. The inhibition of all target proteins after siRNA transfection was confirmed by western blot (FIG. 9D) and confocal immunofluorescence analysis (FIG. 11). After 4 hours of incubation, the iron content of MSR1-siRNA treated RAW 264.7 cells was ~53% less than the cells transfected with no-targeting control siRNA (FIG. 9E). Confocal images of the MSR1-siRNA treated cells following incubation with Cy3-DNA-SPIONs revealed clear attenuation in intracellular Cy3 fluorescence (FIG. 10). From these data, it was concluded that the uptake of DNA-SPIONs in RAW 264.7 cells occured through the association with SR-A and was mediated by lipid-rafts. Because the reduction in the cellular uptake of DNA-SPIONs by SR-A-silenced RAW 264.7 cells was lower than the reduction in the uptake of SNAs by SR-A in silenced C166 cells, which is around 75% (60), the involvement of other cellular uptake pathways was tested. First, TEM images of RAW 2643.7 cells were captured to visualize their uptake of DNA-SPIONs at an early stage. Ten minutes after incubation. DNA-SPIONs began to enter the cells via oval plasma invaginations distinct from clathrin-coated pits or caveolae (FIGS. 14A and 15A). Budding of the plasma membrane, generally, fuses into vesicles that measure less than 200 nm in diameter. Upon 30 min, of incubation, the DNA-SPIONs accumulated inside vesicles throughout the peripheral and perinuclear cytoplasm, which vesicles possessed a round or tubular shape and a size of ~100-200 nm, resembling early endosomes (FIGS. 14B and 15B). These TEM images indicated that DNA-SPIONs translocated from early endosomes to late endosomes as other typical endocytosis processes.

EXAMPLE 5

Noncaveolar Dynamin-Independent Endocytosis is the Main Pathway for Uptake of DNA-SPIONs in Macrophages Next, it was investigated which resident protein in lipid rafts played an important role during the endocytosis. Although the TEM imaging data did not portray caveolae-resembling, flask-shaped invaginations near the cell membrane, it was investigated whether endocytosis of DNA-SPIONs by RAW 264.7 cells depended upon caveolae because caveolae-mediated endocytosis often entails the shuttling of the internalized biomolecules to the early endosomes for further processing (67) and caveolin, a resident protein in the lipid raft, significantly mediates the uptake of SNAs by C166 endothelial cells (61). First, pre-treatment of macrophages with dynasore did not significantly reduce the uptake of SPIONs (FIG. 9A and FIG. 9B), although dynamin II is known to be required for the formation of caveolae (68). Moreover, transient knock down of caveolin 1 (CAV1), the major constituent protein of caveolae (69), only led to ~26% reduction in the cellular association of DNA-SPIONs to RAW 264.7 cells after 4 hours of incubation as determined by ICP-MS (FIG. 9E). Confocal microscopy also showed similar intensity intracellular Cy3 fluorescence inside the CAV1-silenced (CAV-1 siRNA-treated) RAW 264.7 cells and control RAW 264.7 cells transfected with non-targeting control siRNA (FIG. 10). Western blot analysis of the cells harvested 48 h post-transfection showed successful suppression of CAV1, while the cells transfected with control siRNA showed no obvious reduction CAV1 expression compared to untreated cells (FIG. 9D). Taken together, these data demonstrated that caveolae were not significantly involved in the internalization of DNA-SPIONs by RAW 264.7 cells.

Figure 13:
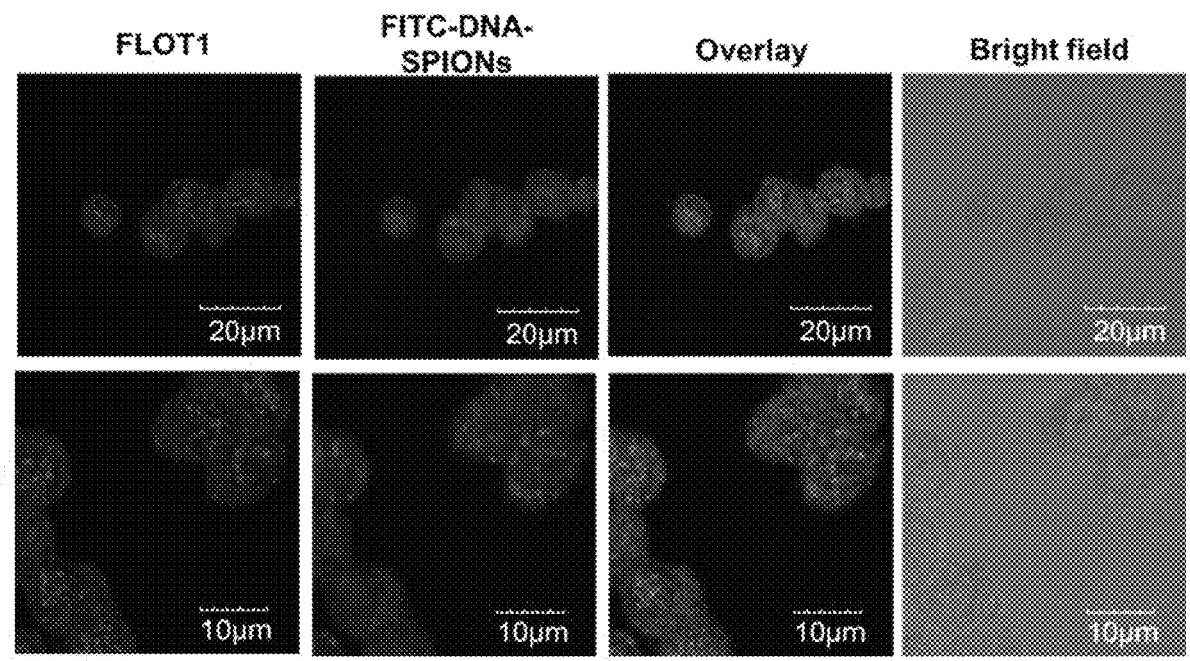
FIG. 13 shows confocal microscopy images of Cy3-labeled antibodies to FLOT1 and FITC-labeled DNA-SPIONs in RAW 264.7 cells 30 minutes after addition of FITC-DNA-SPIONs.

Next, flotillin1 (FLOT1) another common lipid-raft protein that carries functions of cell signaling and endocytosis like caveolin was evaluated. The interest in flotillin1 stemmed from the immunofluorescence data that illustrated more profuse expression of FLOT1 than CAV1 in RAW 264.7 cells (FIG. 11). Again, transient genetic knock down of FLOT1 did not adversely affect the uptake of DNA-SPIONs as evidenced by ICP-MS (FIG. 9E). This result was confirmed by confocal images showing no obvious reduction in the uptake of Cy3-labeled DNA-SPIONs after knock down of FLOT1 (FIG. 10). Again, the siRNA-mediated reduction in FLOT1 expression was confirmed by immunofluorescence staining (FIG. 11). Indeed, the immunofluorescence staining of FLOT1 (Cy3-labeled) after uptake of DNA-SPIONs (FITC-labeled) for 30 min did not show obvious yellow signals, suggesting no obvious co-localization of FLOT1 and DNA-SPIONs (FIG. 13).

Hence, it was concluded that the endocytosis of DNA-SPIONs into RAW 264.7 cells was a lipid raft-dependent, actin-dependent but noncaveloar, dynamin-independent process.

EXAMPLE 6

Intracellular Trafficking of DNA-SPIONs

Figures 16A, 16B, 16C, 16D, 16E:
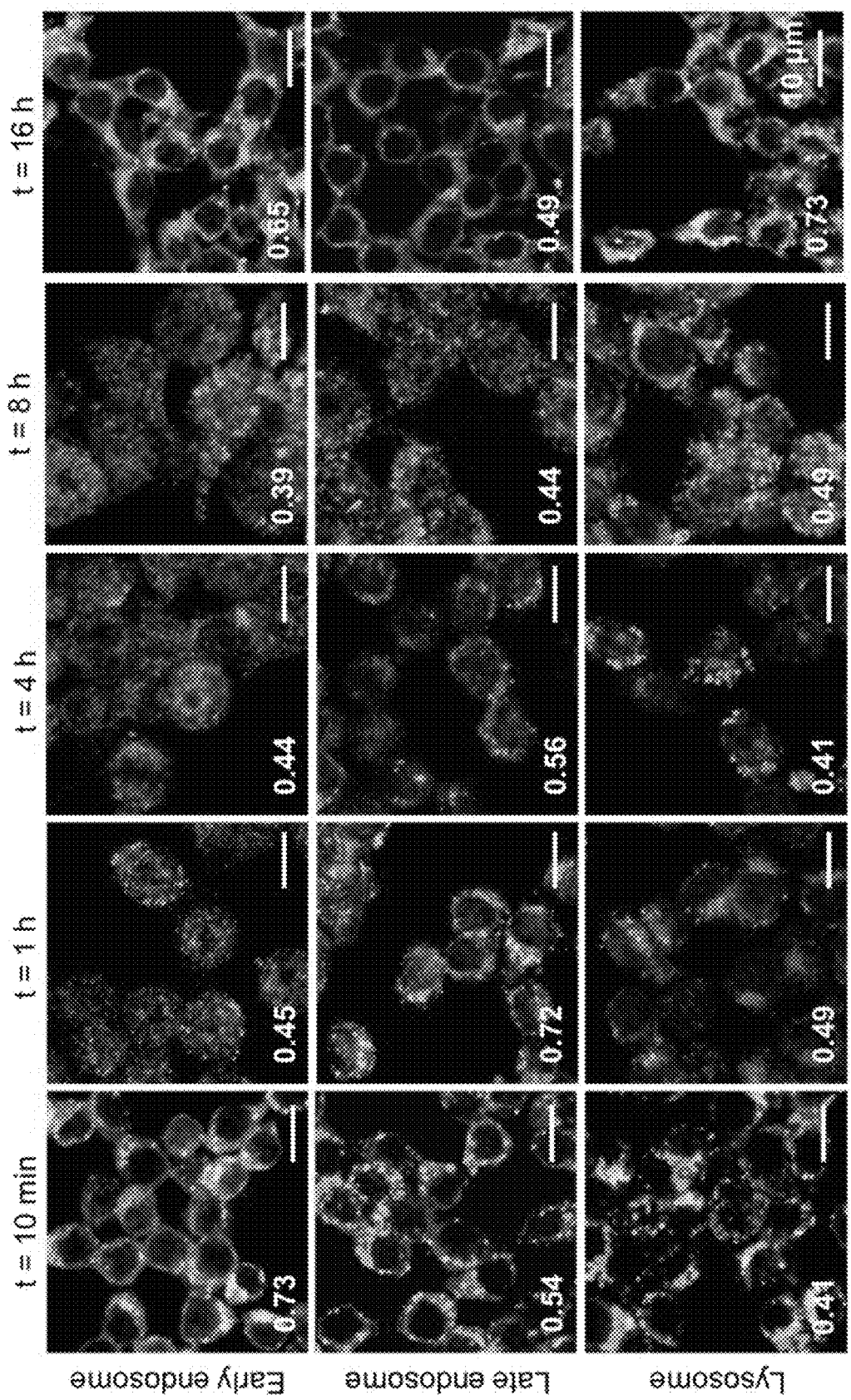
FIG. 16A shows confocal immunofluorescence images of fluorescently-labeled DNA-SPIONs (green) inside RAW 264.7 cells at 10 minutes after addition of DNA-SPIONs.
FIG. 16B shows confocal images at 1h.
FIG. 16C shows images at 4h.
FIG. 16D shows images at 8h.
FIG. 16E shows images at 16 hours.

The intracellular locations of DNA-SPIONs as a function of incubation time in RAW 264.7 cells was studied under conditions where cells were continuously incubated withS-PIONS. To map the intracellular trafficking route of DNA-SPIONs, RAW 264.7 cells were incubated with FITC-DNA- SPIONs for different durations of time followed by performing confocal immunofluorescence to determine their intracellular locations in relation to various protein markers of interest, including the small GTP-binding, Ras-related protein 5 (Rab5), Ras-related protein 9 (Rab9) and lysosomal-associated membrane protein 1 (LAMP1). The corresponding intracellular compartments for Rab5, Rab9, and LAMP1 are early endosome (74), late endosome (75) and lysosome (76). Consistent with the results observed in TEM images, where SPIONs were found predominately in the early endosomes during the early time points after incubation, confocal images after incubation of RAW 264.7 cells with FITC-DNA-SPIONs for 10 min showed high co-localization of FITC-DNA-SPIONs with Rab5 demonstrating accumulation in early endosomes (FIG. 16A). Different from C166 cells (60, 61), most of the DNA-SPIONs already co-localized with Rab9 after incubation for only 1 hour, while only a small fraction of DNA-SPIONs still co-localized with Rab5 in early endosomes (FIG. 16B). These data suggested quicker trafficking of DNA-SPIONs from early endosomes to late endosomes. Four hours post-incubation, fewer numbers of DNA-SPIONs accumulated in the early endosomes and late endosomes, as observed by the decreased Pearson's coefficient of 0.73 (10 min. of incubation) to 0.4 (4 hours of incubation) (FIG. 16C). Beyond the 4-hour time point, the FITC-DNA-SPIONs exhibited moderate co-localization with that of the early and late endosomes, as evidenced by a Pearson's coefficient of 0.4-0.6 for their overlapping fluorescence signals (FIGS. 16D and 16E). These observations supported the notion that the cellular uptake of DNA-SPIONs was a continuous process throughout the entire observation time window of 24 hours. Noticeably, after 16 hours, a large fraction of FITC-DNA-SPIONs was found to co-localize with LAMP1 (biomarker for lysosomes) indicating accumulation in the lysosome (FIG. 16D). These data confirmed that the uptake of DNA-SPIONs in RAW 264.7 cells occurred via the conventional endo-lysosomal route of trafficking that begins at the early endosome, passes by the late endosome, and reaches the lysosome. Thus, the fate of DNA-SPIONs inside RAW 264.7 macrophages differs from those for gold-based SNAs inside C166 endothelial cells (60). In particular, SNAs enter the C166 endothelial cell via the caveolae-mediated pathway, shuttle to the early endosome, and remain in the late endosome without progressing to the lysosome (60). Further, many cargoes and pathogens such as viruses and bacteria are known to enter the cell via the caveolae-mediated pathway to bypass the lysosome and reside in the late endosome (77).

EXAMPLE 7

Blood Pharmacokinetics

Figure 17A:
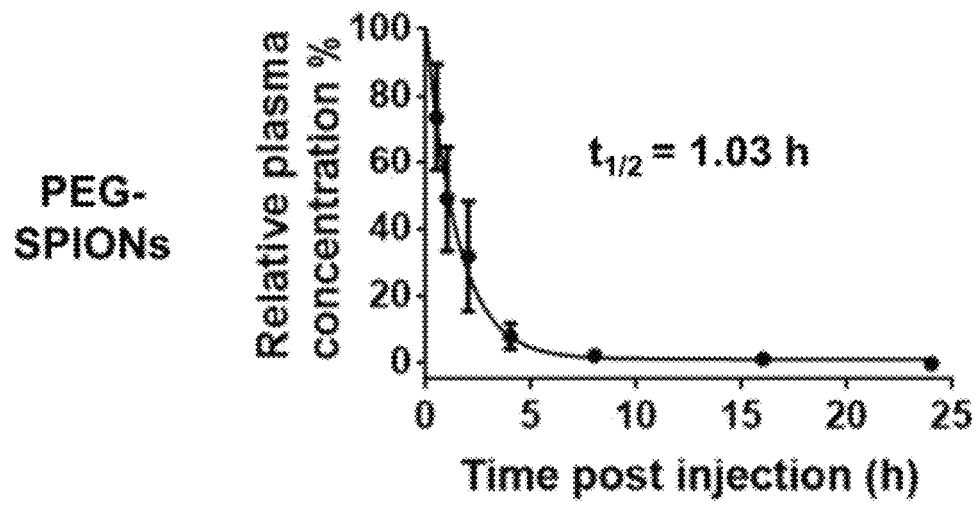
FIG. 17A shows the blood pharmacokinetics of PEG-SPIONs in ApoE−/− mice.
Figure 17B:
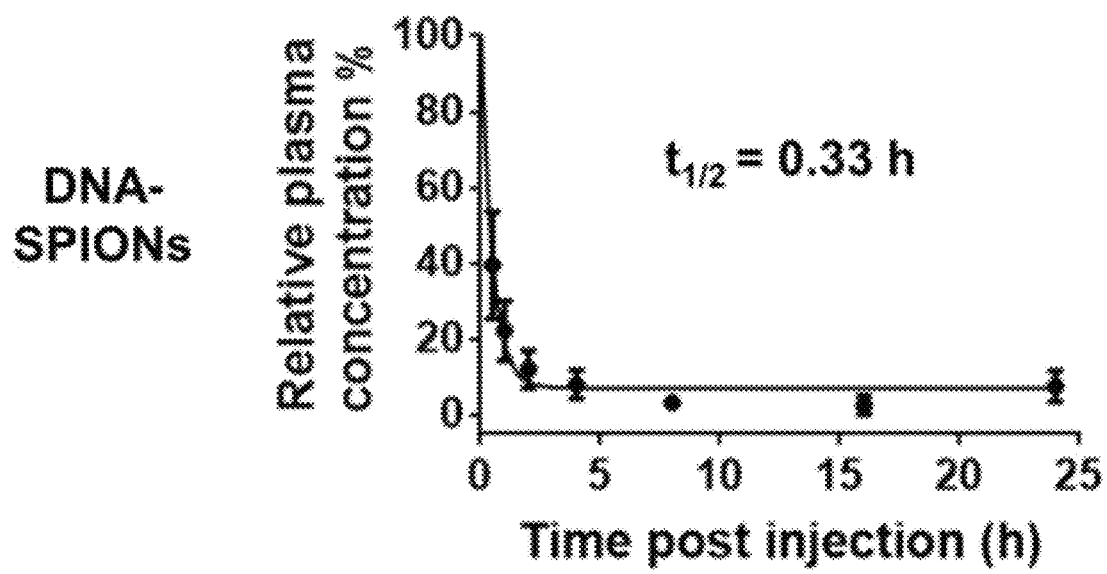
FIG. 17B shows the blood pharmacokinetics of DNA-SPIONs in ApoE−/− mice.
Figure 21:
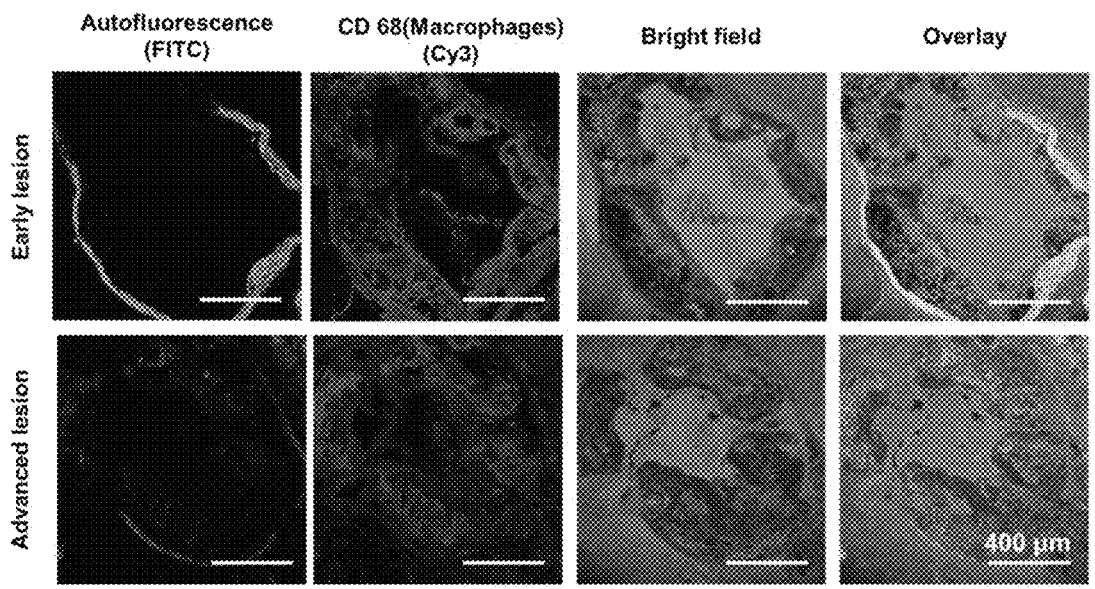
FIG. 21 shows confocal microscopy images of the aortic roots from ApoE−/− mice with early and advanced lesions stained with Cy3-labeled anti-CD68 antibodies for the detection of macrophages.

ApoE$^{-/-}$ mice (n=3) bearing advanced atherosclerotic plaques comprising macrophages (FIG. 21) received a single intravenous (i.v.) injection of both PEG-SPIONs and DNA-SPIONs at the same nanoparticle concentration. To evaluate the blood pharmacokinetics, blood was withdrawn from each mouse through cardiac puncture at various time points to evaluate iron content in blood plasma using inductively coupled plasma optical emission spectrometry (ICP-OES) (FIG. 17A). PEG-SPIONs manifested near mono-exponential blood clearance kinetics with a half-life ($t_{1/2}$) of 1.03 hour (FIG. 17A), which was comparable to a previous report (64). DNA-SPIONs also exhibited mono-exponential blood clearance kinetics like PEG-SPIONs, but the half-life of DNA-SPIONs was only 0.33 hour, i.e., shorter than that of PEG-SPIONs (FIG. 17B). In general, nanoparticles with a highly negative charge distribute to the liver more than neutrally charged nanoparticles or nanoparticles with a weakly negative charge (78). Interestingly, the $t_{1/2}$ of DNA-SPIONs was ~20 times longer than that of classical gold-based SNAs containing no more than 1 mole percent of PEG in their DNA shell (79). Further, based on recent data, SNAs containing higher mole ratios of PEG in the DNA coating exhibited substantially longer $t_{1/2}$ than those containing lower mole ratios (79). For DNA-SPIONs of the subject invention, the DNA oligonucleotides were attached to the periphery of the PEG-SPIONs and not directly on the surface of unmodified SPION cores.

EXAMPLE 8

Organ-Level Biodistribution of PEG-SPIONs and DNA-SPIONs in ApoE$^{-/-}$ mice

Figure 17C:
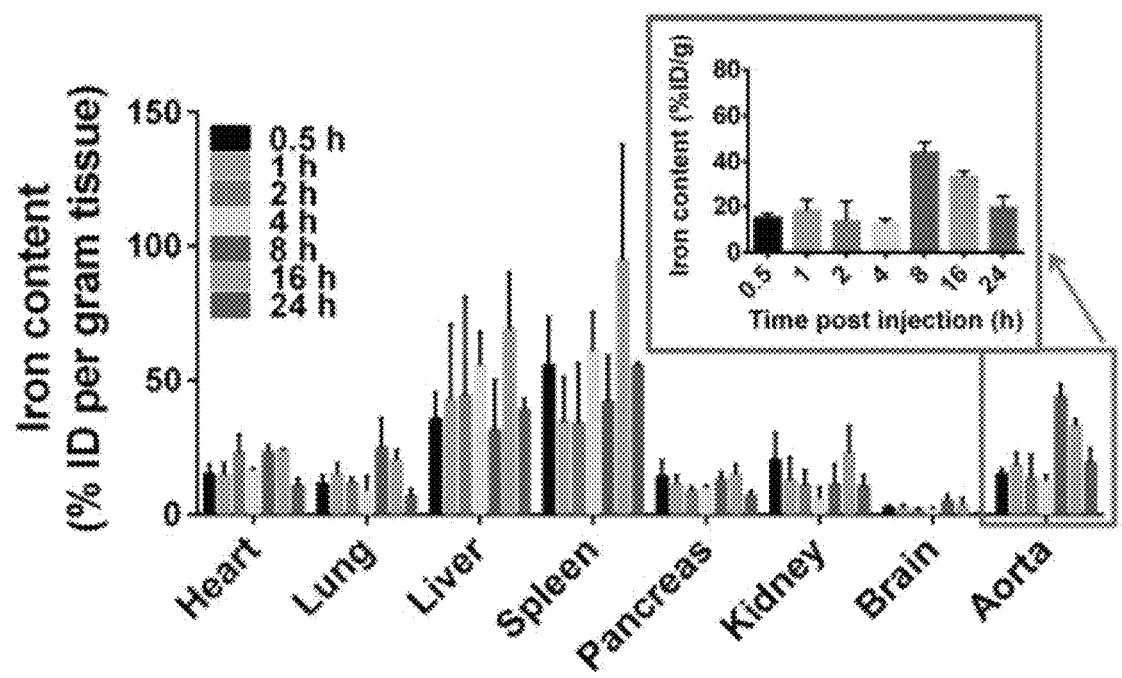
FIG. 17C shows the biodistribution of PEG-SPIONs in different organs following i.v. injection.
Figure 17D:
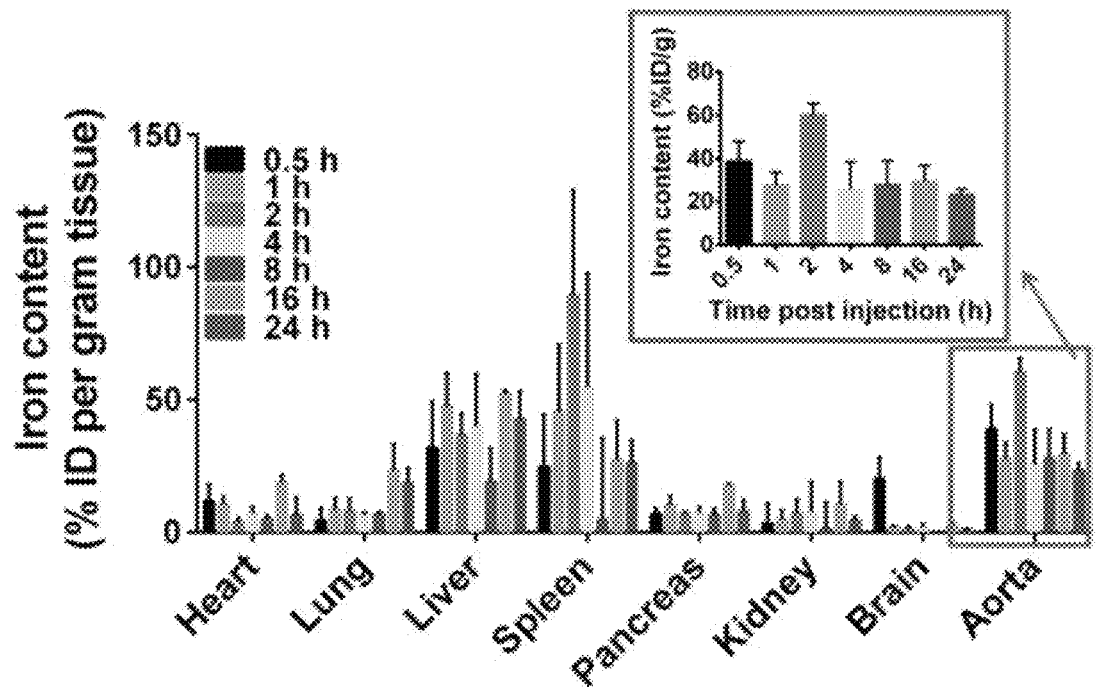
FIG. 17D shows the biodistribution of DNA-SPIONs in different organs following i.v. injection.
Figure 17E:
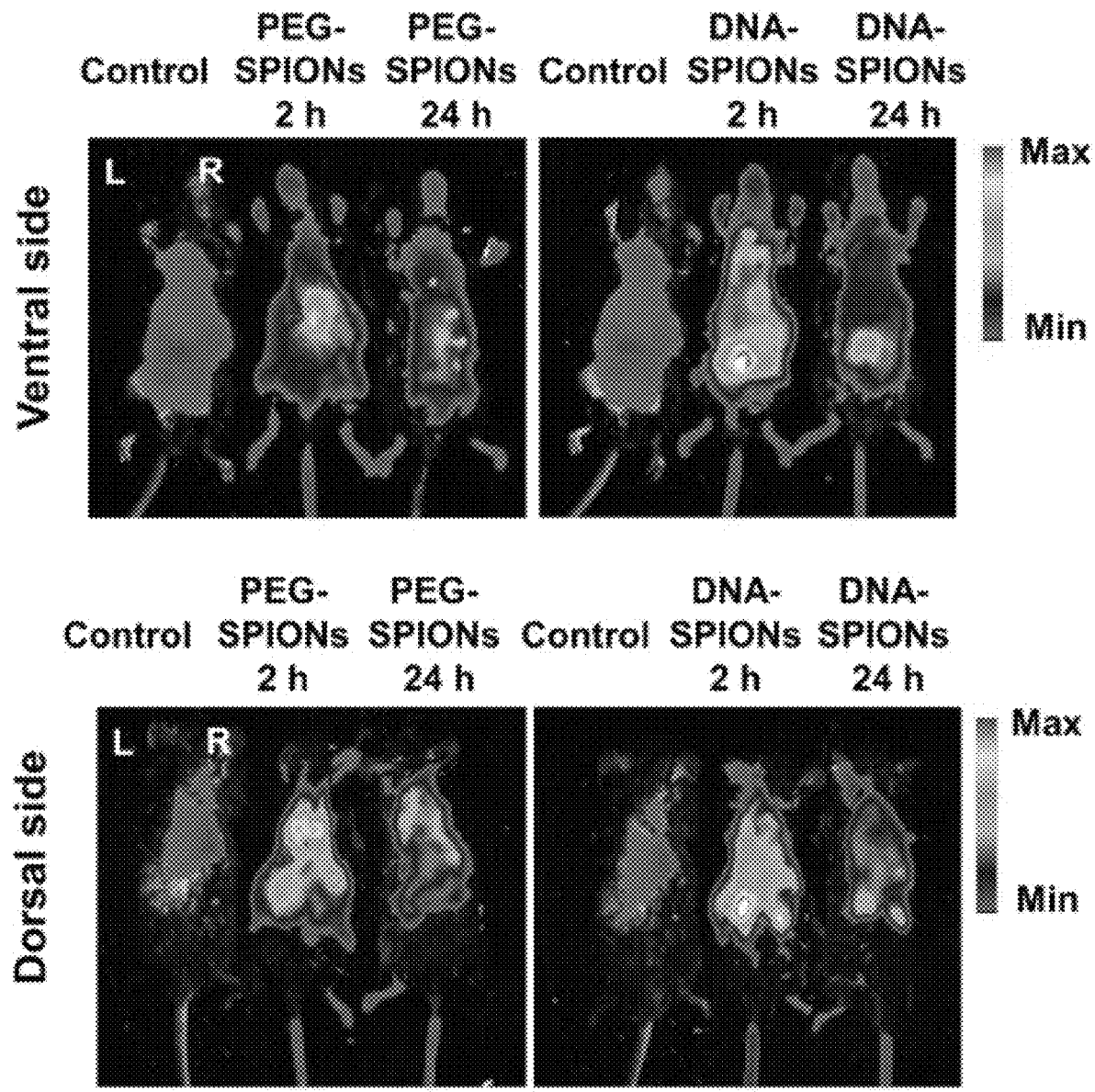
FIG. 17E shows in vivo NIRF imaging of ApoE$^{-/-}$ mice injected with Cy5.5-PEG-SPIONS and Cy5.5-DNA-SPIONs.
Figure 17F:
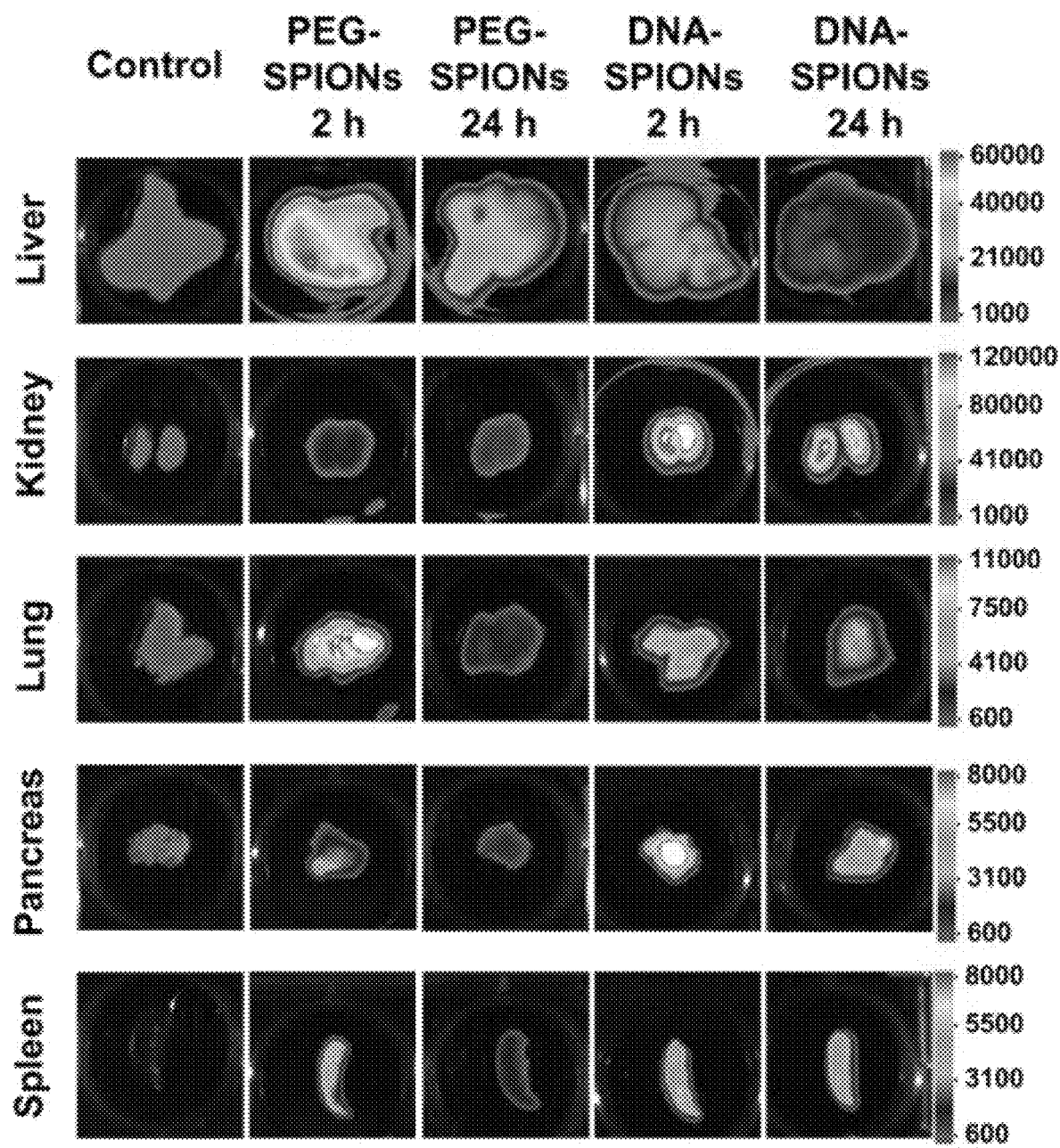
FIG. 17F shows ex vivo NIRF imaging of organs collected from ApoE$^{-/-}$ mice injected with Cy5.5-PEG-SPIONS and Cy5.5-DNA-SPIONs
Figure 18A:
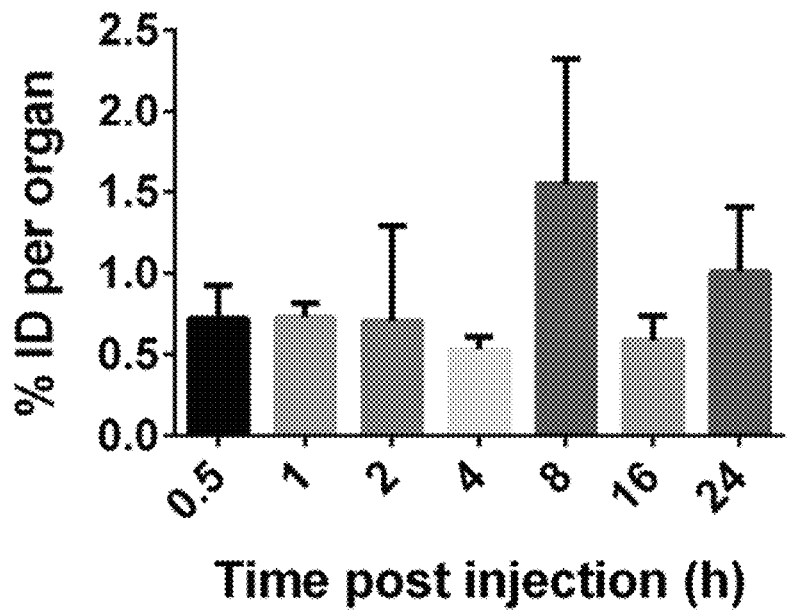
FIG. 18A shows the accumulation of PEG-SPIONs in aortas of ApoE−/− mice with advanced atherosclerotic lesions at different time points after nanoparticle injection by measuring the iron content with ICP-MS.
Figure 18B:
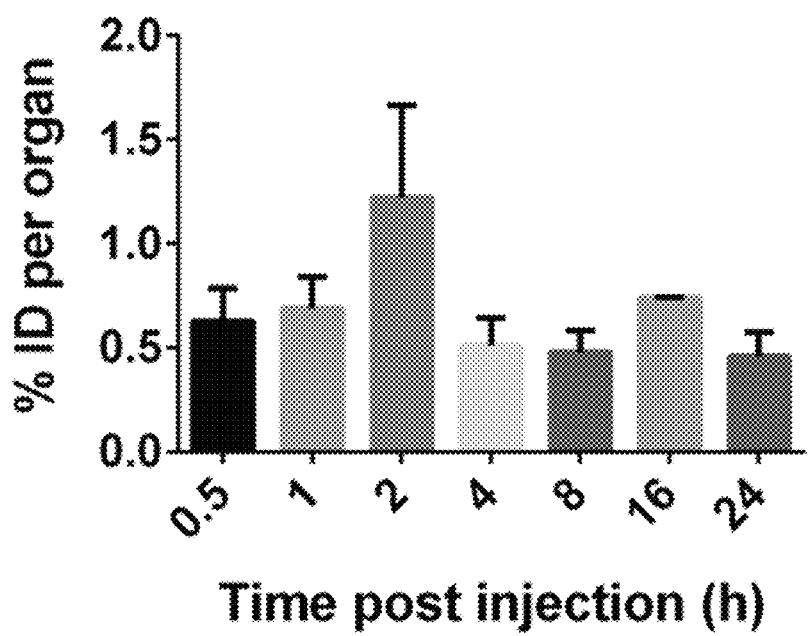
FIG. 18B shows the accumulation of DNA-SPIONs in aortas of ApoE−/− mice with advanced atherosclerotic lesions at different time points after nanoparticle injection by measuring the iron content with ICP-MS.

Organ-level biodistribution was ascertained using ICP-OES to measure concentrations of SPION cores in the aorta and other internal organs at different time point post injection. ApoE$^{-/-}$ mice were euthanized at different time points after injection of PEG- and DNA-SPIONs to extract organs for detection of iron content using ICP-OES. In terms of accumulation of SPIONs on a per gram tissue basis, PEG-SPIONs and DNA-SPIONs accumulated the most in liver and spleen, i.e., organs of the mononuclear phagocyte system (MPS) for all time points tested with iron contents amounting to 31-69% injected dose (ID)/g in the liver and 33-61% ID/g in the spleen for both SPION types (FIGS. 17C and 17D). Accumulation of PEG- and DNA-SPIONs in the pancreas, brain, lungs, kidneys, and heart were negligible with iron contents in each organ amounting to no more than 20% ID/g. Splenic iron content, displayed as % ID per gram of tissue, was even higher than that in the liver for both types of SPIONS, which is consistent with previous reports (79, 80). Trailing behind the liver and spleen was the aorta with iron contents of 12-40% ID/g for PEG-SPIONs and 10-60% ID/g for DNA-SPIONs (FIGS. 17C, insert, and 17D, insert). Interestingly, the lung and kidney data displayed slightly elevated iron levels at all time points for the PEG-SPION group, probably due to longer circulation and passive targeting properties. Meanwhile, the uptake into the aorta shown as % ID per gram, was much higher than, e.g., in non-MPS organs suggesting the advanced targeting efficacy into atherosclerotic lesions for both PEG-SPIONs and DNA-SPIONs. The accumulation of both PEG-SPIONs (FIG. 18A) and DNA-SPIONs (FIG. 18B) in isolated aortas of ApoE$^{-/-}$ mice was also determined in terms of percent injected dose (% ID) per aorta (FIG. 18). The maximal accumulation of PEG-SPIONs was 1.0% ID/aorta (FIG. 18A) and of DNA-SPIONs was 1.2% ID/aorta (FIG. 18B) and occurred at ~8 hours post injection for PEG-SPIONs and ~2 hours post injection for DNA-SPIONs, respectively (FIGS. 18A and 18B). These data demonstrated enhanced and accelerated delivery of DNA-SPIONs, due to the DNA coating, to the aorta, a major site of atherosclerotic plaques in ApoE$^{-/-}$ mice and humans suffering from atherosclerotic disease. Despite the amount of nanoparticles available for aortic uptake, the targeting kinetics of atherosclerotic plaques is another key parameter of targeting imaging agents, especially for translational purposes. It is known that the uptake of the iron oxide nanoparticles by the macrophages in MPS organs is usually preceded by opsonization, i.e., recognition by the macrophages and phagocytosis (76). Hence, the blood circulation time is closely related to the organ-level distribution rate of nanoparticles. As expected, DNA-SPION accumulation in both liver and spleen reached maximum levels 2 hours post administration, due to their shorter blood circulation (FIG. 17D). PEG-SPIONs, on the other hand, needed 16 hours to reach maximal accumulation in liver and spleen (FIG. 17C). Similarly, the targeting and accumulation of PEG-SPIONs and DNA-SPIONs to atherosclerotic aortic regions matched with that to MPS organs, requiring 8 hours for PEG-SPIONs and 2 hours for DNA-SPIONs for maximal accumulation, respectively (FIG. 17C, insert, and FIG. 17D, insert). Taken together, these data indicated that DNA-SPIONs targeted the atherosclerotic plaques in a more timely manner than the PEG counterparts.

EXAMPLE 9

Near Infrared Imaging of SPIONs In Vivo and Ex Vivo

Next, the in vivo distribution of Cy5.5-tagged SPIONs was examined using near infrared fluorescence imaging (NIRF) in mice with early and advanced atherosclerotic lesions (ApoE$^{-/-}$ mice). The same EDC/MHS chemistry as discussed about for Cy3-SPIONS was used to prepare Cy5.5-tagged PEG-SPIONs and Cy5.5-tagged DNA-SPIONs for their i.v. injection into ApoE.$^{-/-}$ mice followed by in vivo NIRF imaging of the animals (FIG. 19A) and ex vivo imaging of the excised organs (FIG. 19B). For mice injected with Cy5.5-PEG-SPIONs, intense fluorescence was detected in the lungs and near the liver 0.5 hours and 2 hours after injection but not the kidneys and bladder (FIG. 19B, left panels). By ex vivo NIRF imaging, the most intense Cy5.5 fluorescence following Cy5.5-PEG-SPION injection was detected in the liver among all organs, scoring a maximum fluorescent intensity level of $6 \times 10^4$. In descending order of fluorescence intensity, other organs with accumulation of Cy5.5-PEG-SPIONs were the kidneys, lungs, spleen, and pancreas (FIG. 19B, left panels).

Figure 19A:
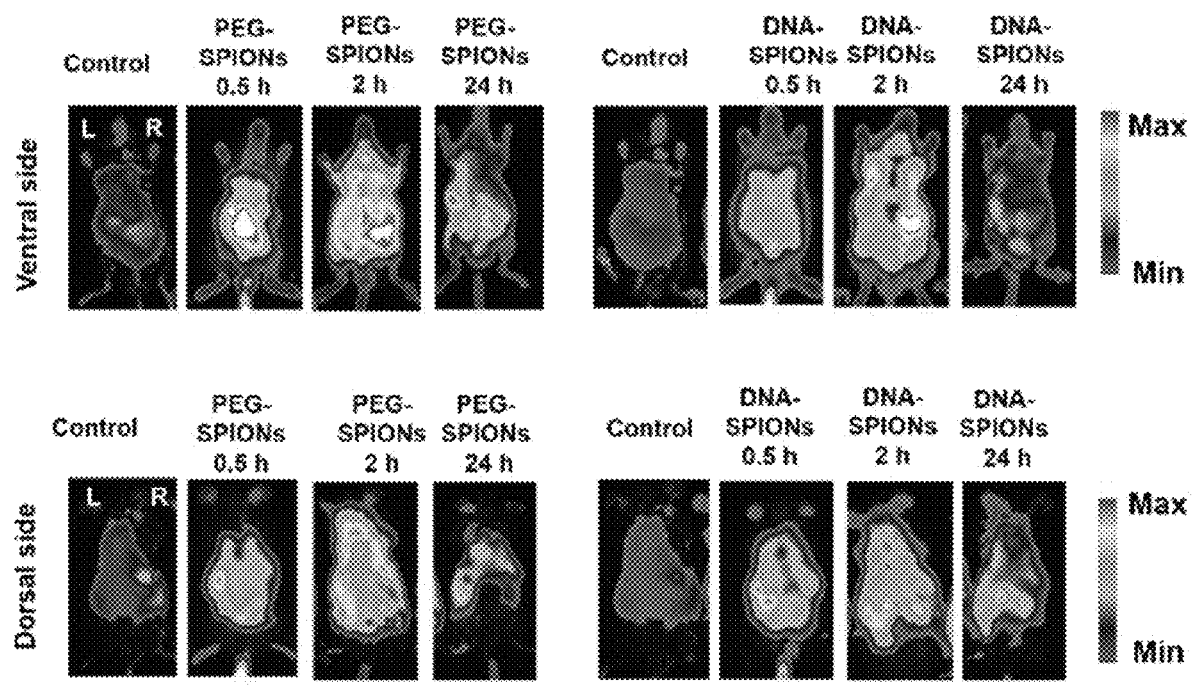
FIG. 19A shows in vivo near-infrared fluorescence (NIRF) imaging of ApoE−/− mice with early atherosclerotic lesions 0.5 hours, 2 hours, and 24 hours after injection of Cy5.5-tagged PEG-SPIONs and DNA-SPIONs in the front and back views.
Figure 19B:
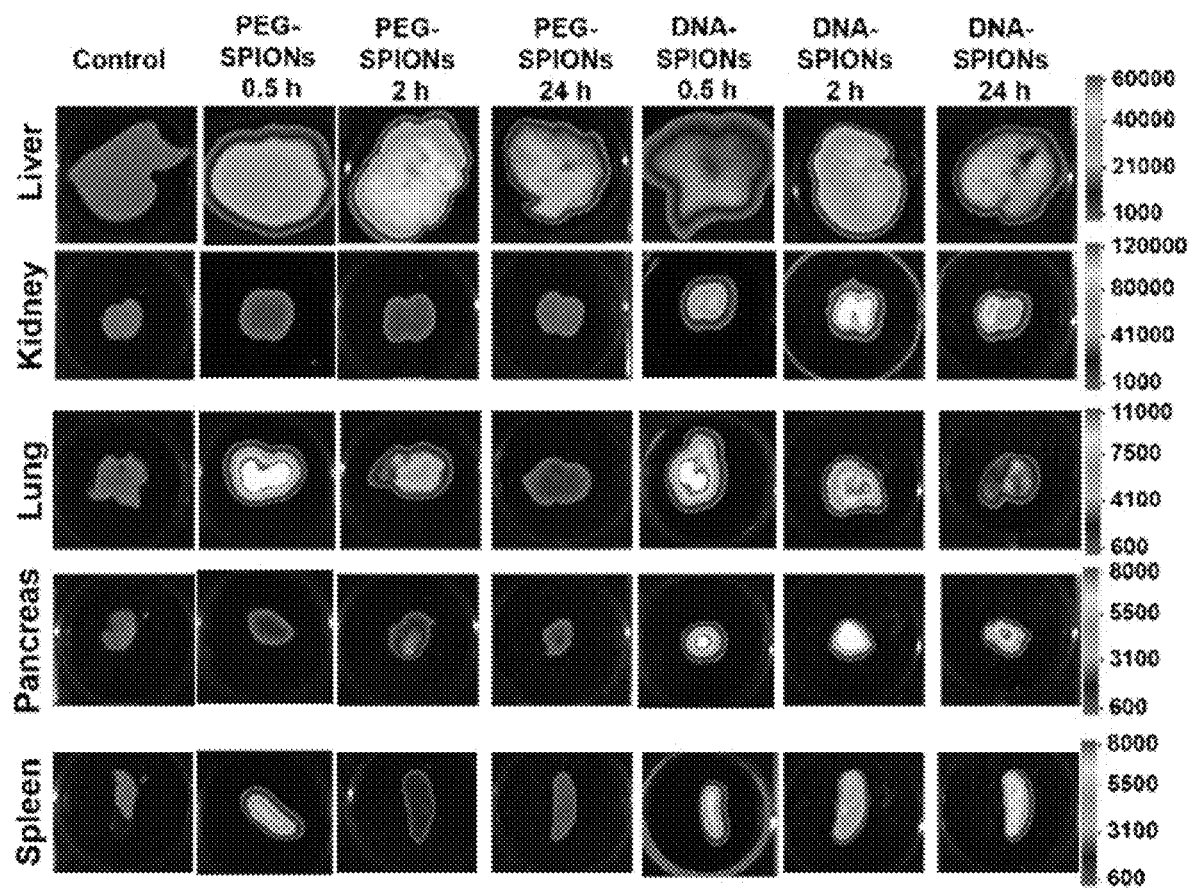
FIG. 19B shows ex vivo near-infrared fluorescence (NIRF) imaging of different organs of ApoE−/− mice with early atherosclerotic lesions 0.5 hours, 2 hours, and 24 hours post intravenous injection of Cy5.5-tagged nanoparticles.

In contrast, for the Cy5.5-DNA-SPION group in vivo NIRF imaging showed the strongest fluorescence in the kidneys and bladder instead of the lung and liver 0.5 hours and 2 hours after Cy5.5-DNA-SPION injection (FIG. 19A, right panels). Ex vivo imaging showed the strongest Cy5.5 fluorescence following Cy5.5-DNA-SPION injection in the kidneys (over $1.2 \times 10^5$), followed by the liver (~$4.5 \times 10^4$) and pancreas, lungs, and spleen (FIG. 19B, right panels). Twenty-four hours post-injection, in vivo NIRF imaging revealed that mice injected with both PEG- and DNA-SPIONs showed organ-level distribution patterns similar to their corresponding patterns 0.5 hours and 2 hours post-injection, albeit at markedly attenuated fluorescence intensities (FIG. 19A). For the DNA-SPION treatment group, the Cy5.5 fluorescence in the kidneys remained the strongest among other organs tested. Ex vivo NIRF imaging showed that the fluorescence in the kidneys for the Cy5.5-DNA-SPION treatment group still peaked at $1.2 \times 10^5$ after 24 hours of injection, followed by the liver, lungs, spleen, and pancreas (FIG. 19B, right panels). Interestingly, whereas ICP-OES data revealed the liver as the primary site of accumulation of the SPION cores 2 hours post-injection (FIG. 17B), the NIRF imaging data suggested the presence of Cy5.5-tagged DNA strands in the kidneys and bladder (FIGS. 19A and 19B). The mean physical diameter of the SPION core (16 nm), the mean hydrodynamic size of PEG-SPIONs (41 nm), and the mean hydrodynamic diameter of DNA-SPIONs (55 nm) are all in excess of the threshold size of 10 nm governing the renal clearance of nanoparticles (81). Because NIRF imaging did not reveal noticeable Cy5.5 fluorescence in the kidneys or bladder for the PEG-SPIONs treatment group, the data indicated the in vivo detachment of some DNA strands from the SPION cores and/or degradation of the DNA strands into smaller fragments starting at 0.5 hours and more pronounced at 2 hours post-injection (FIGS. 19A and 19B). These DNA fragments, typically 3-4 nm in diameter (82) can penetrate the glomerular filtration barrier (83) and traverse the bladder, and eventually exit the body. Twenty-four hours post-injection, the NIRF imaging data also indicated accumulation of at least some dissociated Cy5.5-tagged DNA fragments (or only Cy5.5 molecules) inside the kidneys.

In general, attachment of Cy5.5 to biomolecules can significantly alter their organ-level distribution. For example, Kimura et al. showed that i.v. injected Cy5.5-tagged knottin peptides could accumulate in the kidneys within 2 hours of injection and remained in the kidneys up to 24 hours post-injection, yet non-fluorescent knottin peptides could not (84, 85). The effect of kidney accumulation appeared to be specific to Cy5.5, because no higher radioactivity in the kidneys was observed when Cy5.5 was substituted with Cu64-labeled 1,4,7,10-tetraazacyclododecane-1,4,7,10-tetraacetic acid (DOTA) for positron emission tomography (PET) (84, 85).

The above studies underscore an integrated application of ICP-OES analysis and NIRF imaging to provide complementary insights into the organ-level distribution of PEG- and DNA-SPIONs. The results of the studies indicated that PEG-SPIONs were generally stable over the course of 24 hours, with a slightly longer circulation half-life than DNA-SPIONs. For DNA-SPIONs, some of the DNA strands originally attached to the SPION cores experienced in vivo disassembly or degradation as soon as 0.5 hours and 2 hours post-injection leading to their renal clearance out of the body or retention in the kidneys for at least 24 hours (see, e.g, FIG. 19B, right panels).

EXAMPLE 10

In Vivo Delivery to Atherosclerotic Plaques of ApoE$^{-/-}$ mice

Figure 20A:
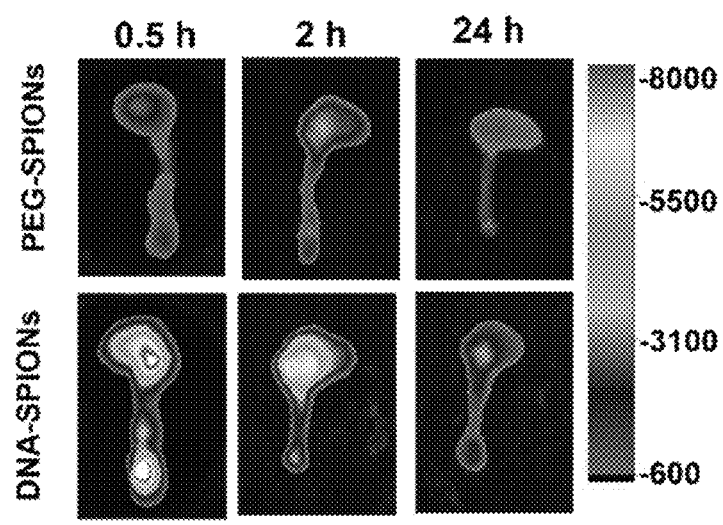
FIGS. 20A through 20G show the cellular-level distribution of PEG-SPIONs and DNA-SPIONs in the heart and aorta of ApoE$^{-/-}$ mice.
Figure 20B:
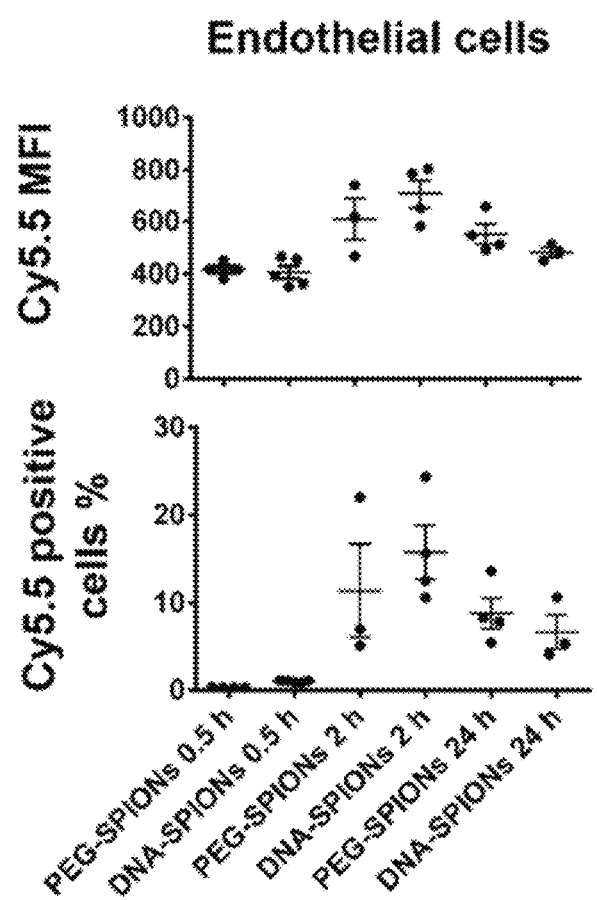
Figure 20C:
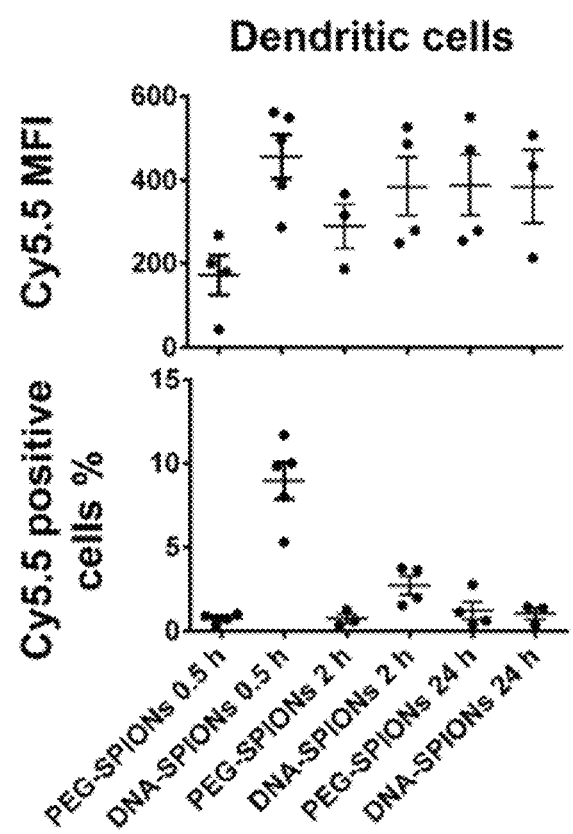
Figure 20D:
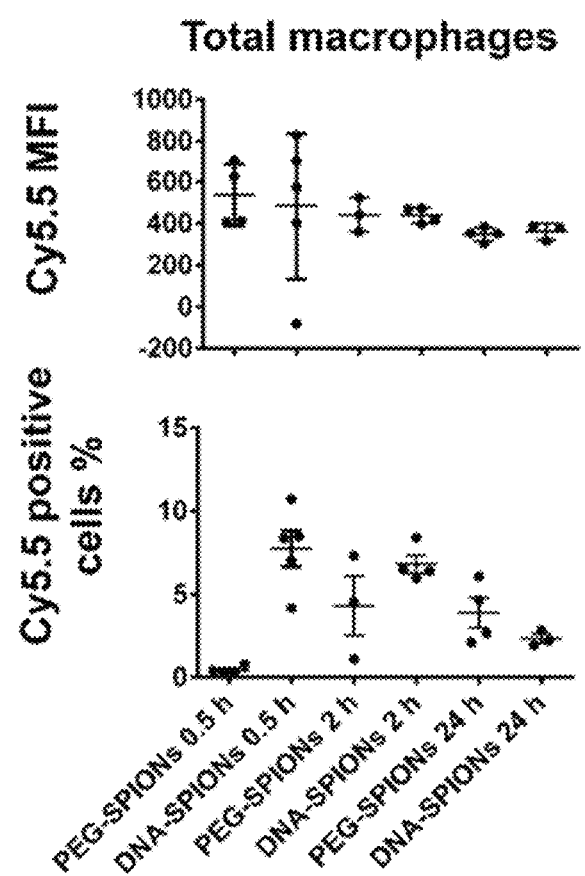

In vivo delivery to atherosclerotic plaques of ApoE$^{-/-}$ mice was ascertained in the aorta. Accumulation of Cy5.5-DNA-SPIONs in plaques of the aorta was faster and higher than PEG-SPIONs, starting at 0.5 hours post-injection as detected by ex vivo NIRF imaging (FIG. 20A). Thirty minutes post-injection, ex vivo NIRF imaging revealed 3-fold stronger peak fluorescence in the hearts and aortas from the Cy5.5-DNA-SPION injection group compared to the Cy5.5-PEG-SPION injection group (FIG. 20A, left panels). Twenty-four hours post-injection, the Cy5.5 fluorescence was weaker in the hearts and aortas of both Cy5.5-PEG-SPION and Cy5.5-DNA-SPION treated animals (FIG. 20A, right panels) than those detected 0.5 hours and 2 hours post-injection (FIG. 20A, left and middle panels), although the peak fluorescence for the DNA-SPION injection group was still 4-fold more intense than the peak fluorescence for the PEG-SPION injection group (FIG. 20A). Cy5.5 fluorescence "hot spots" were detectable in the hearts and aortas, which hot spots were not uniformly distributed across the tissue suggesting the detection of spatially defined plaques that could be more effectively targeted by DNA-SPIONs than PEG-SPIONs (FIG. 20A). These ex vivo NIRF imaging data reinforced the ICP-OES data on the organ-level aortic accumulation of SPION cores (FIGS. 17C, inserts, and 17D, insert and FIGS. 18B and 18B).

Therefore, when benchmarked against PEG-SPIONs, accumulation of DNA-SPIONs in the aorta was more abundant (~60% ID/g for DNA-SPIONS versus ~44% ID/g for PEG-SPIONs in terms of peak iron contents, or ~1.2% ID per aorta for DNA-SPIONs versus ~1.0% ID per aorta for PEG-SPIONs; FIGS. 18A and 18B) and faster, i.e., reached peak iron contents in aortas 2 hours post-injection versus 8 hours post-injection (FIGS. 17C, insert, and 17D, insert). Similarly, Cy5.5-DNA-SPION accumulation was faster in hearts and aortas compared to Cy5.5-PEG-SPION accumulation, i.e., reached peak fluorescence 0.5 hours post-injection versus 2 hours post-injection (FIG. 20A). After the aortas were collected and sectioned, the Cy5.5-DNA-SPIONs were detected extensively in the aortic plaques at 0.5 hours post injection in mice with both early and advanced atherosclerotic lesions as indicated by the intensive red signals (FIG. 20G), while PEG-SPIONs did not show accumulation at such early time point but were detected at later time points (FIG. 20G). After staining with CD 68, a biomarker of macrophages abundantly present in early and advanced atherosclerotic lesions (FIG. 21), the red and green signals confirmed partial co-localization of PEG- and DNA-SPIONs with macrophages in the plaques (FIG. 20G), which suggested macrophages played an important role in the delivery process.

EXAMPLE 11

Figure 28:
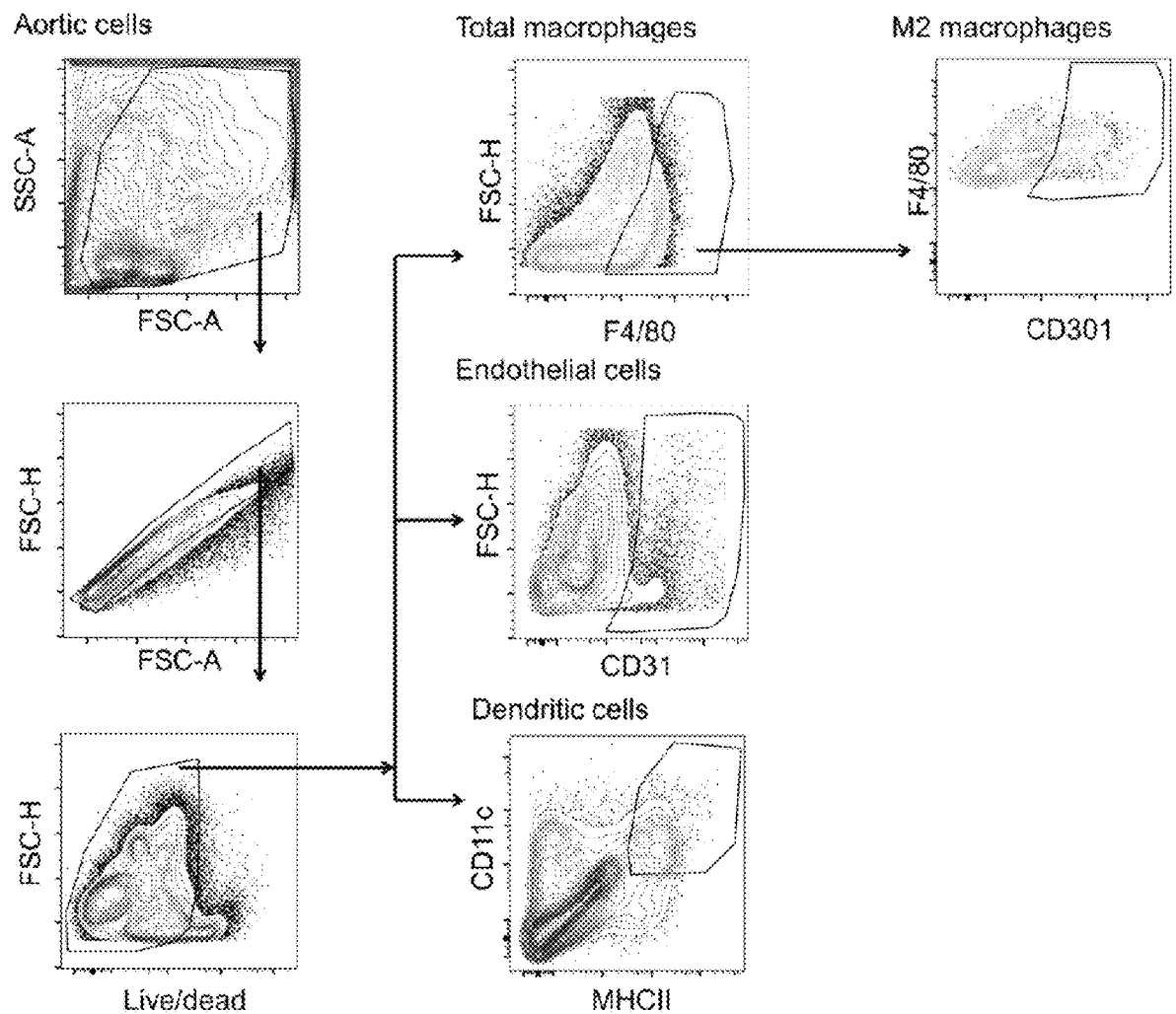
FIG. 28 shows the gating strategy used for flow cytometric analysis of single cell suspensions from aortic cells of ApoE$^{-/-}$ mice.

Cellular-Level Biodistribution of PEG- and DNA-SPIONs in Atherosclerotic Plaques To further investigate the interactions of PEG- and DNA-SPIONs with the main types of cells in the aortic plaques, biomarkers were used to label endothelial cells, macrophages (including M2 subtype) and dendritic cells isolated from aortas of ApoE$^{-/-}$ mice and analyzed by flow cytometry. The uptake of Cy5.5-PEG- and Cy5.5-DNA-SPIONs in each cell type present in aortic plaques were evaluated by both the percentage of Cy5.5 positive cells and MFI of the Cy5.5 fluorophore in the cells. A specific gating strategy was used for aortic cells isolated from the aortas (FIG. 28). A single cell suspension from the aorta was gated on FSC-A and SSC-A to exclude cell debris. Singlets were gated on Live/Dead Aqua on AmCyan to the live cell population. From this point, cells were separated in different staining panels for macrophages on F4/80, endothelial cells on CD31, and dendritic cells positive on CD11c and MHCII. F4/80+ macrophages were further gated on CD301 for M2 (CD301+) macrophages (FIG. 28).

Figure 20E:
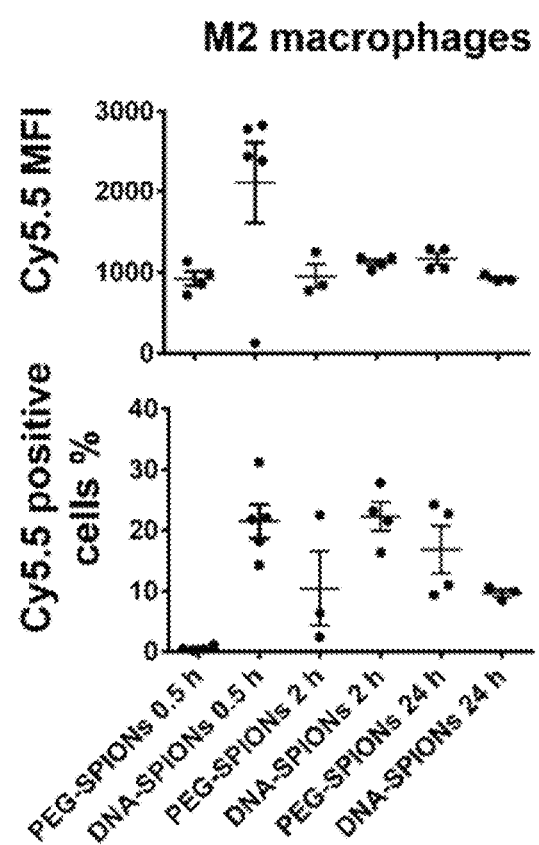
Figure 20F:
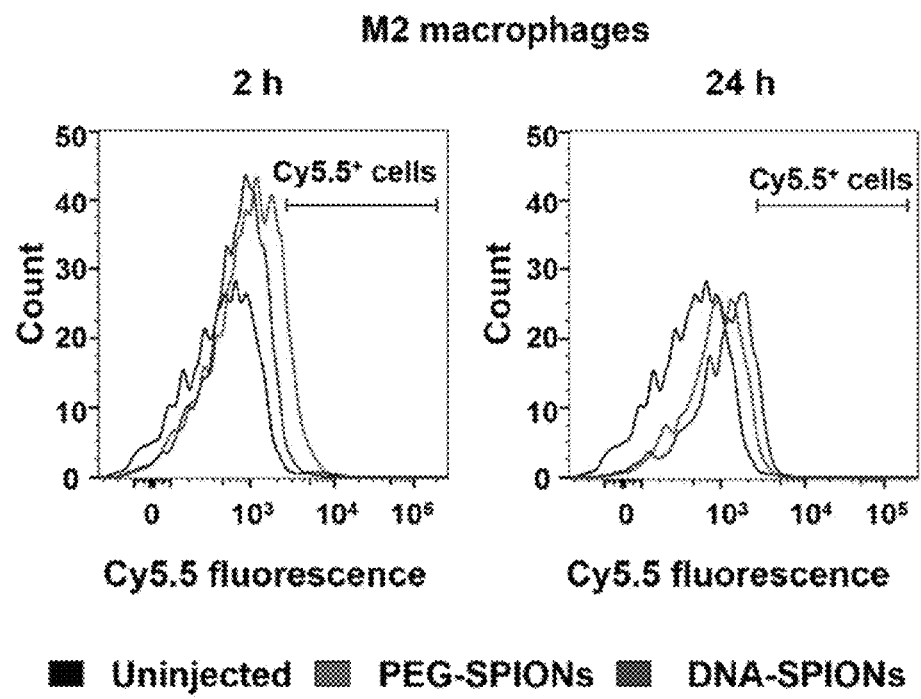
Figure 20G:
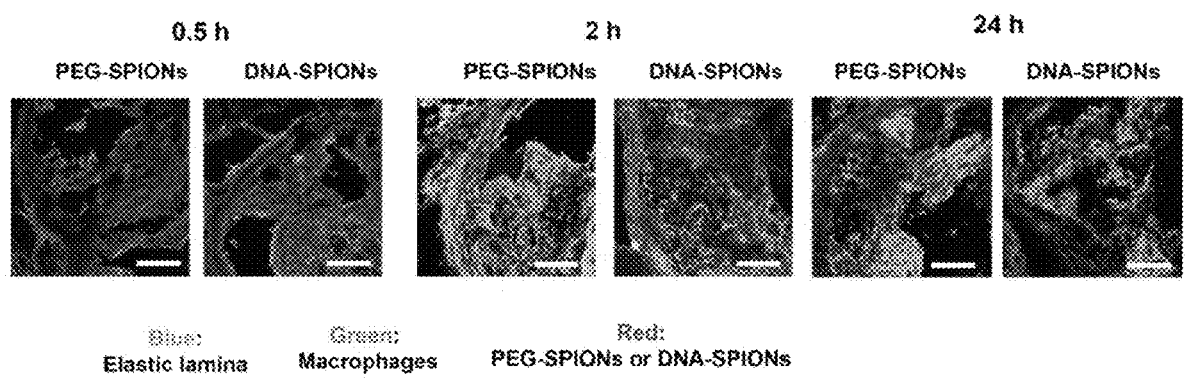

Both sets of data showed that aortic plaque macrophages had the highest uptake of SPIONs, irrespective of the nature of coating on the SPIONs, at 0.5 hours and 2 hours after intravenous injection (FIGS. 20B, 20C, 20D and 20E). Especially, M2 macrophages of aortic plaques had a very high uptake of Cy5.5-DNA-SPIONs 0.5 hours and 2 hours after injection (FIGS. 20E and 20F). In terms of uptake kinetics, Cy5.5-DNA-SPIONs entered each cell type more potently and more rapidly indicated by the highest MFI of Cy5.5-DNA-SPIONs in all cell types at 0.5 hours and 2 hours post injection (FIG. 20b, 20C, 20D, 20E, and 20F).

EXAMPLE 12

Cellular-Level Biodistribution of PEG- and DNA-SPIONs in Selected Organs in ApoE$^{-/-}$ Mice.

Figure 25:
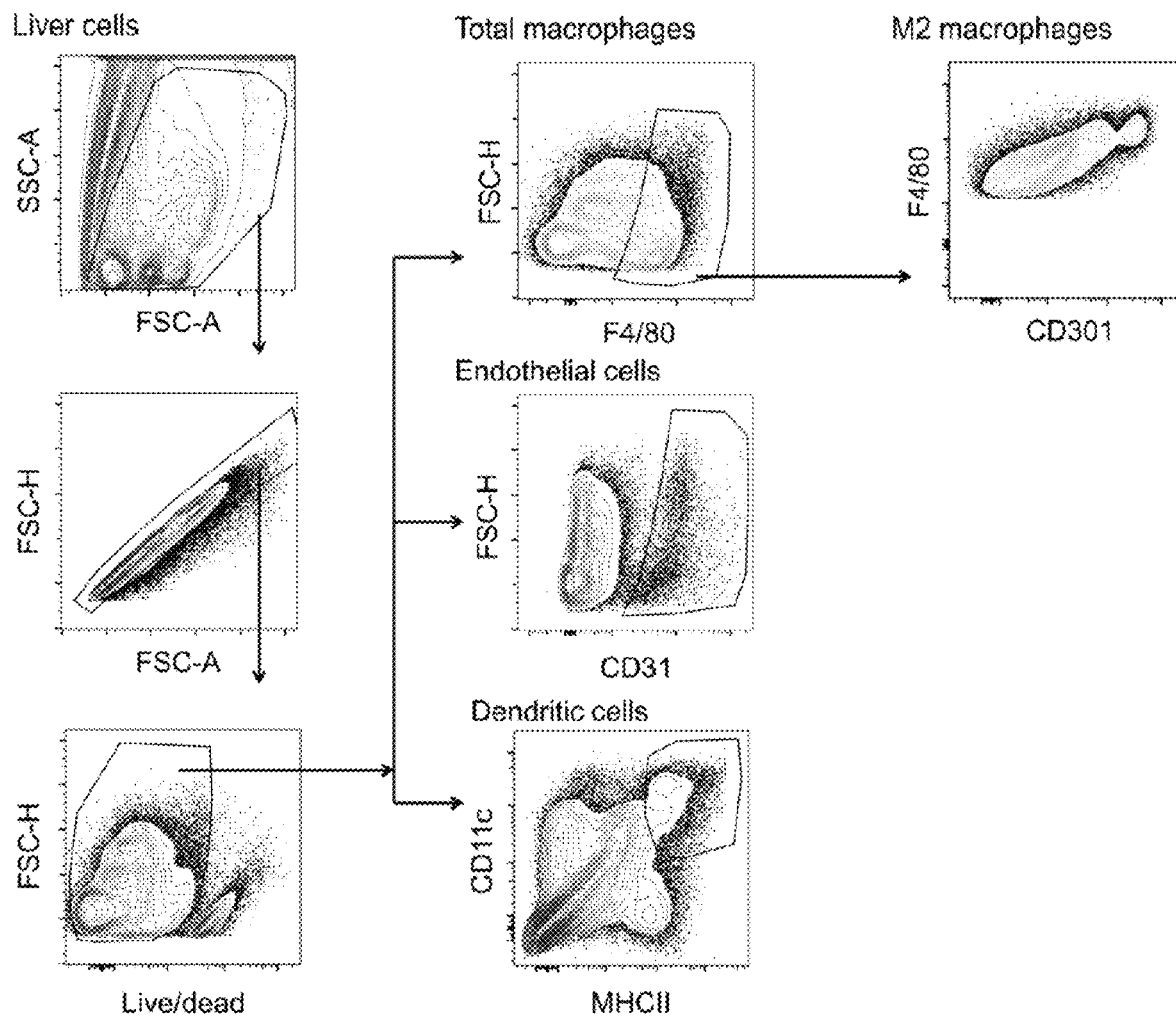
FIG. 25 shows the gating strategy used for flow cytometric analysis of single cell suspensions from the livers of ApoE$^{-/-}$ mice.
Figure 26:
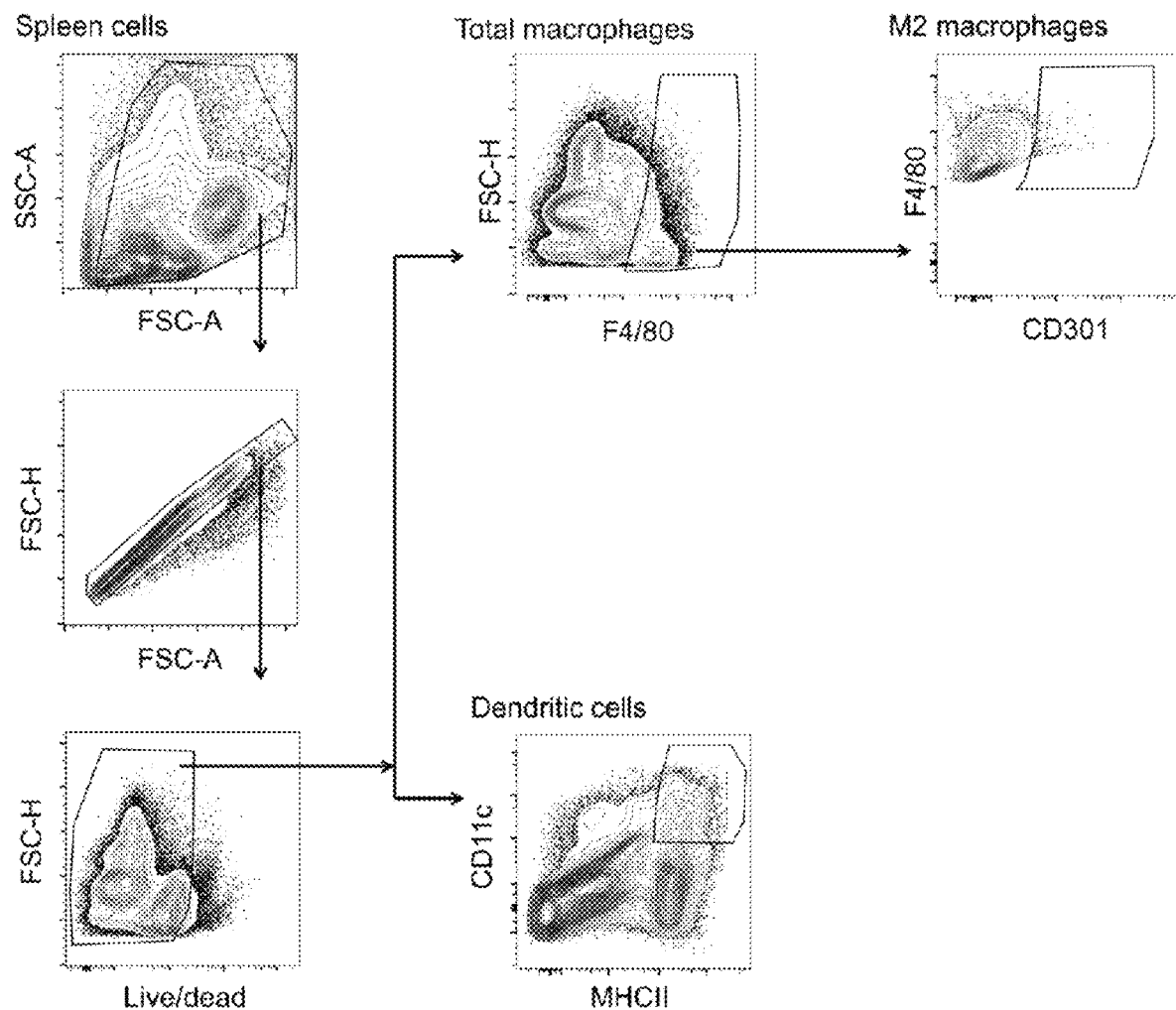
FIG. 26 shows the gating strategy used for flow cytometric analysis of single cell suspensions from the spleens of ApoE$^{-/-}$ mice.
Figure 27:
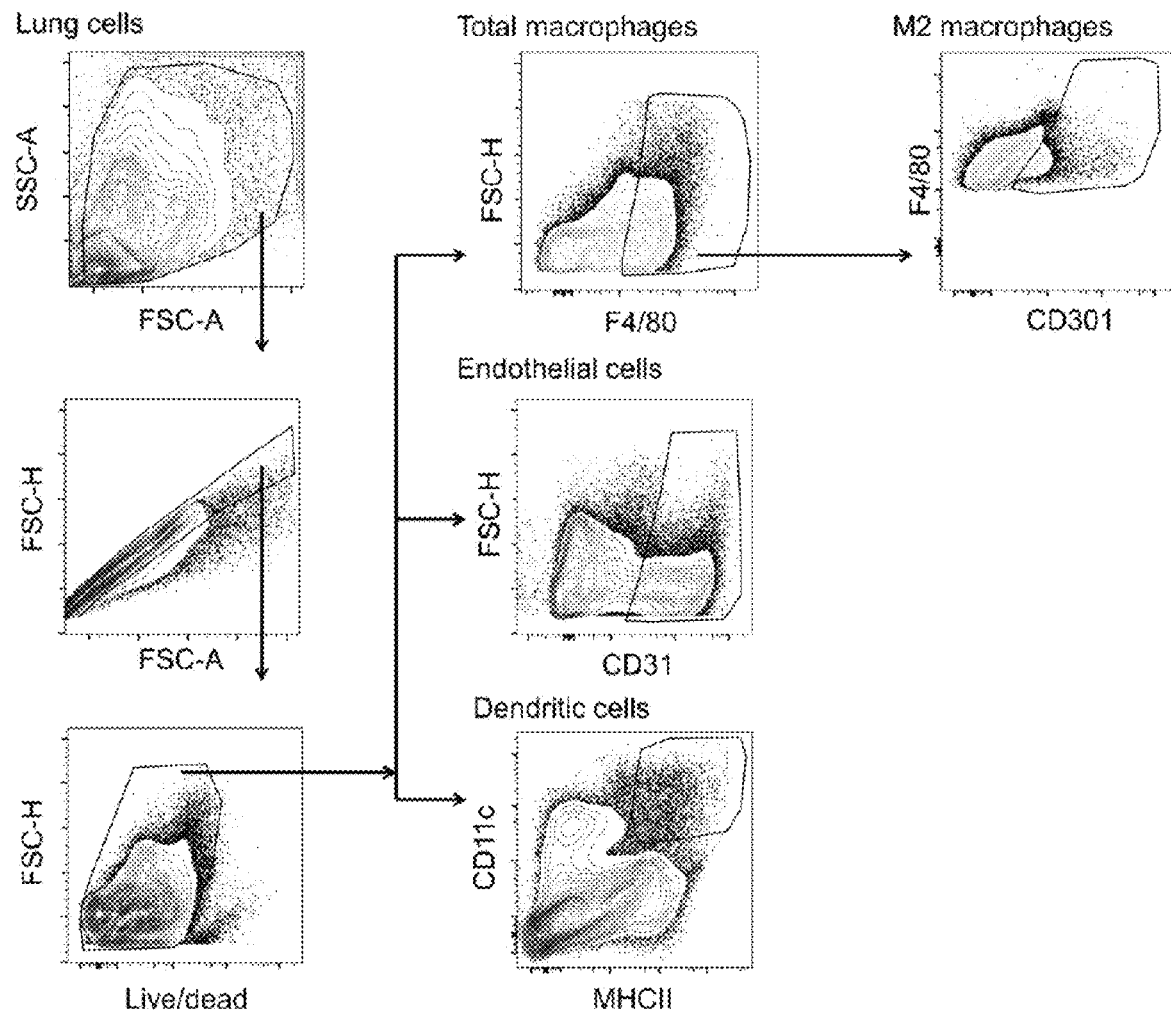
FIG. 27 shows the gating strategy used for flow cytometric analysis of single cell suspensions from the lungs of ApoE$^{-/-}$ mice.

Selected organs were harvested from ApoE$^{-/-}$ mice injected with Cy5.5-PEG-SPIONs or Cy5.5-DNA-SPIONs for NIRF imaging. The liver and spleen were chosen due to their high iron accumulation based on ICP-OES measurements (FIG. 17). The lungs were also selected as negative control due to their low iron content. By enzymatically digesting these organs and labeling the resultant cell suspensions with specific markers of endothelial cells (CD31+), total macrophages (F4/80+), M2 macrophages (F4/80+ and CD301+), and dendritic cells (MCHII+ and CD11c+), the delivery of both SPION types to these cell types in the liver (gating strategy in (FIG. 25), spleen (gating strategy in FIG. 26), and lungs (gating strategy in FIG. 27) were quantified by flow cytometry. For example, a single cell suspension from the liver and lung was gated on FSC-A and SSC-A to exclude cell debris. Singlets are gated on Live/Dead Aqua on AmCyan to the live cell population. From this point on, cells were separated in different staining panels for macrophages (including Kupffer cells) on F4/80, endothelial cells on CD31, and dendritic cells positive on CD11c and MHCII. F4/80+ macrophages were further gated on CD301 for M2 (CD301+) macrophages (FIGS. 25 and 27). For splenic cells, a single cell suspension from the spleen was gated on FSC-A and SSC-A to exclude cell debris. Singlets are gated on Live/Dead Aqua on AmCyan to the live cell population. From this point, cells were separated in different staining panels for macrophages on F4/80, and dendritic cells positive on CD11c and MHCII. F4/80+ macrophages were further gated on CD301 for M2 (CD301+) macrophages (FIG. 26).

Data were expressed in terms of the mean fraction of Cy5.5-positive cells (FIGS. 22 and 24) and mean Cy5.5 fluorescence intensity (MFI) of the cells (FIGS. 23 and 24). By and large, cellular-level distribution varied in different organs; the same cell type located in different organs (e.g., liver endothelial cells versus lung endothelial cells) exhibited vastly different levels of uptake.

Thirty minutes after intravenous injection of both nanoparticle types, the subcellular level distribution in the aorta could be reflected by the percentage of Cy5.5-positive cells in each cell type (FIGS. 20B, C, D, and E): dendritic cells: 0.745% and 8.972% for PEG-SPIONs and DNA-SPIONs; endothelial cells: 0.323% and 1.012% for PEG-SPIONs and DNA-SPIONs; total macrophages: 0.42% and 7.746% for PEG-SPIONs and DNA-SPIONS; and M2 macrophages; 0.554% and 21.52% for PEG-SPIONs and DNA-SPIONs, respectively.

Figure 22A:
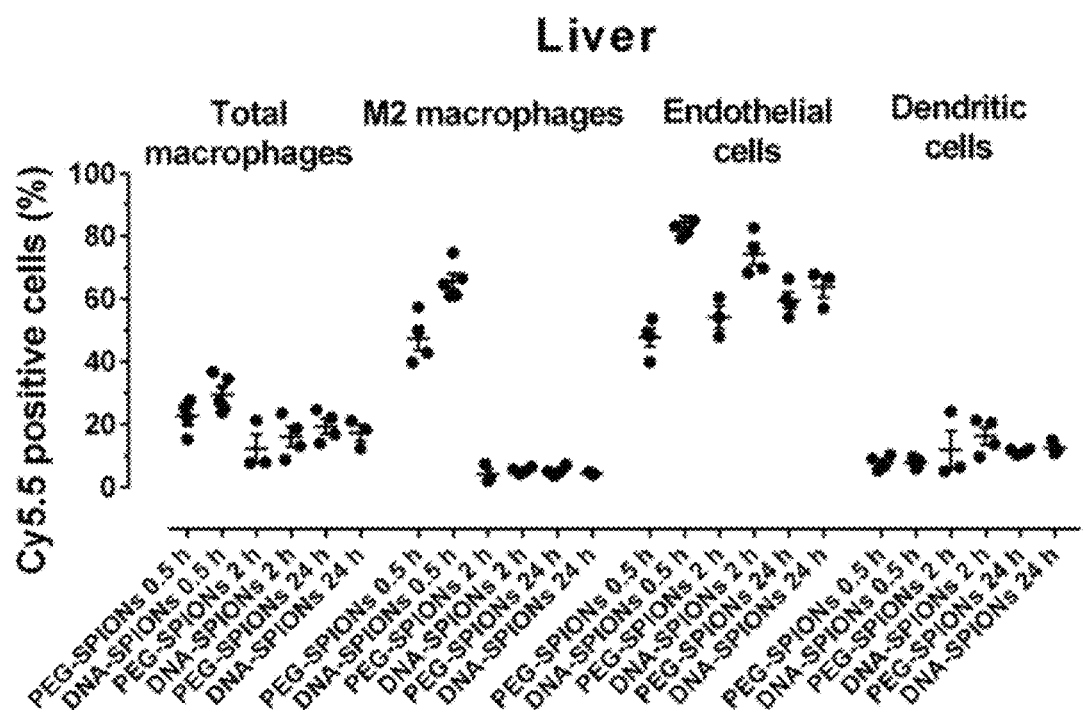
FIGS. 22A through 22F show the cellular-level distribution of PEG-SPIONs and DNA-SPIONs in ApoE$^{-/-}$ mice with atherosclerotic plaques. 0.5 h, 2 h and 24 h post-injection of Cy5.5-PEG-SPIONs or Cy5.5-DNA-SPIONs.
Figure 22B:
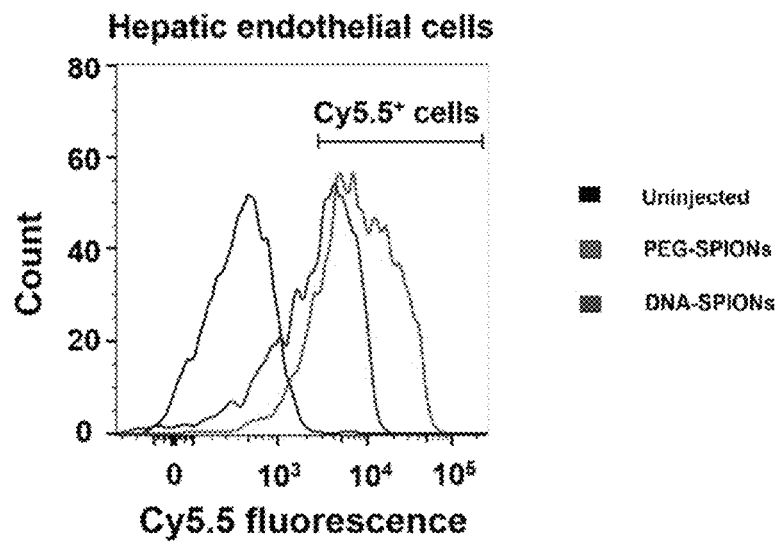
Figure 23A:
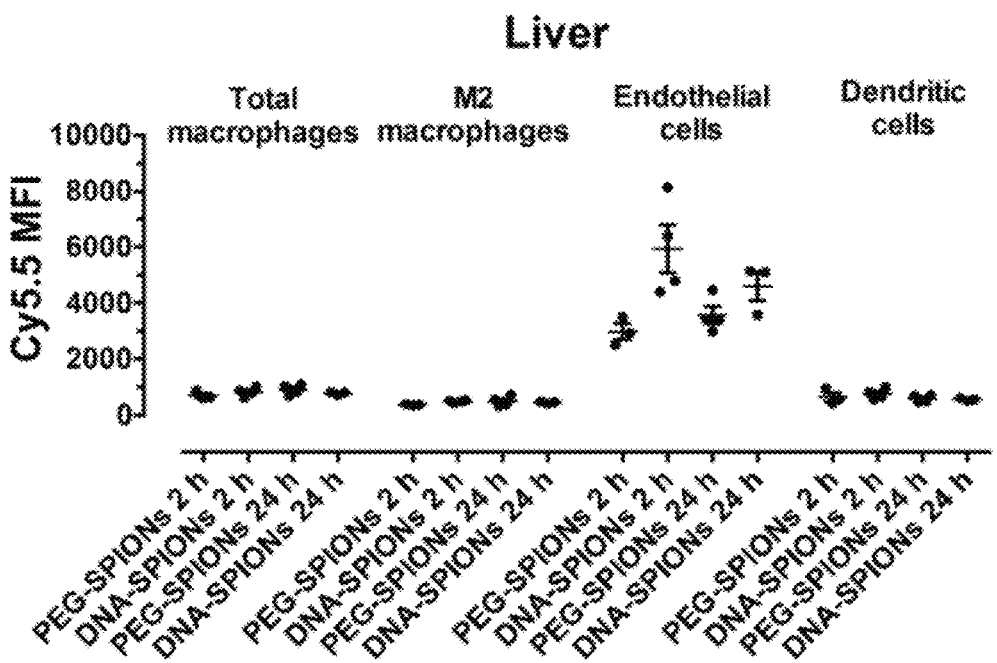
FIG. 23A shows the cellular-level distribution of PEG-SPIONs and DNA-SPIONs in cells isolated from livers of PEG- and DNA-SPION treated ApoE$^{-/-}$ mice.

For the DNA-SPION injection group, within the liver, endothelial cells had the largest mean fraction of Cy5.5-positive cells (~74.3%) 0.5 hours post-injection (FIG. 22A). At 0.5 hours post injection, liver total macrophages and liver M2 macrophages showed ~30% and ~60% Cy5.5-positive cells following Cy5.5-DNA-SPION injection followed by liver dendritic cells with ~16.4% (FIG. 22A).

For the PEG-SPION injection group, a similar trend was observed for the relative population of Cy5.5-positive cells, yet the mean fractions of the Cy5.5-positive cells for all cell types were 20-30% lower than those for the DNA-SPION injection group, i.e., endothelial cells (~54.2%), macrophages (~12.4%), and dendritic cells (~11.9%) at 2 hours post-injection (FIG. 22A). These data highlighted the selectivity of DNA-SPIONs over PEG-SPIONs in entering hepatic cell types, most notably endothelial cells (FIGS. 22A and 22B), although a large portion of the PEG-SPIONs still accumulated inside these cell types.

Figure 23B:
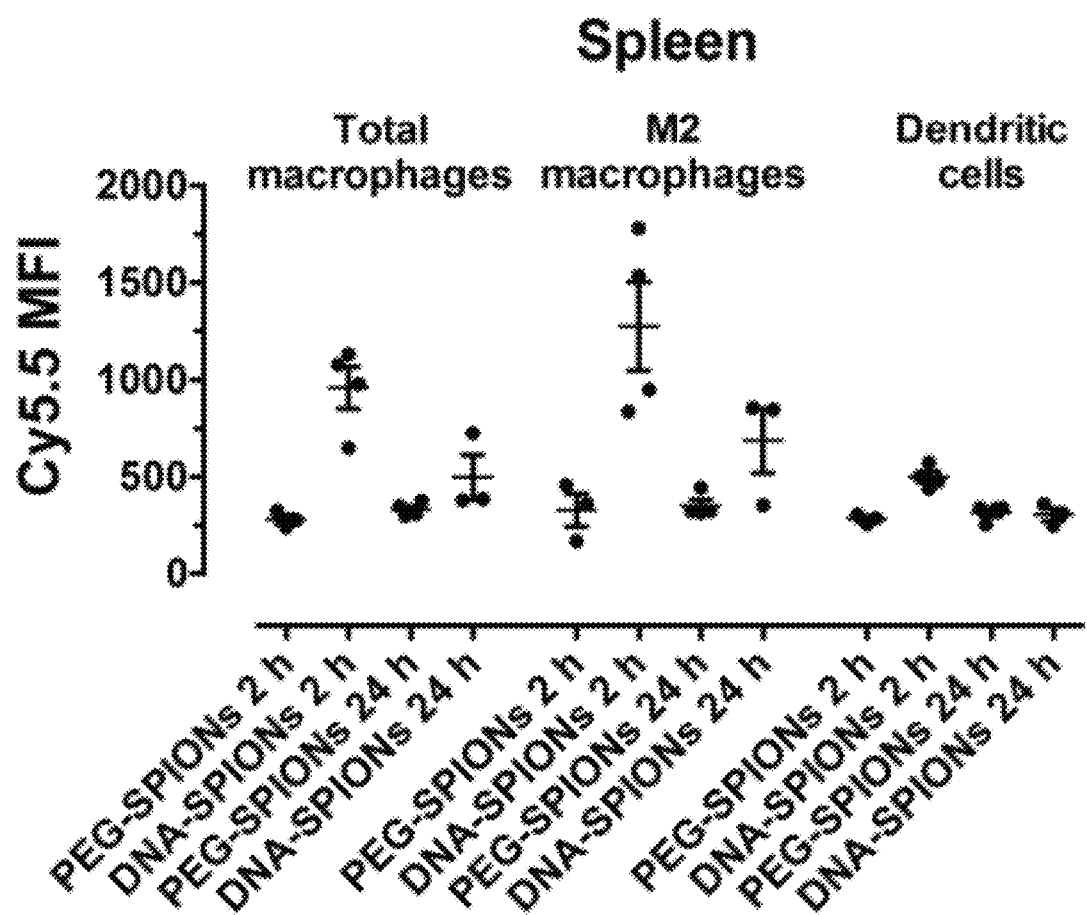
FIG. 23B shows the cellular-level distribution of PEG-SPIONs and DNA-SPIONs in cells isolated from spleens of PEG- and DNA-SPION treated ApoE$^{-/-}$ mice.

In terms of mean fluorescence intensity (MFI), hepatic endothelial cells exhibited the most intense fluorescence per cell, outcompeting total macrophages, dendritic cells, and M2 macrophages by 7-12 times (FIGS. 22A, 22B, 23A and 24B). For the PEG-SPION injection group, the MFI of endothelial cells was also 4-8 times higher than those of total macrophages, dendritic cells, and M2 macrophages, reaffirming the pivotal role of hepatic endothelial cells in internalizing both SPION types (FIGS. 22A and 23B). At 24 hours post-injection, no severe declines in the fractions of Cy5.5-positive cells and MFI were observed, consistent with the organ-level distribution data obtained by ICP-OES analysis (FIG. 17).

Hepatic sinusoidal endothelial cells share the expression of many receptors with hepatic macrophages (or Kupffer cells) (86-87). While hepatic endothelial cells do not undergo phagocytosis under normal circumstances, they actively clear soluble or colloidal materials up to 230 nm in size (88). By contrast, Kupffer cells typically uptake larger particles of larger dimensions (89-90). For example, Tsoi et al. reported a high probability of 64.6% for hepatic endothelial cells to internalize PEG-coated quantum dots i.v. injected to Wistar rats (91), matching the predominant localization of both PEG- and DNASPION types in the instant studies in hepatic endothelial cells. The pronounced uptake of PEG-coated quantum dots by Kupffer cells (84.8%) was reported (91), which is markedly higher than the uptake of PEG- and DNA-SPIONs in the instant studies in hepatic macrophages (FIG. 22). The discrepancy in uptake of nanoparticles by hepatic macrophages can be attributed to several phenomena. ApoE$^{-/-}$ mice fed an atherogenic diet have hepatic pathophysiological features distinct from those of normal mice (e.g., higher cholesterol content (92) and inflammation (93)). Their hepatic immune cells (e.g., macrophages) may exhibit different uptake properties from normal cells. Further, the different choice of markers for hepatic macrophages may lead to identification of different cell populations and different levels of nanoparticle uptake. While for the instant studies F4/80 was chosen as the marker for total macrophages, Tsoi et al. used CD68 to recognize Kupffer cells (91). Species difference (ApoE$^{-/-}$ mice versus Wistar rats) could also contribute to the different intrahepatic cellular-level distribution data.

Figure 22C:
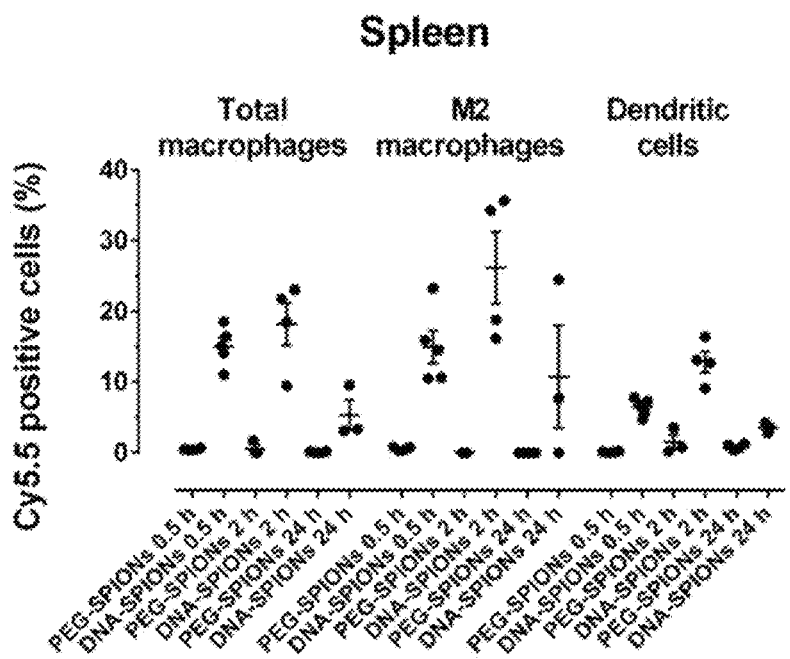

In the spleen of ApoE$^{-/-}$ mice injected with DNA-SPIONs, the cells that internalized the most DNA-SPIONs 2 hours post-injection were M2 macrophages (~26.2%) followed by total macrophages (~18.2%) and dendritic cells (~12.8%), respectively (FIG. 22C). Endothelial cells were not analyzed in this experiment due to their low abundance in the spleen. Further, splenic macrophages had higher MFI than splenic dendritic cells (FIGS. 22D, 22E, 23B and 24B).

Figure 24A:
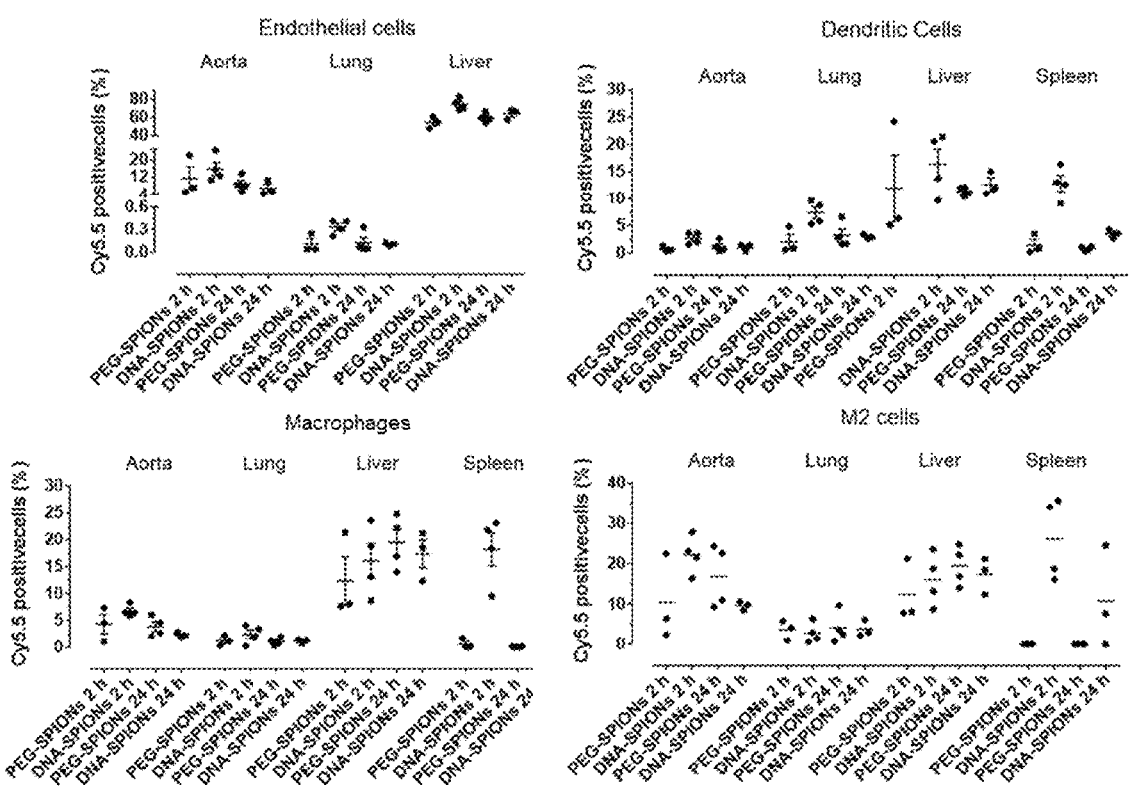
FIG. 24A shows the flow cytometric analysis of the distribution of PEG-SPIONs and DNA-SPIONs in difference cell types from aorta, lung, liver, and spleen 2h and 24h post intravenous injection displayed as percentage of Cy5.5-positive cells.

By contrast, in vivo uptake of PEG-SPIONs by splenic macrophages and dendritic cells was negligible, as evidenced by merely less than 2% of cells identified as Cy5.5-positive for both cell types (FIGS. 22C and 24A).

Figure 22D:
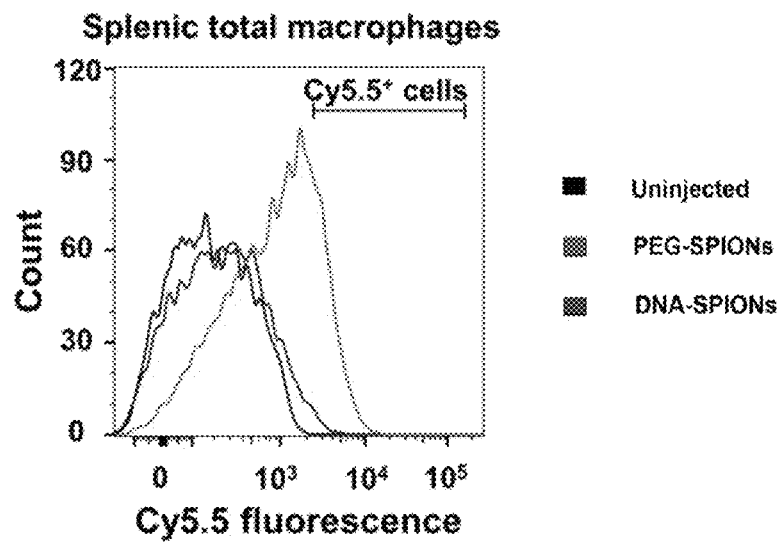
Figure 22E:
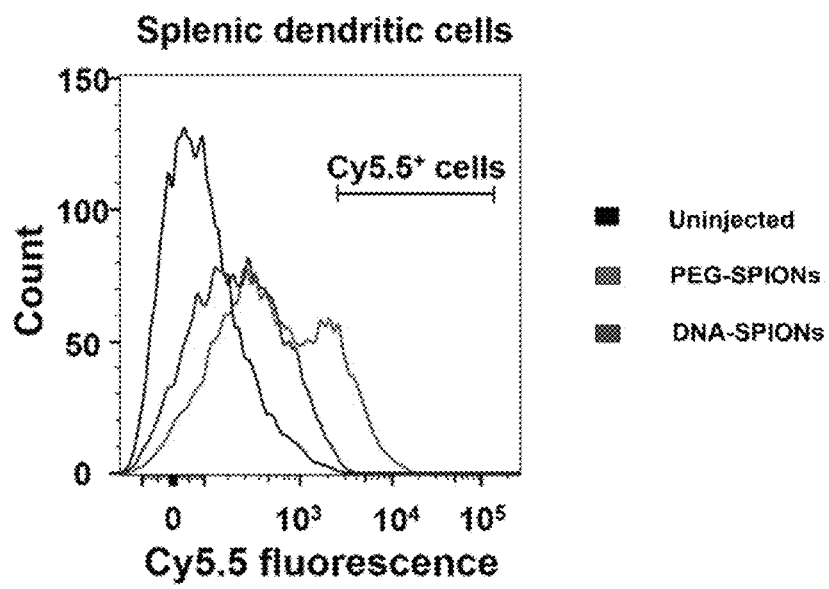
Figure 24B:
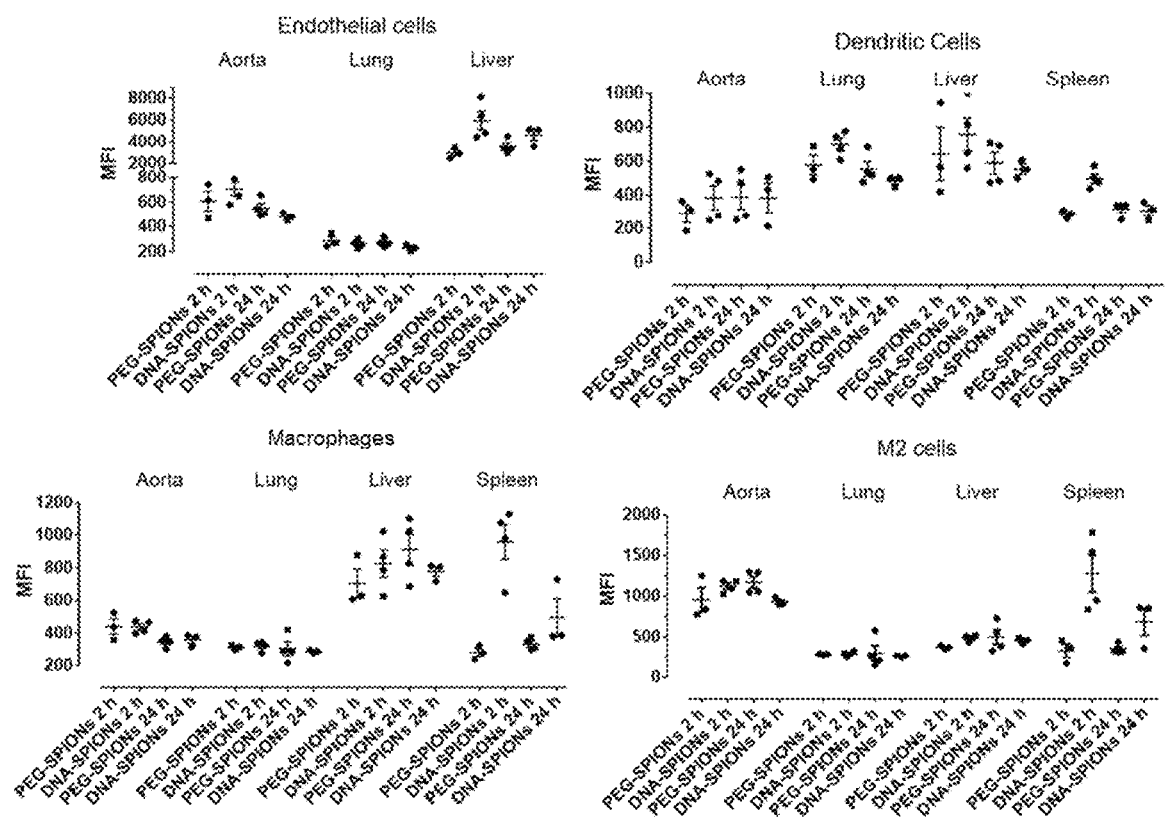
FIG. 24B shows the samples with the results displayed as mean fluorescence intensity.

Upon internalization of Cy5.5-DNA-SPIONs, splenic macrophages have higher mean fractions of Cy5.5-positive cells (FIG. 22D) and MFI than splenic dendritic cells (FIGS. 23B and 24B). The MFIs of splenic macrophages of the Cy5.5-DNA-SPION injection group were 2-4 fold higher than those detected for the Cy5.5-PEG-SPION injection group 2 h post-injection (FIGS. 22D, 22E, and 23B). To a lesser degree than splenic macrophages, splenic dendritic cells internalized Cy5.5-DNA-SPIONs more than Cy5.5-PEG-SPIONs, both in terms of likelihood (FIGS. 22C and 23A) and amount of uptake (FIG. 22E, 23B, and 24B). Twenty-four hours post-injection, splenic macrophages remained the cell type with the highest MFI and highest mean fraction of Cy5.5-positive cells, but both values were almost reduced by 50% compared to the values detected 0.5 hours and 2 hours post-injection (FIGS. 22C, 22D, 23B, 24A and 24B). Concurrently, splenic dendritic cells also experienced drastic reduction in both values compared to those detected 0.5 hours and 2 hours post-injection (FIGS. 22C, 22E, 23B, 24A and 24B).

At the same time point, splenic cells did not appreciably internalize PEG-SPIONs, with no more than 1% of the splenic macrophages and dendritic cells identified as Cy5.5-positive (FIG. 22C). For monocytes in blood and the spleen, no appreciable fluorescence could be detected compared to other cell types (data not shown).

Figure 22F:
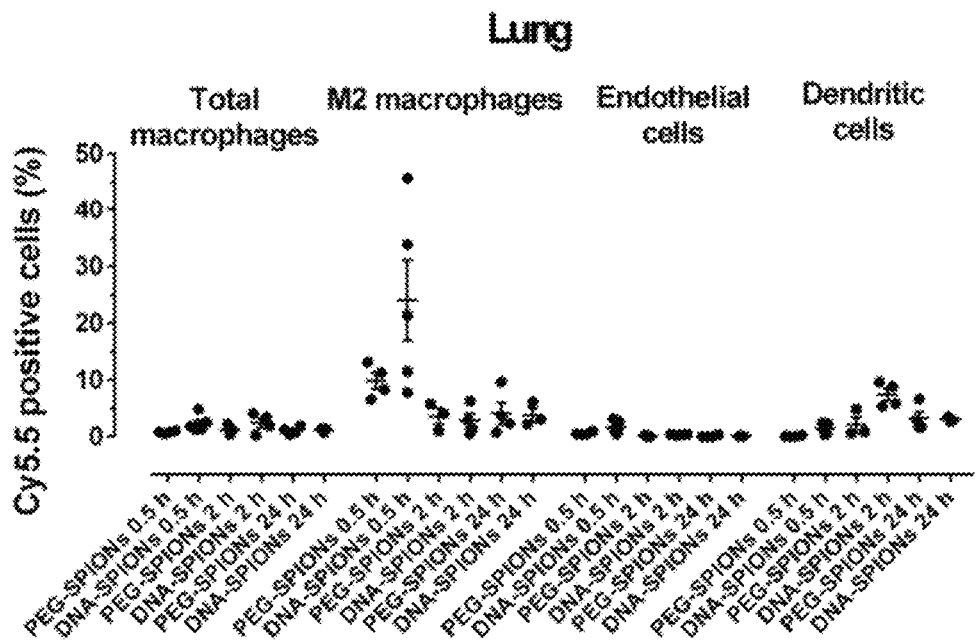
Figure 23C:
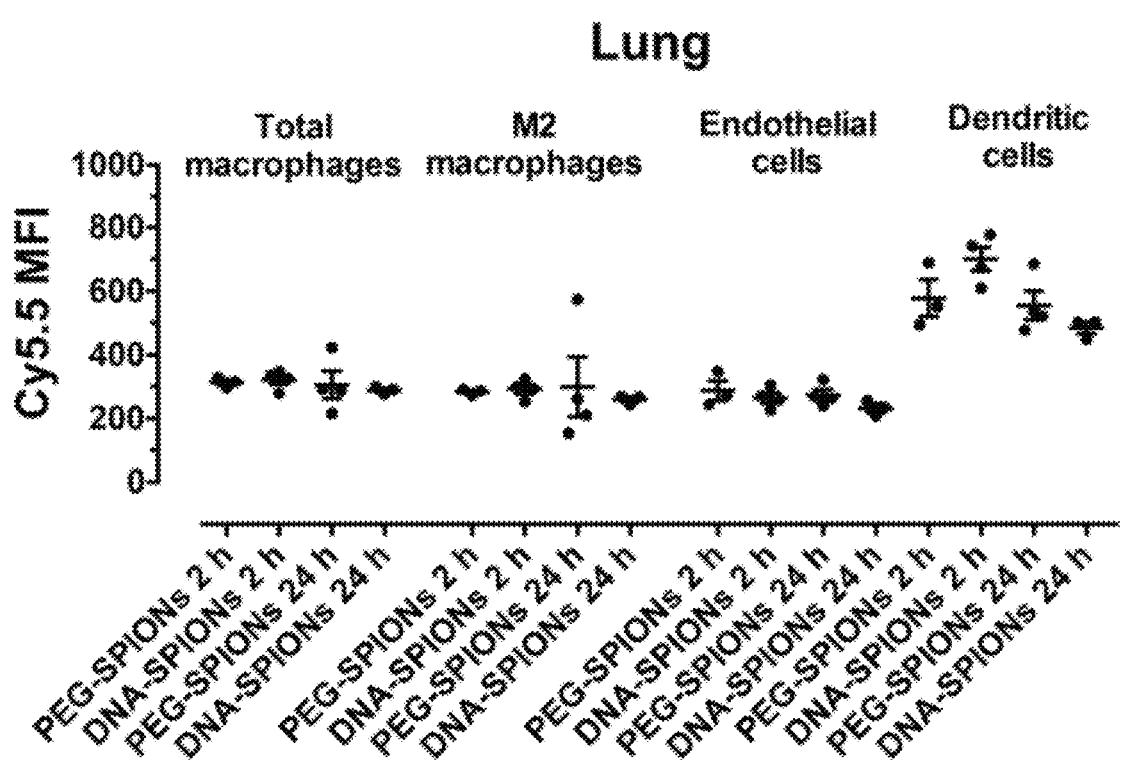
FIG. 23C shows the cellular-level distribution of PEG-SPIONs and DNA-SPIONs in cells isolated from lungs of PEG- and DNA-SPION treated ApoE$^{-/-}$ mice.

In summary, DNA-SPIONs entered splenic macrophages the most among all cell types tested 0.5 hours post-injection, with at least 10-fold selectivity over PEG-SPIONs. These cellular-level distribution data were in agreement with the organ-level distribution data obtained by ICP-OES (FIG. 17) that showed a sharp increase in splenic iron accumulation within the first 2 hours after injection. The plunge in the mean fraction of Cy5.5-positive cells from 2 hours to 24 hours post-injection corroborated the precipitous drop in splenic iron content from 2 hours to 24 hours post-injection as revealed by ICP-OES measurements. For the lungs, the mean fraction of Cy5.5-positive cells and their respective MFI were lower than the liver and spleen (FIGS. 22F, 23C, 24A and 24B). Two hours post-injection of Cy5.5-DNA-SPIONs, up to 7.4% of lung dendritic cells tested Cy5.5-positive, and less than 3% of the other cell types Cy5.5-positive (FIG. 22F). However, 0.5 hours post injection of Cy5.5-DNA-SPIONs, about 25% of M2 macrophages were Cy.5.5-positive (FIG. 22F). Further, the mean fraction of Cy5.5-positive pulmonary endothelial cells and dendritic cells for the Cy5.5-DNA-SPION group was at least 3-fold higher than those for the PEG-SPIONs group (FIG. 22F). In terms of MFI, pulmonary dendritic cells were at least 2-fold higher than other lung cell types for both SPION types (FIGS. 23C and 24B). Thus, DNA-SPIONs most preferentially entered lung macrophages and lung dendritic cells, with 3-fold higher selectivity over PEG-SPIONs. Twenty-four hours post-injection, the mean fraction of Cy5.5-positive cells and MFIs were smaller than those 0.5 hours and 2 hours post-injection, consistent with the NIRF imaging data. Given the negligible uptake of PEG-SPIONs by lung cells, the strong fluorescence observed in the lungs by in vivo NIRF imaging 2 hours post-injection appeared to stem from residual blood inside the lung, noting the longer circulation time of PEG-SPIONs than DNA-SPIONs.

The data showed that macrophages, especially M2 cells, had the highest uptake of SPIONs at 0.5 hours, 2 hours and 24 hours after intravenous injection (FIG. 22). In terms of uptake kinetics, DNA-SPIONs could enter each cell type more potently and more rapidly, indicated by the highest MFI of DNA-SPIONs in all cell types at 0.5 hours and 2 hours post injection.

Interestingly, the distribution of SPIONs in other organs showed different preference for different cell types. First, there was no significant uptake of SPIONS in the monocytes of blood and spleen (data not shown). The neglectable Cy5.5 signals of the lung cells, with the exception of lung M2 macrophages, suggested low intracellular uptake of SPIONs (FIG. 22), which corroborated previous ICP results indicating that a higher iron content in the lung containing PEG-SPIONs was due to residual blood containing PEG-SPIONs owing to the longer circulation time of PEG-SPIONs.

On the contrary, SPIONs largely accumulated in the MPS organs including liver and spleen, which corresponded well with the ICP data. Surprisingly, both PEG- and DNA-SPIONs exhibited overriding distribution in liver endothelial cells (>60% positive). The liver sinusoidal endothelial cells (LSEC) are known to share the expression of a large number of receptors with macrophages, and to have an internalization ability of taking up molecules up to 1 μm in diameter (94-95). Therefore, it appears that the PEG- and DNA-SPIONs arelargely devoured by MPS endothelial cells. On the other hand, SPIONs inside the spleen mostly resided in macrophages (FIG. 22), with the maximal uptake of DNA-SPIONs at 0.5 hours and 2 hours post injection.

In conclusion, DNA-SPIONs showed quicker and preferential uptake in different cells types of both lymphoid organ and non-lymphoid organs, with enhanced targeting efficiency to atherosclerotic plaques via interactions with M2 cells. The DNA-coated SPIONs demonstrated enhanced delivery to macrophages due to the interactions between DNA-SPIONs and SR-A. The uptake kinetics and endocytosis pathway of the DNA-SPIONs based on RAW 264.7 cells demonstrated an efficient uptake into macrophages through a non-caveolar, lipid-raft and actin-related pathway via SR-A. Therefore, the DNA-SPIONscan be used for enhanced delivery to atherosclerotic plaques in vivo, which showed maximal accumulation of DNA-SPIONs in the atherosclerotic lesions at 0.5 hours and 2 hours post intravenous injection. Shorter circulation life and faster clearance of DNA-SPIONs supported their usefulness for both imaging and therapy of atherosclerosis in nanomedicine applications.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Association AH (2015) Heart disease and stroke statistics—at a glance.
2. Frostegård J (2013) Immunity, atherosclerosis and cardiovascular disease. BMC medicine 11(1):117.
3. Hansson, G. K.; Hermansson, A., The Immune System in Atherosclerosis. Nat. Immunol. 2011, 12, 204-212.
4. Libby, P.; Ridker, P. M.; Hansson, G. K., Progress and Challenges in Translating the Biology of Atherosclerosis. Nature 2011, 473, 317-325.
5. Weissleder, R.; Nahrendorf, M.; Pittet, M. J., Imaging Macrophages with Nanoparticles. Nat. Mater. 2014, 13, 125-138.
6. Go, A. S.; Mozaffarian, D.; Roger, V. L.; Benjamin, E. J.; Berry, J. D.; Blaha, M. J.; Dai, S.; Ford, E. S.; Fox, C. S.; Franco, S. et al., Heart Disease and Stroke Statistics—2014 Update: A Report From the American Heart Association. Circulation 2013, 129, e28-e292.
7. Mulder, W. J. M.; Jailer, F. A.; Fayad, Z. A.; Nahrendorf, M., Imaging and Nanomedicine in Inflammatory Atherosclerosis. Sci. Transl. Med. 2014, 6, 239sr1.
8. Tarkin J M, et al. (2016) Imaging Atherosclerosis. Circulation Research 118(4):750-769.
9. Corti R, Fuster V, Badimon J J, Hutter R, & Fayad Z A (2001) New Understanding of Atherosclerosis (Clinically and Experimentally) with Evolving MRI Technology in Vivo. Annals of the New York Academy of Sciences 947(1):181-198.
10. Lobatto, M. E.; Fuster, V.; Fayad, Z. A.; Mulder, W. J. M., Perspectives and Opportunities for Nanomedicine in the Management of Atherosclerosis. Nat. Rev. Drug Discovery 2011, 10, 835-852.
11. Kuai, R.; Li, D.; Chen, Y. E.; Moon, J. J.; Schwendeman, A., High-Density Lipoproteins: Nature's Multifunctional Nanoparticles. ACS Nano 2016, 10, 3015-3041.
12. Bobryshev, Y. V.; Ivanova, E. A.; Chistiakov, D. A.; Nikiforov, N. G.; Orekhov, A. N., Macrophages and Their Role in Atherosclerosis: Pathophysiology and Transcriptome Analysis. BioMed Res. Int. 2016, 2016, 13.
13. McAteer, M. A.; Akhtar, A. M.; von zur Muhlen, C.; Choudhury, R. P., An Approach to Molecular Imaging of Atherosclerosis, Thrombosis, and Vascular Inflammation Using Microparticles of Iron Oxide. Atherosclerosis 2010, 209, 18-27.
14. McAteer, M. A.; Schneider, J. E.; Ali, Z. A.; Warrick, N.; Bursill, C. A.; von zur Muhlen, C.; Greaves, D. R.; Neubauer, S.; Channon, K. M.; Choudhury, R. P., Magnetic Resonance Imaging of Endothelial Adhesion Molecules in Mouse Atherosclerosis Using Dual-Targeted Microparticles of Iron Oxide. Arterioscler., Thromb., Vasc. Biol. 2008, 28, 77-83.
15. Chung, E. J., Targeting and Therapeutic Peptides in Nanomedicine for Atherosclerosis. Exp. Biol. Med. 2016, 241, 891-898.
16. Wang, Y.; Chen, J.; Yang, B.; Qiao, H.; Gao, L.; Su, T.; Ma, S.; Zhang, X.; Li, X.; Liu, G. et al., In Vivo MR and Fluorescence Dual-modality Imaging of Atherosclerosis Characteristics in Mice Using Profilin-1 Targeted Magnetic Nanoparticles. Theranostics 2016, 6, 272-286.
17. Chen, W.; Cormode, D. P.; Vengrenyuk, Y.; Herranz, B.; Feig, J. E.; Klink, A.; Mulder, W. J. M.; Fisher, E. A.; Fayad, Z. A., Collagen-Specific Peptide Conjugated HDL Nanoparticles as MRI Contrast Agent to Evaluate Compositional Changes in Atherosclerotic Plaque Regression. JACC: Cardovasc. Imag. 2013, 6, 373-384.
18. Kamaly, N.; Fredman, G.; Fojas, J. J. R.; Subramanian, M.; Choi, W., II; Zepeda, K.; Vilos, C.; Yu, M.; Gadde, S.; Wu, J. et al., Targeted Interleukin-10 Nanotherapeutics Developed with a Microfluidic Chip Enhance Resolution of Inflammation in Advanced Atherosclerosis. ACS Nano 2016, 10, 5280-5292.
19. Sinha, A.; Shaporev, A.; Nosoudi, N.; Lei, Y.; Vertegel, A.; Lessner, S.; Vyavahare, N., Nanoparticle Targeting to Diseased Vasculature for Imaging and Therapy. Nanomedicine: Nanotechnol. 2014, 10, e1003-e1012.
20. Hamzah, J.; Kotamraju, V. R.; Seo, J. W.; Agemy, L.; Fogal, V.; Mahakian, L. M.; Peters, D.; Roth, L.; Gagnon, M. K. J.; Ferrara, K. W. et al., Specific Penetration and Accumulation of a Homing Peptide Within Atherosclerotic Plaques of Apolipoprotein E-Deficient Mice. Proc. Natl. Acad. Sci. U.S.A. 2011, 108, 7154-7159.
21. Chen, W.; Vucic, E.; Leupold, E.; Mulder, W. J. M.; Cormode, D. P.; Briley-Saebo, K. C.; Barazza, A.; Fisher, E. A.; Dathe, M.; Fayad, Z. A., Incorporation of an ApoE-Derived Lipopeptide in High-Density Lipoprotein MRI Contrast Agents for Enhanced Imaging of Macrophages in Atherosclerosis. Contrast Media Mol. Imaging 2008, 3, 233-242.
22. Amirbekian, V.; Lipinski, M. J.; Briley-Saebo, K. C.; Amirbekian, S.; Aguinaldo, J. G. S.; Weinreb, D. B.;

Vucic, E.; Frias, J. C.; Hyafil, F.; Mani, V. et al., Detecting and Assessing Macrophages in Vivo to Evaluate Atherosclerosis Noninvasively Using Molecular MRI. Proc. Natl. Acad. Sci. U.S.A. 2007, 104, 961-966.

23. Lipinski, M. J.; Frias, J. C.; Amirbekian, V.; Briley-Saebo, K. C.; Mani, V.; Samber, D.; Abbate, A.; Aguinaldo, J. G. S.; Massey, D.; Fuster, V. et al., Macrophage-Specific Lipid-Based Nanoparticles Improve Cardiac Magnetic Resonance Detection and Characterization of Human Atherosclerosis. JACC: Cardovasc. Imag. 2009, 2, 637-647.

24. Dellinger, A.; Olson, J.; Link, K.; Vance, S.; Sandros, M. G.; Yang, J.; Zhou, Z.; Kepley, C. L., Functionalization of Gadolinium Metallofullerenes for Detecting Atherosclerotic Plaque Lesions by Cardiovascular Magnetic Resonance. J. Cardiovasc. Magn. R. 2013, 15, 1-12.

25. Kamat, M.; El-Boubbou, K.; Zhu, D. C.; Lansdell, T.; Lu, X.; Li, W.; Huang, X., Hyaluronic Acid Immobilized Magnetic Nanoparticles for Active Targeting and Imaging of Macrophages. Bioconjugate Chem. 2010, 21, 2128-2135.

26. Lee, G. Y.; Kim, J.-H.; Choi, K. Y.; Yoon, H. Y.; Kim, K.; Kwon, I. C.; Choi, K.; Lee, B.-H.; Park, J. H.; Kim, I.-S., Hyaluronic Acid Nanoparticles for Active Targeting Atherosclerosis. Biomaterials 2015, 53, 341-348.

27. Beldman, T. J.; Senders, M. L.; Alaarg, A.; Pérez-Medina, C.; Tang, J.; Zhao, Y.; Fay, F.; Deichmöller, J.; Born, B.; Desclos, E. et al., Hyaluronan Nanoparticles Selectively Target Plaque-Associated Macrophages and Improve Plaque Stability in Atherosclerosis. ACS Nano 2017, 11, 5785-5799.

28. Taniguchi, R.; Miura, Y.; Koyama, H.; Chida, T.; Anraku, Y.; Kishimura, A.; Shigematsu, K.; Kataoka, K.; Watanabe, T., Adequately-Sized Nanocarriers Allow Sustained Targeted Drug Delivery to Neointimal Lesions in Rat Arteries. Mol. Pharmaceutics 2016, 13, 2108-2116.

29. Petersen, L. K.; York, A. W.; Lewis, D. R.; Ahuja, S.; Uhrich, K. E.; Prud'homme, R. K.; Moghe, P. V., Amphiphilic Nanoparticles Repress Macrophage Atherogenesis: Novel Core/Shell Designs for Scavenger Receptor Targeting and Down-Regulation. Mol. Pharmaceutics 2014, 11, 2815-2824.

30. Lewis, D. R.; Petersen, L. K.; York, A. W.; Zablocki, K. R.; Joseph, L. B.; Kholodovych, V.; Prud'homme, R. K.; Uhrich, K. E.; Moghe, P. V., Sugar-Based Amphiphilic Nanoparticles Arrest Atherosclerosis in Vivo. Proc. Natl. Acad. Sci. U.S.A. 2015, 112, 2693-2698.

31. Li, J.-M.; Newburger, P. E.; Gounis, M.; Dargon, P.; Zhang, X.; Messina, L. M., Local Arterial Nanoparticle Delivery of siRNA for NDOX2 Knockdown to Prevent Restenosis in an Atherosclerotic Rat Model. Gene Ther. 2010, 17, 1279-1287.

32. Kheirolomoom, A.; Kim, C. W.; Seo, J. W.; Kumar, S.; Son, D. J.; Gagnon, M. K. J.; Ingham, E. S.; Ferrara, K. W.; Jo, H., Multifunctional Nanoparticles Facilitate Molecular Targeting and MiRNA Delivery to Inhibit Atherosclerosis in ApoE−/− Mice. ACS Nano 2015, 9, 8885-8897.

33. Katsuki, S.; Matoba, T.; Nakashiro, S.; Sato, K.; Koga, J.-i.; Nakano, K.; Nakano, Y.; Egusa, S.; Sunagawa, K.; Egashira, K., Nanoparticle-Mediated Delivery of Pitavastatin Inhibits Atherosclerotic Plaque Destabilization/Rupture in Mice by Regulating the Recruitment of Inflammatory Monocytes. Circulation 2014, 129, 896.

34. Boyer C, Whittaker M R, Bulmus V, Liu J, & Davis T P (2010) The design and utility of polymer-stabilized iron-oxide nanoparticles for nanomedicine applications. NPG Asia Mater 2:23-30.

35. Lin C, Cai S, & Feng J (2012) Positive Contrast Imaging of SPIO Nanoparticles. Journal of Nanomaterials 2012:9.

36. Kooi M E, et al. (2003) Accumulation of Ultrasmall Superparamagnetic Particles of Iron Oxide in Human Atherosclerotic Plaques Can Be Detected by In Vivo Magnetic Resonance Imaging. Circulation 107(19):2453-2458.

37. Corot C, et al. (2004) Macrophage Imaging in Central Nervous System and in Carotid Atherosclerotic Plaque Using Ultrasmall Superparamagnetic Iron Oxide in Magnetic Resonance Imaging. Investigative Radiology 39(10):619-625.

38. Gough P J, et al. (1999) Analysis of macrophage scavenger receptor (SR-A) expression in human aortic atherosclerotic lesions. Arteriosclerosis, thrombosis, and vascular biology 19(3):461-471.

39. de Winther M P J, van Dijk K W, Havekes L M, & Hofker M H (2000) Macrophage Scavenger Receptor Class A: A Multifunctional Receptor in Atherosclerosis. Arteriosclerosis, thrombosis, and vascular biology 20(2): 290-297.

40. Rekhter M D & Gordon D (1995) Active proliferation of different cell types, including lymphocytes, in human atherosclerotic plaques. The American Journal of Pathology 147(3):668-677.

41. Thapa N, et al. (2008) Identification of a peptide ligand recognizing dysfunctional endothelial cells for targeting atherosclerosis. Journal of Controlled Release 131(1):27-33.

42. Segers F M E, et al. (2013) Scavenger Receptor-AI-Targeted Iron Oxide Nanoparticles for In Vivo MRI Detection of Atherosclerotic Lesions. Arteriosclerosis, thrombosis, and vascular biology 33(8):1812-1819.

43. Jia Q, et al. (2011) Gelification: An Effective Measure for Achieving Differently Sized Biocompatible Fe3O4 Nanocrystals through a Single Preparation Recipe. Journal of the American Chemical Society 133(48):19512-19523.

44. Li Z, Wei L, Gao M Y, & Lei H (2005) One-Pot Reaction to Synthesize Biocompatible Magnetite Nanoparticles. Advanced Materials 17(8):1001-1005.

45. Butcher M J, Herre M, Ley K, & Galkina E (2011) Flow Cytometry Analysis of Immune Cells Within Murine Aortas. Journal of Visualized Experiments : JoVE (53): 2848.

46. Dunlop D J (1973) Superparamagnetic and single-domain threshold sizes in magnetite. Journal of Geophysical Research 78(11):1780-1793.

47. Kolosnjaj-Tabi J, et al. (2015) The One Year Fate of Iron Oxide Coated Gold Nanoparticles in Mice. ACS Nano 9(8):7925-7939.

48. Qiao R, Yang C, & Gao M (2009) Superparamagnetic iron oxide nanoparticles: from preparations to in vivo MilI applications. Journal of Materials Chemistry 19(35): 6274-6293.

49. Giljohann D A, et al. (2007) Oligonucleotide Loading Determines Cellular Uptake of DNA-Modified Gold Nanoparticl es. Nano Letters 7(12):3818-3821.

50. Hurst S J, Lytton-Jean A K R, & Mirkin C A (2006) Maximizing DNA Loading on a Range of Gold Nanoparticle Sizes. Analytical chemistry 78(24):8313-8318.

51. Cutler J I, Zheng D, Xu X, Giljohann D A, & Mirkin C A (2010) Polyvalent Oligonucleotide Iron Oxide Nanoparticle "Click" Conjugates. *Nano Letters* 10(4):1477-1480.
52. Tabas I, García-Cardeña G, & Owens G K (2015) Recent insights into the cellular biology of atherosclerosis. *The Journal of Cell Biology* 209(1):13-22.
53. Tarbell J M (2010) Shear stress and the endothelial transport barrier. Cardiovascular Research 87(2):320-330.
54. Rajendran P, et al. (2013) The Vascular Endothelium and Human Diseases. International Journal of Biological Sciences 9(10):1057-1069.
55. Gu L, Fang R H, Sailor M J, & Park J-H (2012) In Vivo Clearance and Toxicity of Monodisperse Iron Oxide Nanocrystals. ACS Nano 6(6):4947-4954.
56. Bancos S & Tyner K M (2014) Evaluating the effect of assay preparation on the uptake of gold nanoparticles by RAW264.7 cells. Journal of Nanobiotechnology 12(1):1-11.
57. Kim J A, Aberg C, Salvati A, & Dawson K A (2012) Role of cell cycle on the cellular uptake and dilution of nanoparticles in a cell population. Nat Nano 7(1):62-68.
58. Lorenz J N & Gruenstein E (1999) A simple, nonradioactive method for evaluating single-nephron filtration rate using FITC-inulin. American Journal of Physiology—Renal Physiology 276(1):F172.
59. Geisow M J (1984) Fluorescein conjugates as indicators of subcellular pH. Experimental Cell Research 150(1):29-35.
60. Wu X A, Choi C H J, Zhang C, Hao L, & Mirkin C A (2014) Intracellular Fate of Spherical Nucleic Acid Nanoparticle Conjugates. Journal of the American Chemical Society 136(21):7726-7733.
61. Choi C H J, Hao L, Narayan S P, Auyeung E, & Mirkin C A (2013) Mechanism for the endocytosis of spherical nucleic acid nanoparticle conjugates. Proceedings of the National Academy of Sciences 110(19):7625-7630.
62. Verma A, et al. (2009) Analysis of the Fc Gamma Receptor-Dependent Component of Neutralization Measured by Anthrax Toxin Neutralization Assays. Clinical and Vaccine Immunology : CVI 16(10):1405-1412.
63. Dobrovolskaia M A & McNeil S E (2007) Immunological properties of engineered nanomaterials. Nat Nano 2(8):469-478.
64. Khalil I A, Kogure K, Akita H, & Harashima H (2006) Uptake Pathways and Subsequent Intracellular Trafficking in Nonviral Gene Delivery. Pharmacological reviews 58(1):32-45.
65. Luo, Y.; Cook, E.; Fries, B. C.; Casadevall, A., Phagocytic Efficacy of Macrophage-Like Cells as a Function of Cell Cycle and Fcγ Receptors (FcγR) and Complement Receptor (CR)3 Expression. *Clin. Exp. Immunol.* 2006, 145, 380-387.
66. Herter, S.; Birk, M. C.; Klein, C.; Gerdes, C.; Umana, P.; Bacac, M., Glycoengineering of Therapeutic Antibodies Enhances Monocyte/Macrophage-Mediated Phagocytosis and Cytotoxicity. *J. Immunol.* 2014, 192, 2252-2260.
67. Mayor, S.; Pagano, R. E., Pathways of Clathrin-Independent Endocytosis. *Nat. Rev. Mol. Cell Biol.* 2007, 8, 603-612.
68. Oh P, McIntosh D P, & Schnitzer J E (1998) Dynamin at the Neck of Caveolae Mediates Their Budding to Form Transport Vesicles by GTP-driven Fission from the Plasma Membrane of Endothelium. *The Journal of Cell Biology* 141(1):101-114.
69. Parton R G & Simons K (2007) The multiple faces of caveolae. Nat Rev Mol Cell Biol 8(3):185-194.
70. Mellman I (1996) ENDOCYTOSIS AND MOLECULAR SORTING. *Annual Review of Cell and Developmental Biology* 12(1):575-625.
71. Anonymous (1983) Internalization and processing of transferrin and the transferrin receptor in human carcinoma A431 cells. *The Journal of Cell Biology* 97(2):508-521.
72. He K, et al. (2015) Internalization of the TGF-[beta] type I receptor into caveolin-1 and EEA1 double-positive early endosomes. *Cell Res* 25(6):738-752.
73. Ganley I G, Carroll K, Bittova L, & Pfeffer S (2004) Rab9 GTPase Regulates Late Endosome Size and Requires Effector Interaction for Its Stability. *Molecular biology of the cell* 15(12):5420-5430.
74. Nielsen E, Severin F, Backer J M, Hyman A A, & Zerial M (1999) Rab5 regulates motility of early endosomes on microtubules. *Nat Cell Biol* 1(6):376-382.
75. Barbero P, Bittova L, & Pfeffer S R (2002) Visualization of Rab9-mediated vesicle transport from endosomes to the trans-Golgi in living cells. *The Journal of Cell Biology* 156(3):511-518.
76. Carlsson S R & Fukuda M (1989) Structure of human lysosomal membrane glycoprotein 1. Assignment of disulfide bonds and visualization of its domain arrangement. *Journal of Biological Chemistry* 264(34):20526-20531.
77. Doherty, G. J.; McMahon, H. T., Mechanisms of Endocytosis. Annu. Rev. Biochem. 2009, 78, 857-902.
78. Xiao, K.; Li, Y.; Luo, J.; Lee, J. S.; Xiao, W.; Gonik, A. M.; Agarwal, R.; Lam, K. S., The Effect of Surface Charge on in Vivo Biodistribution of PEG-Oligocholic Acid Based Micellar Nanoparticles. Biomaterials 2011, 32, 3435-3446.
79. Chinen A B, Ferrer J R, Merkel T J, & Mirkin C A (2016) Relationships between Poly(ethylene glycol) Modifications on RNA-Spherical Nucleic Acid Conjugates and Cellular Uptake and Circulation Time. *Bioconjugate chemistry* 27(11):2715-2721.
80. Arami H, Khandhar A, Liggitt D, & Krishnan K M (2015) In vivo delivery, pharmacokinetics, biodistribution and toxicity of iron oxide nanoparticles. *Chemical Society reviews* 44(23):8576-8607.
81. Soo Choi, H.; Liu, W.; Misra, P.; Tanaka, E.; Zimmer, J. P.; Itty Ipe, B.; Bawendi, M. G.; Frangioni, J. V., Renal Clearance of Quantum Dots. Nat. Biotechnol. 2007, 25, 1165-1170.
82. Zuckerman, J. E.; Choi, C. H. J.; Han, H.; Davis, M. E., Polycation-siRNA Nanoparticles Can Disassemble at the Kidney Glomerular Aasement Membrane. Proc. Natl. Acad. Sci. U.S.A. 2012, 109, 3137-3142.
83. Choi, C. H. J.; Zuckerman, J. E.; Webster, P.; Davis, M. E., Targeting Kidney Mesangium by Nanoparticles of Defined Size. Proc. Natl. Acad. Sci. U.S.A. 2011, 108, 6656-6661.
84. Kimura, R. H.; Cheng, Z.; Gambhir, S. S.; Cochran, J. R., Engineered Knottin Peptides: A New Class of Agents for Imaging Integrin Expression in Living Subjects. Cancer Res. 2009, 69, 2435.
85. Kimura, R. H.; Miao, Z.; Cheng, Z.; Gambhir, S. S.; Cochran, J. R., A Dual-Labeled Knottin Peptide for PET and Near-Infrared Fluorescence Imaging of Integrin Expression in Living Subjects. Bioconjugate Chem. 2010, 21, 436-444.
86. Knolle, P. A.; Limmer, A., Control of Immune Responses by Scavenger Liver Endothelial Cells. Swiss Med. Wkly. 2003, 133, 501-506.

87. Steffan, A.-M.; Gendrault, J.-L.; McCuskey, R. S.; McCuskey, P. A.; Kirn, A., Phagocytosis, an Unrecognized Property of Murine Endothelial Liver Cells. Hepatology 1986, 6, 830-836.
88. Shiratori, Y.; Tananka, M.; Kawase, T.; Shiina, S.; Komatsu, Y.; Omata, M., Quantification of Sinusoidal Cell Function In Vivo. Semin. Liver Dis. 1993, 13, 39-49.
89. Elvevold, K.; Smedsrd, B.; Martinez, I., The Liver Sinusoidal Endothelial Cell: a Cell Type of Controversial and Confusing Identity. Am. J. Physiol.: Gastrointest. Liver Physiol. 2008, 294, G391-G400.
90. Smedsrd, B., Clearance Function of Scavenger Endothelial Cells. Comp. Hepatol. 2004, 3, S22.
91. Tsoi, K. M.; MacParland, S. A.; Ma, X.-Z.; Spetzler, V. N.; Echeverri, J.; Ouyang, B.; Fadel, S. M.; Sykes, E. A.; Goldaracena, N.; Kaths, J. M. et al., Mechanism of Hard-Nanomaterial Clearance by the Liver. Nat. Mater. 2016, 15, 1212-1221.
92. Moghadasian, M. H.; McManus, B. M.; Nguyen, L. B.; Shefer, S.; Nadji, M.; Godin, D. V.; Green, T. J.; Hill, J.; Yang, Y.; Scudamore, C. H.; Frohlich, J. J., Pathophysiology of Apolipoprotein E Deficiency in Mice: Relevance to Apo E-Related Disorders in Humans. FASEB J. 2001, 15, 2623-2630.
93. Schierwagen, R.; Maybüchen, L.; Zimmer, S.; Hittatiya, K.; Bäck, C.; Klein, S.; Uschner, F. E.; Reul, W.; Boor, P.; Nickenig, G. et al., Seven Weeks of Western Diet in Apolipoprotein-E-Deficient Mice Induce Metabolic Syndrome and Non-Alcoholic Steatohepatitis with Liver Fibrosis. Sci. Rep. 2015, 5, 12931.
94. Knolle P A & Limmer A (2003) Control of immune responses by scavenger liver endothelial cells. Swiss medical weekly 133(37/38):501-506.
95. Steffan A-M, Gendrault J-L, McCuskey R S, McCuskey P A, & Kirn A (1986) Phagocytosis, an unrecognized property of murine endothelial liver cells. Hepatology 6(5):830-836.
96. Cole A J, David A E, Wang J, Galbán C J, & Yang V C (2011) Magnetic brain tumor targeting and biodistribution of long-circulating PEG-modified, cross-linked starch coated iron oxide nanoparticles. Biomaterials 32(26): 6291-6301.
97. Chinen, A. B.; Guan, C. M.; Mirkin, C. A., Spherical Nucleic Acid Nanoparticle Conjugates Enhance G-Quadruplex Formation and Increase Serum Protein Interactions. Angew. Chem. Int. Ed. 2015, 54, 527-531.

We claim:

1. A process of using a nanoparticle (NP)-cored spherical nucleic acid (DNA-NP) comprising the steps of:
    obtaining a DNA-NP comprising poly(ethylene glycol) (PEG)-linked oligonucleotides wherein the obtaining step comprises:
    synthesizing an iron core-poly(ethylenglycol)(PEG)-oleylamine NP using PEG diacid and attaching at least one amino-modified DNA oligonucleotide to the iron core-PEG-oleylamine NP, wherein the iron core-PEG-oleylamine NP is devoid of other polymerized structures in the layers between the iron core and the DNA oligonucleotides; and
    manufacturing a product comprising said DNA-NP comprising PEG-linked oligonucleotides, wherein the process further comprises loading the DNA-NP comprising PEG-linked oligonucleotides with at least one therapeutic agent.

2. The process of claim 1, wherein the nanoparticle-cored spherical nucleic acid is a superparamagnetic nanoparticle (SPN)-cored spherical nucleic acid (DNA-SPN).

3. The process of claim 2, wherein the SPN-cored spherical nucleic acid is a superparamagnetic iron oxide nanoparticle (SPION)-cored spherical nucleic acid (DNA-SPION).

4. The process of claim 1, wherein the loading step further comprises loading the DNA-NP comprising PEG-linked oligonucleotides with a medicament comprising a phaiiii-aceutical acceptable carrier.

5. The process of claim 4, wherein the process further comprises administering the DNA-NP comprising PEG-linked oligonucleotides loaded with a medicament comprising a pharmaceutical acceptable carrier to a subject suffering from atherosclerosis.

6. The process of claim 1, wherein the loading step further comprises loading the DNA-NP comprising PEG-linked oligonucleotides with at least one nucleic acid.

7. The process of claim 6, wherein the loading step further comprises loading the DNA-NP comprising PEG-linked oligonucleotides with at least one of anti-miR712, anti-miR12, or siRNA against chemokine receptor 2 (CCR2).

8. The process of claim 5, wherein the process further comprises administering the DNA-NP comprising PEG-linked oligonucleotides loaded with a medicament comprising a pharmaceutical acceptable carrier to macrophages present in atherosclerotic lesions in blood vessels of the subject suffering from atherosclerosis.

* * * * *

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial
<220> FEATURE:
<223> OTHER INFORMATION: T30-NH2 oligonucleotide
<220> FEATURE:
<221> NAME/KEY: misc_feature
<222> LOCATION: (30)..(30)
<223> OTHER INFORMATION: 3' end modification: NH2

<400> SEQUENCE: 1
tttttttttt tttttttttt tttttttttt                              30

<210> SEQ ID NO 2
<211> LENGTH: 30
<212> TYPE: DNA
<213> ORGANISM: artificial
<220> FEATURE:
<223> OTHER INFORMATION: FITC-T30-NH2
<220> FEATURE:
<221> NAME/KEY: misc_feature
<222> LOCATION: (1)..(1)
<223> OTHER INFORMATION: 5' end modification: FITC
<220> FEATURE:
<221> NAME/KEY: misc_feature
<222> LOCATION: (30)..(30)
<223> OTHER INFORMATION: 3' end modification: NH2

<400> SEQUENCE: 2
tttttttttt tttttttttt tttttttttt                              30

<210> SEQ ID NO 3
<211> LENGTH: 30
<212> TYPE: DNA
<213> ORGANISM: Artificial
<220> FEATURE:
<223> OTHER INFORMATION: Cy3-T30-NH2 oligonucleotide
<220> FEATURE:
<221> NAME/KEY: misc_feature
<222> LOCATION: (1)..(1)
<223> OTHER INFORMATION: 5' end modification: Cy3
```

```
<220> FEATURE:
<221> NAME/KEY: misc_feature
<222> LOCATION: (30)..(30)
<223> OTHER INFORMATION: 3' end modification: NH2

<400> SEQUENCE: 3
tttttttttt tttttttttt tttttttttt                                    30

<210> SEQ ID NO 4
<211> LENGTH: 30
<212> TYPE: DNA
<213> ORGANISM: Artificial
<220> FEATURE:
<223> OTHER INFORMATION: Cy5.5-T30-NH2 oligonucleotide
<220> FEATURE:
<221> NAME/KEY: misc_feature
<222> LOCATION: (1)..(1)
<223> OTHER INFORMATION: 5' end modification: Cy5.5
<220> FEATURE:
<221> NAME/KEY: misc_feature
<222> LOCATION: (30)..(30)
<223> OTHER INFORMATION: 3' end modification: NH2

<400> SEQUENCE: 4
tttttttttt tttttttttt tttttttttt                                    30
```